(12) United States Patent
Ma et al.

(10) Patent No.: US 9,005,771 B2
(45) Date of Patent: Apr. 14, 2015

(54) 2-AZATRIPHENYLENE MATERIALS FOR ORGANIC LIGHT EMITTING DIODES

(75) Inventors: Bin Ma, Plainsboro, NJ (US); Raymond C. Kwong, Plainsboro, NJ (US)

(73) Assignee: Universal Display Corporation, Ewing, NJ (US)

( * ) Notice: Subject to any disclaimer, the term of this patent is extended or adjusted under 35 U.S.C. 154(b) by 550 days.

(21) Appl. No.: 12/778,362

(22) Filed: May 12, 2010

(65) Prior Publication Data

US 2010/0289406 A1 Nov. 18, 2010

Related U.S. Application Data

(60) Provisional application No. 61/177,435, filed on May 12, 2009.

(51) Int. Cl.
*H01J 1/63* (2006.01)
*C07D 409/10* (2006.01)
*C07F 15/00* (2006.01)
*H01L 51/00* (2006.01)
*C07D 221/18* (2006.01)
*C07D 401/10* (2006.01)
*C07D 405/10* (2006.01)
*C07D 421/10* (2006.01)
*C07D 495/04* (2006.01)
(Continued)

(52) U.S. Cl.
CPC .......... *H01L 51/0072* (2013.01); *C07D 221/18* (2013.01); *C07D 401/10* (2013.01); *C07D 405/10* (2013.01); *C07D 409/10* (2013.01); *C07D 421/10* (2013.01); *C07D 495/04* (2013.01); *C07F 15/0033* (2013.01); *C09K 11/06* (2013.01); *H01L 51/0074* (2013.01); *H01L 51/0085* (2013.01); *H01L 51/5016* (2013.01); *H01L 51/5096* (2013.01); *H05B 33/10* (2013.01); *C09K 2211/1007* (2013.01); *C09K 2211/1011* (2013.01); *C09K 2211/1029* (2013.01); *C09K 2211/1088* (2013.01); *C09K 2211/1092* (2013.01); *C09K 2211/1096* (2013.01); *C09K 2211/185* (2013.01)

(58) Field of Classification Search
None
See application file for complete search history.

(56) References Cited

U.S. PATENT DOCUMENTS 4,769,292 A 9/1988 Tang et al.
5,061,569 A 10/1991 VanSlyke et al.
(Continued)

FOREIGN PATENT DOCUMENTS

EP 0650955 5/1995
EP 1 555 269 7/2005
(Continued)

OTHER PUBLICATIONS

McIver et al. (Chem. Commun., 2008, 4750-4752).*
(Continued)

*Primary Examiner* — J. L. Yang
(74) *Attorney, Agent, or Firm* — Duane Morris LLP

(57) ABSTRACT

Compounds containing 2-azatriphenylene are provided. In particular, compounds containing a 2-azatriphenylene core having an additional aromatic group are provided. The compounds provided may be emissive or non-emissive materials. The compounds may be used in organic light emitting devices, particularly as host materials, hole blocking layer materials, or emitting dopants. Devices comprising 2-azatriphenylene containing compounds may demonstrate improved stability and efficiency.

21 Claims, 4 Drawing Sheets

(51) Int. Cl.
*C09K 11/06* (2006.01)
*H05B 33/10* (2006.01)
*H01L 51/50* (2006.01)

(56) References Cited

U.S. PATENT DOCUMENTS

| | | | |
|---|---|---|---|
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,884,363 | A | 3/1999 | Tofts |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,687,266 | B1 | 2/2004 | Ma et al. |
| 6,835,469 | B2 | 12/2004 | Kwong et al. |
| 7,087,321 | B2 | 8/2006 | Kwong et al. |
| 7,279,704 | B2 | 10/2007 | Walters et al. |
| 2002/0034656 | A1 | 3/2002 | Thompson et al. |
| 2002/0134984 | A1 | 9/2002 | Igarashi |
| 2003/0175553 | A1 | 9/2003 | Thompson et al. |
| 2003/0230980 | A1 | 12/2003 | Forrest et al. |
| 2004/0174116 | A1 | 9/2004 | Lu et al. |
| 2005/0025993 | A1 | 2/2005 | Thompson et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0202194 | A1 | 9/2006 | Jeong et al. |
| 2006/0251923 | A1 | 11/2006 | Lin et al. |
| 2006/0280965 | A1 | 12/2006 | Kwong et al. |
| 2007/0190359 | A1 | 8/2007 | Knowles et al. |
| 2008/0233287 | A1 | 9/2008 | Shtein et al. |
| 2009/0026935 | A1* | 1/2009 | Matsunami et al. .......... 313/504 |

FOREIGN PATENT DOCUMENTS

| | | | |
|---|---|---|---|
| EP | 2 103 665 | 9/2009 | |
| JP | 200511610 | 1/2005 | |
| JP | 2005-200416 | 7/2005 | |
| JP | 2007123392 | 5/2007 | |
| WO | WO 0139234 | 5/2001 | |
| WO | WO 0202714 | 1/2002 | |
| WO | WO 03040257 | 5/2003 | |
| WO | WO 2003060956 | 7/2003 | |
| WO | WO 2004093207 | 10/2004 | |
| WO | WO 2004107822 | 12/2004 | |
| WO | WO 2005014551 | 2/2005 | |
| WO | WO 2005030900 | 4/2005 | |
| WO | WO 2005089025 | 9/2005 | |
| WO | WO 2005123873 | 12/2005 | |
| WO | WO 2006009024 | 1/2006 | |
| WO | WO 2006056418 | 6/2006 | |
| WO | WO 2006082742 | 8/2006 | |
| WO | WO 2006098120 | 9/2006 | |
| WO | WO 2006103874 | 10/2006 | |
| WO | WO 2006114966 | 11/2006 | |
| WO | WO 2006132173 | 12/2006 | |
| WO | WO 2007004380 | 1/2007 | |
| WO | WO 2007063754 | 6/2007 | |
| WO | WO 2007063796 | 6/2007 | |
| WO | 2007254297 | 10/2007 | |
| WO | WO 2009/060995 | 5/2009 | |
| WO | WO-2009/060995 A1 * | 5/2009 | .............. C07F 15/00 |
| WO | WO 2009/021126 | 12/2009 | |

OTHER PUBLICATIONS

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," *Adv. Mater.*, 6(9):677-679 (1994).

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral Ru Phosphorescent Emitters," *Adv. Mater.*, 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

Ma, Yuguang et al., "Triplet Luminescent Dinuclear-Gold(I) Complex-Based Light-Emitting Diodes with Low Turn-On voltage," *Appl. Phys. Lett.*, 74(10):1361-1363 (1999).

Gao, Zhiqiang et al., "Bright-Blue Electroluminescence From a Silyl-Substituted ter-(phenylene-vinylene) derivative," *Appl. Phys. Lett.*, 74(6):865- 867 (1999).

Baldo, M.A. et al., "Very High-Efficiency Green Organic Light-Emitting Devices Based on Electrophosphorescence," *Appl. Phys. Lett.*, 75(1):4-6 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Hung, L.S. et al., "Anode Modification in Organic Light-Emitting Diodes by Low-Frequency Plasma Polymerization of $CHF_3$," *Appl. Phys. Lett.*, 78(5):673-675 (2001).

Ikai, Masamichi and Tokito, Shizuo, "Highly Efficient Phosphorescence From Organic Light-Emitting Devices with an Exciton-Block Layer," *Appl. Phys. Lett.*, 79(2):156-158 (2001).

Wang, Y. et al., "Highly Efficient Electroluminescent Materials Based on Fluorinated Organometallic Iridium Compounds," *Appl. Phys. Lett.*, 79(4):449-451 (2001).

Kwong, Raymond C. et al., "High Operational Stability of Electrophosphorescent Devices," *Appl. Phys. Lett.*, 81(1):162-164 (2002).

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic Light-Emitting Diodes with Phosphorescent Platinum Complexes Containing $N^{\wedge}C^{\wedge}N$-Coordinating Tridentate Ligand," *Appl. Phys. Lett.*, 86:153505-1 - 153505-3 (2005).

Okumoto, Kenji et al., "Green Fluorescent Organic Light-Emitting Device with External Quantum Efficiency of Nearly 10%," *Appl. Phys. Lett.*, 89:063504-1 — 063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1 -123509-3 (2007).

Aonuma, Masaki et al., "Material Design of Hole Transport Materials Capable of Thick-Film Formation in Organic Light Emitting Diodes," *Appl. Phys. Lett.*, 90:183503-1 - 183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1 - 263503-3 (2007).

Adachi, Chihaya et al., "High-Efficiency Red Electrophosphorescence Devices," *Appl. Phys. Lett.*, 78(11):1622-1624 (2001).

Wong, Keith Man-Chung et al., A Novel Class of Phosphorescent Gold(III) Alkynyl-Based Organic Light-Emitting Devices with Tunable Colour, *Chem. Commun.*, 2906-2908 (2005).

(56) References Cited

OTHER PUBLICATIONS

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota, Yasuhiko, "5,5'-Bis(dimesitylboryl)-2,2'-bithiophene and 5,5''-Bis(dimesitylboryl)-2,2':5',2''-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yashiko et al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al., 1,2,4-Triazole Derivative as an Electron Transport Layer in Organic Electrolumuniscent Devices, *Jpn. J. Appl. Phys.*, 32:L917-L920 (1993).

Van Slyke, S. A. et al., "Organic Electroluminescent Devices with Improved Stability," *Appl. Phys. Lett.*, 69(15):2160-2162 (1996).

Baldo, M. A. et al., "Highly Efficient Phosphorescent Emission From Organic Electroluminescent Devices," *Nature*, 395:151-154 (1998).

Guo, Tzung-Fang et al., "Highly Eficient Electrophosphorescent Polymer Light-Emitting Devices," *Organic Electronics*, 1:15-20 (2000).

Palilis, Leonidas C., "Highly Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High$T_g$ Hole-Transport Molecules Based on Indolo[3,2-*b*]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

Hewlins, M. et al., "Preparation of Polycyclic Azaarenes by an Extended Pomeranz-Fritsch Procedure" *Synthesis*, 14: 2157-2163, 2007.

International Search Report and Written Opinion in PCT/US2010/034479 application.

Mciver A. et al.: "A general approach to 1-3,8,9 triphenylenes and azatriphenylenes: total synthesis of dehydrotylophorine and tylophorine" Chemical Communications, No. 39, Oct. 21, 2008, pp. 4750-4652.

R. Sasson, et al., "On the Emission Spectrum of Triphenylene," Journal of Luminescence, 1988, vol. 39, pp. 223-225.

* cited by examiner

2-AZATRIPHENYLENE MATERIALS FOR ORGANIC LIGHT EMITTING DIODES

This application claims priority to U.S. Provisional Application Ser. No. 61/177,435, filed May 12, 2009, the disclosure of which is herein expressly incorporated by reference in its entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel organic materials that may be advantageously used in organic light emitting devices. More particularly, the present invention relates to novel 2-azatriphenylene containing compounds and devices containing such compounds.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine)iridium, denoted $Ir(ppy)_3$, which has the structure:

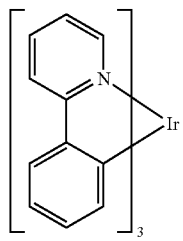

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Novel organic compounds are provided. The compounds comprise 2-azatriphenylene containing compounds that may be advantageously used in OLEDs. In particular, these compounds may be used as a host material, hole blocking material, or ligand for an emissive metal complex. Devices containing a 2-azatriphenylene compounds provided herein may have improved stability and efficiency. Novel compounds are provided, the compounds including the structure:

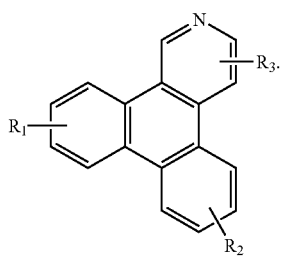

FORMULA I $R_1$, $R_2$, and $R_3$ may represent mono, di, tri, or tetra substitutions. $R_1$, $R_2$, and $R_3$ are independently selected from the group consisting of hydrogen, alkyl, alkoxy, amino, alkenyl, alkynyl, arylkyl, aryl, and heteroaryl. At least one of $R_1$, $R_2$, and $R_3$ is an aryl or heteroaryl. Preferably, $R_3$ is a substitution ortho to the nitrogen.

One group of compounds are provided wherein the compound has the formula FORMULA I and the compound is not coordinated to a metal. Preferably, these compounds may be used as host materials in the emissive layer or as non-emitting materials in various other non-emissive layers in OLEDs.

Preferably, $R_1$ is selected from the group consisting of alkyl, alkoxy, amino, alkenyl, alkynyl, arylkyl, aryl, and heteroaryl. More preferably, $R_1$ is an aryl or heteroaryl. Preferably, $R_2$ is selected from the group consisting of alkyl, alkoxy, amino, alkenyl, alkynyl, arylkyl, aryl, and heteroaryl. More preferably, $R_2$ is an aryl or heteroaryl. Preferably, $R_3$ is selected from the group consisting of alkyl, alkoxy, amino, alkenyl, alkynyl, arylkyl, aryl, and heteroaryl. More preferably, $R_3$ is an aryl or heteroaryl. Preferably, each of $R_1$, $R_2$, and $R_3$ is an aryl or heteroaryl.

Particular compounds having FORMULA I are provided including compounds selected from the group consisting of Compound 1G-Compound 70G. $R'_3$, $R_4$, $R_5$, $R_6$, $R_7$, and $R_8$ may represent mono, di, tri, tetra, or penta substitutions. $R'_3$, $R_4$, $R_5$, $R_6$ are independently selected from the group consisting of hydrogen, alkyl, alkoxy, amino, alkenyl, alkynyl, arylkyl, aryl, and heteroaryl. Specific compounds having FORMULA I are also provided. Each of $R_1$, $R_2$, $R_3$, $R_4$, $R_5$, $R_6$, $R_7$, and $R_8$ is hydrogen, such as compounds selected from the group consisting of Compound 1-Compound 70.

Another group of compounds containing a cyclometallated ligand are provided. The compounds comprise a ligand L having the formula:

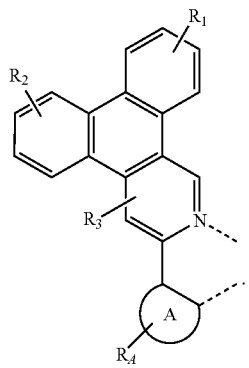

FORMULA II

A is a 5-membered or 6-membered aryl or heteroaryl ring. $R_A$ may represent a mono, di, tri, or tetra substitution. $R_A$ is selected from the group consisting of hydrogen, alkyl, alkoxy, amino, alkenyl, alkynyl, arylkyl, aryl, and heteroaryl. The ligand L is coordinated to a metal having an atomic number greater than 40. Preferably, the metal is Ir.

These compounds may be used as emitting materials because the cyclometallated complex of such compounds as ligands is expected to provide emissive properties. Preferably, these compounds may be used as emitting dopants in the emissive layer of an OLED. These compounds may also be used as non-emitting materials. In particular, the compounds may be used in parts of a device where the emissive properties of the compound are not used, such as the hole blocking layer.

In one aspect, compounds are provided wherein the ligand L is included in a homoleptic compound. In another aspect, compounds are provided wherein the ligand L is included in a heteroleptic compound. In particular, compounds are provided wherein the compound has the formula $(L)_n(L')_{3-n}Ir$. In is 1 or 2. In one aspect, preferably n is 1. In another aspect, preferably n is 2. L' is selected from the group consisting of:

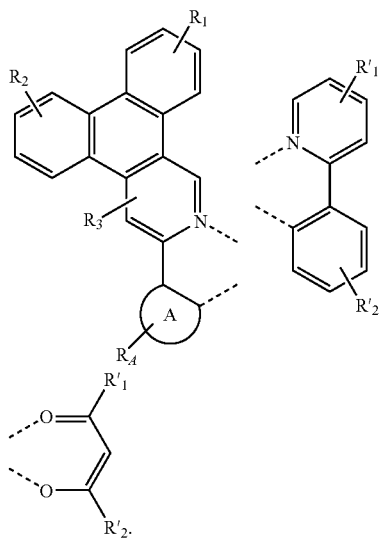

$R'_1$ and $R'_2$ may represent a mono, di, tri, or tetra substitutions. $R'_1$ and $R'_2$ is selected from the group consisting of hydrogen, alkyl, alkoxy, amino, alkenyl, alkynyl, arylkyl, aryl, and heteroaryl. L has a different structure than L'.

Compounds comprising particular ligands are also provided, including compounds having a ligand L selected from the group consisting of Compound 71G-Compound 78G. $R_4$ and $R_5$ may represent mono, di, tri, tetra, or penta substitutions. $R_4$ and $R_5$ are independently selected from the group consisting of hydrogen, alkyl, alkoxy, amino, alkenyl, alkynyl, arylkyl, aryl, and heteroaryl. Specific ligands are also provided, including ligands L selected from the group consisting of Compound 71-Compound 78 (i.e., $R_1$, $R_2$, $R_3$, $R_4$, and $R_5$ are each hydrogen).

Particular compounds comprising an Ir complex containing a 2-azatriphenylene ligand are also provided, including compounds selected from the group consisting of Compound 79G-Compound 96G. $R_4$ and $R_5$ are independently selected from the group consisting of hydrogen, alkyl, alkoxy, amino, alkenyl, alkynyl, arylkyl, aryl, and heteroaryl. Specific compounds comprising an Ir complex containing a 2-azatriphenylene ligand are also provided, including compounds selected from the group consisting of Compound 79-Compound 96 (i.e., $R_1$, $R_2$, $R_3$, $R_4$, $R_5$, $R'_1$, and $R'_2$ are each hydrogen).

Additionally, an organic light emitting device is also provided. The device comprising an anode, a cathode, and a first organic layer, disposed between the anode and the cathode. The first organic layer further comprising a compound that includes the structure:

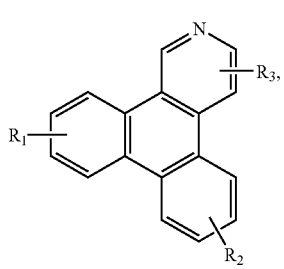

FORMULA I as described above. Selections for the substituents described as preferred for the compounds including the structure FORMULA I are also preferred for use in a device that comprises a compound including the structure FORMULA I. These selections include those described for $R_1$, $R_2$, $R_3$, and A.

$R_1$, $R_2$, and $R_3$ may represent mono, di, tri, or tetra substitutions. $R_1$, $R_2$, and $R_3$ are independently selected from the group consisting of hydrogen, alkyl, alkoxy, amino, alkenyl, alkynyl, arylkyl, aryl, and heteroaryl. At least one of $R_1$, $R_2$, and $R_3$ is an aryl or heteroaryl.

In one aspect, the device comprises a compound having the formula FORMULA I wherein the compound is not coordinated to a metal. Particular compounds that may be used in such devices include compounds selected from the group consisting of Compound 1G-Compound 70G. $R'_3$, $R_4$, $R_5$, $R_6$, $R_7$, and $R_8$ may represent mono, di, tri, tetra, or penta substitutions. $R'_3$, $R_4$, $R_5$, $R_6$, $R_7$, and $R_8$ are independently selected from the group consisting of hydrogen, alkyl, alkoxy, amino, alkenyl, alkynyl, arylkyl, aryl, and heteroaryl. Certain devices are provided which contain a compound selected from the group consisting of Compound 1-Compound 70 (i.e., each of $R_1$, $R_2$, $R_3$, $R_4$, $R_5$, $R_6$, $R_7$, and $R_8$ is hydrogen).

In another aspect, devices are provided wherein the first organic layer is an emissive layer and the compound including the structure FORMULA I is a host. Moreover, the first organic layer may further comprise an emitting dopant. Preferably, the emitting dopant has the formula:

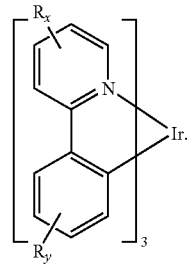

E1

$R_x$ and $R_y$ may represent mono, di, tri, or tetra substitutions. $R_x$ and $R_y$ are independently selected from the group consisting of hydrogen, alkyl, and aryl.

Additionally, devices are provided wherein the device comprises a compound comprising a ligand L having the formula:

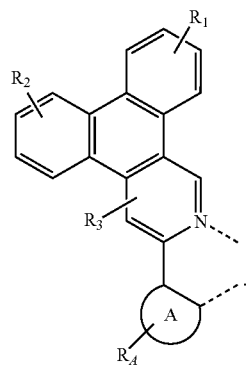

FORMULA II

A is a 5-membered or 6-membered aryl or heteroaryl ring. $R_4$ may represent a mono, di, tri, or tetra substitution. $R_4$ is selected from the group consisting of hydrogen, alkyl, alkoxy, amino, alkenyl, alkynyl, arylkyl, aryl, and heteroaryl.

Particular ligands for use in such devices include ligands L selected from the group consisting of Compound 71G-Compound 78G. $R_4$ and $R_5$ may represent mono, di, tri, tetra, or penta substitutions. $R_4$ and $R_5$ are independently selected from the group consisting of hydrogen, alkyl, alkoxy, amino, alkenyl, alkynyl, aryl, and heteroaryl. Certain devices are provided which contain a compound having a ligand L selected from the group consisting of Compound 71-Compound 78 (i.e., $R_1$, $R_2$, $R_3$, $R_4$, and $R_5$ are each hydrogen).

Particular compounds for use in such devices include compounds selected from the group consisting of Compound 79G-Compound 96G. $R_4$ and $R_5$ may represent mono, di, tri, tetra, or penta substitutions. $R_4$ and $R_5$ are independently selected from the group consisting of hydrogen, alkyl, alkoxy, amino, alkenyl, alkynyl, aryl, and heteroaryl. Certain devices are provided which contain a compound selected from the group consisting of Compound 79-Compound 96 (i.e., $R_1$, $R_2$, $R_3$, $R_4$, $R_5$, $R'_1$, and $R'_2$ are each hydrogen).

In one aspect, devices are provided wherein the first organic layer is an emissive layer and the compound including the structure FORMULA II is an emitting dopant. Preferably, the first organic layer further comprises a host material.

In another aspect, devices are provided wherein the device comprises a second organic layer that is a non-emissive layer. The compound including the structure FORMULA II is a non-emissive material in the second organic layer. Preferably, the second organic layer is a hole injection or transport layer and the compound including the structure FORMULA II is a hole injection or transport material.

Additionally, a consumer product comprising a device is also provided. The device further comprises an anode, a cathode, and a first organic layer disposed between the anode and the cathode. The first organic layer further comprises a compound including the structure FORMULA I, as described above. Selections for the substituents described as preferred for the compounds including the structure FORMULA I are also preferred for use in a device that comprises a compound including the structure FORMULA I. These selections include those described for $R_1$, $R_2$, $R_3$, and A.

$R_1$, $R_2$, and $R_3$ may represent mono, di, tri, or tetra substitutions. $R_1$, $R_2$, and $R_3$ are independently selected from the group consisting of alkyl, alkoxy, amino, alkenyl, alkynyl, arylkyl, aryl, heteroaryl and hydrogen. At least one of $R_1$, $R_2$, and $R_3$ is an aryl or heteroaryl.

In one aspect, the device of the consumer product may contain a 2-azatriphenylene compound having FORMULA II. In another aspect, the device of the consumer product may contain a compound comprising a ligand including 2-azatriphenylene coordinated to a metal having an atomic number greater than 40.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
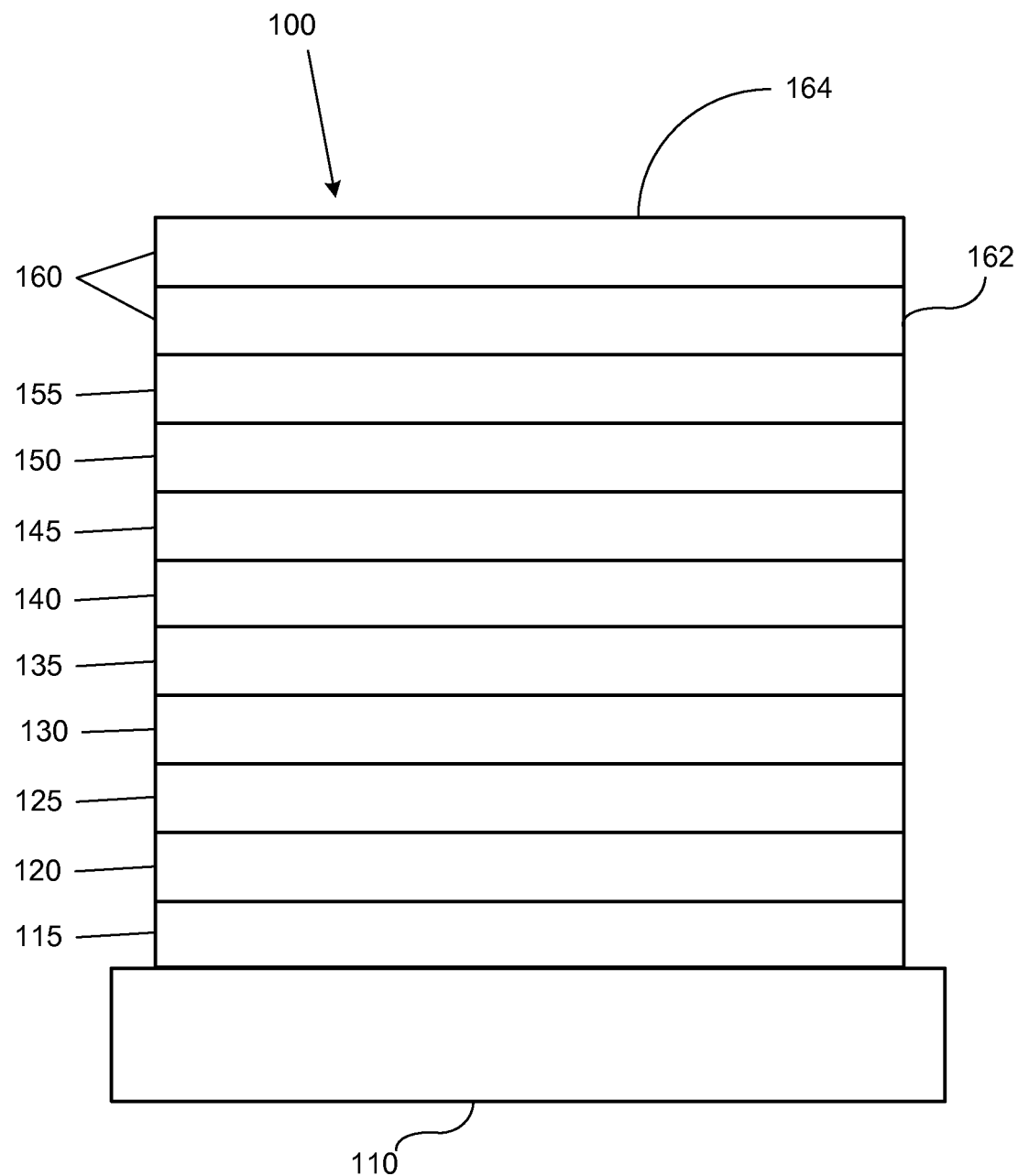
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
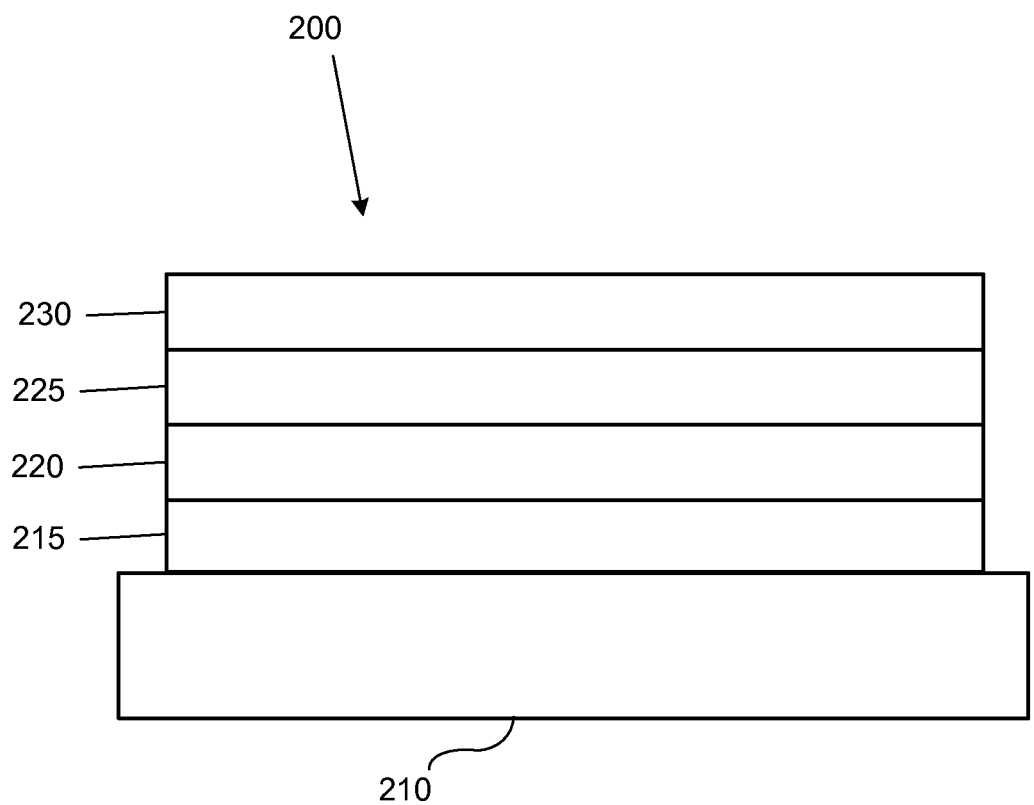
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
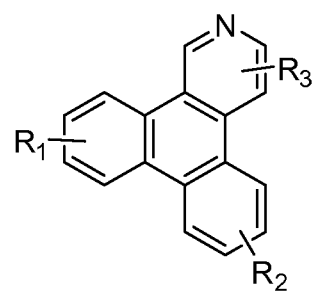
FIG. 3 shows a 2-azatriphenylene compound.

Novel compounds are provided, the compounds including 2-azatriphenylene (illustrated in FIG. 3). In particular, the compounds include 2-azatriphenylene having an additional aromatic substituent (i.e., aryl or heteroaryl). These compounds may be advantageously used in OLEDs to provide devices having improved stability and efficiency.

One group of novel compounds include compounds having the formula of FORMULA I without a coordinated metal. Preferably, these compounds are used as non-emitting compounds such as host materials and/or hole blocking layer materials.

Figure 4:
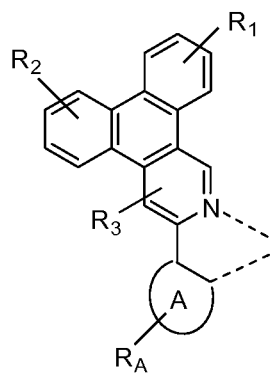
FIG. 4 shows a ligand containing 2-azatriphenylene.

Another group of novel compounds are provided which include compounds wherein the 2-azatriphenylene structure is incorporated into a ligand coordinated to a metal (illustrated in FIG. 4). These compounds may be expected to demonstrate phosphorescent emissive properties because of the cyclometallated ligand. Thus, these compounds may be preferably used as emitting materials. In addition, these compounds may also be used as non-emitting materials in layers of a device which do not require the emissive properties of such compounds (e.g., hole blocking layer). Particular 2-azatriphenylene ligands include in a compound are provided.

1-azatriphenylene containing compounds have been reported in the literature (see, JP2007189001). However, the class of compounds provided herein contain novel structures. The synthesis provided is directed to making 1-azatriphenylene compounds rather than a synthetic method for making 2-azatriphenylene compounds. Moreover, the 1-azatriphenylene synthetic methods are not necessarily applicable to making 2-azatriphenylene compounds.

The methods provided herein are directed to 2-azatriphenylene compounds.

At least one example of 2-azatriphenylene compounds is reported in the literature (see, Hewline, M. et al., *Synthesis*, 14: 2157-2163, 2007). However, the reference does not provide compounds having the additional aromatic substituent as provided herein and does not suggest 2-azatriphenylene compounds in the context of an OLED. 2-azatriphenylene compounds lacking the additional aromatic substituent may not be suitable for use in OLEDs. The additional aromatic group substituent at $R_1$, $R_2$, and/or $R_3$ on the 2-azatriphenylene core of the compound provides a novel structure and may also provide beneficial properties. In particular, the additional aromatic substituent (i.e., an aryl or a heteroaryl) may provide a further improvement in the stability of the compound via the additional conjugation. In addition, there are no known references providing synthetic methods for making 2-azatriphenylene compounds. Thus, for at least these reasons, the compounds provided herein may be particularly desirable. The beneficial properties of the compounds may apply to both emissive and non-emissive compounds.

Moreover, most of the azatriphenylene compounds previously reported are 1-azatriphenylene compounds. While the synthesis of 1-azatriphenylenes is believed to be well known, the synthetic methods for making 1-azatriphenylenes do not necessarily apply to making 2-azatriphenylene compounds. Despite previous reports of azatriphenylene compounds, there have been no reports regarding the synthetic methods for making such 2-azatriphenylene compounds as provided herein. Many of the novel 2-azatriphenylene compounds provided can be synthesized using the methods described herein.

Triphenylene is a polyaromatic hydrocarbon with high triplet energy, yet high π-conjugation and a relatively small energy difference between the first singlet and first triplet levels. This would indicate that triphenylene has relatively easily accessible HOMO and LUMO levels compared to other aromatic compounds with similar triplet energy (e.g., biphenyl). Triphenylene and its derivatives may be especially good hosts at least because these compounds can accommodate red, green and even blue phosphorescent dopants to give high efficiency without energy quenching. High efficiency and high stability PHOLEDs with triphenylene hosts were demonstrated from previous work (see, US2006/0280965 and PCT/US2008/072499).

Compounds containing the triphenylene derivative azatriphenylene may be especially beneficial. Azatriphenylene has a lower LUMO than triphenylene (i.e., a LUMO more accessible than that of triphenylene) and thus azatriphenylene may improve electron transport in OLED devices. In addition, azatriphenylene may offer an improved charge balance that results in improvements in device performance in terms of lifetime, efficiency and low voltage. Moreover, previous work has shown that nitrogen in the 2 position of other host materials (e.g., aza-dibenzothiophene) may provide improvements. Without being limited to any theory as to how the invention works, it is thought that nitrogen in the 2 position in azatriphenylene containing compounds (i.e., 2-azatriphenylene) may also provide beneficial properties.

In addition, the compounds provided may be particularly advantageous because the 2-azatriphenylene containing compounds may be more easily reduced than previously reported triphenylene compounds and derivatives. Table 1 provides the DFT calculation properties of triphenylene and its derivates. In particular, Table 1 contains the LUMO level as calculated for triphenylene, 1-azatriphenylene, and 2-azatriphenylene. The DFT calculation results shown in Table 1 demonstrate that 2-azatriphenylene has a LUMO of −1.34 eV notably lower than triphenylene and 1-azatriphenylene which have LUMO levels of −0.93 eV and −1.23 eV, respectively. Additionally, the DFT calculations shown in Table 1 suggest that the triplet energy of 2-azatriphenylene is similar to the triplet energy of triphenylene and 1-azatriphenylene, which was confirmed by the experimental results of Compound 1. Therefore, 2-azatriphenylene containing compounds may be more easily reduced and thus provide devices with low operating voltage.

TABLE 1

| Compound | HOMO (ev) | LUMO (ev) | Gap (ev) | Dipole (debye) | Calc. T1 (nm) |
|---|---|---|---|---|---|
| 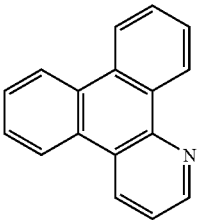 Triphenylene | −5.85 | −0.93 | −4.92 | 0.00 | 434 |
| 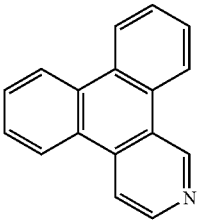 1-Azatriphenylene | −5.97 | −1.23 | −4.75 | 1.76 | 429 |
| 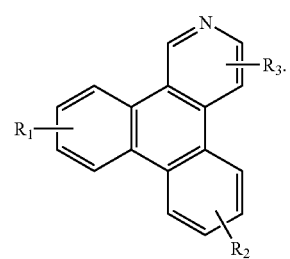 2-Azatriphenylene | −6.08 | −1.34 | −4.74 | 2.82 | 430 |

Novel 2-azatriphenylene containing compounds are provided herein. These compounds provide a new type of materials which may be advantageously used in OLEDs. In particular, these compounds may be used in OLEDs fabricated by both vapor deposition or solution processing methods, thereby giving stable and efficient devices.

Novel compounds are provided, the compounds include the structure:

FORMULA I $R_1$, $R_2$, and $R_3$ may represent mono, di, tri, or tetra substitutions, and each of $R_1$, $R_2$, and $R_3$ are independently selected from the group consisting of hydrogen, alkyl, alkoxy, amino, alkenyl, alkynyl, arylkyl, aryl, and heteroaryl. At least one of $R_1$, $R_2$ and $R_3$ is an aryl or a heteroaryl.

In one aspect, $R_1$ is selected from the group consisting of alkyl, alkoxy, amino, alkenyl, alkynyl, arylkyl, aryl, and heteroaryl. Preferably, $R_1$ is an aryl or heteroaryl. In another aspect, $R_2$ is selected from the group consisting of alkyl, alkoxy, amino, alkenyl, alkynyl, arylkyl, aryl, and heteroaryl. Preferably, $R_2$ is an aryl or heteroaryl. In yet another aspect, $R_3$ is selected from the group consisting of alkyl, alkoxy, amino, alkenyl, alkynyl, arylkyl, aryl, and heteroaryl. Preferably, $R_3$ is an aryl or heteroaryl. In a further aspect, each of $R_1$, $R_2$, and $R_3$ is an aryl or a heteroaryl.

One group of compounds provided include compounds having the formula:

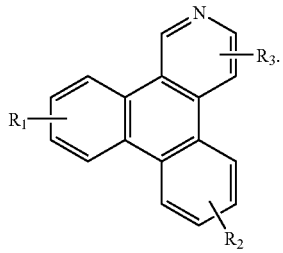

FORMULA I

The compound is not coordinated to a metal.

Such compounds may be further substituted at $R_1$, $R_2$ and $R_3$, as described above. These compounds may be used in a variety of layers, both emissive and non-emissive, within the device structure. Preferably, these compounds may be used as hosts in the emissive layer of an OLED. Such compounds may also be preferably used as non-emitting materials in other non-emissive layers of an OLED (e.g., hole blocking layer).

Preferably, $R_3$ is a substitution ortho to the nitrogen. By adding the $R_3$ substituent at the carbon next to the nitrogen (i.e., ortho to the nitrogen), the stability of the compound may be improved. Without being bound by theory, it is thought that that the pyridine ring lacking substituents at the positions ortho to the nitrogen atom may be especially vulnerable to degradation and thus less stable. In particular, without being bound by theory, it is believed that nitrogen bonds exposed in the absence of a substitution ortho to the nitrogen may be the weak link in possible degradation pathways. Thus, a substitution ortho to the nitrogen may provide steric protection to the pyridine ring thereby improving stability of the compound. Therefore, a compound having $R_3$ as an substitution ortho to the nitrogen may improve the stability of the 2-aza-triphenylene compound.

Particular compounds having the formula of FORMULA I are provided, wherein the compound is selected from the group consisting of:

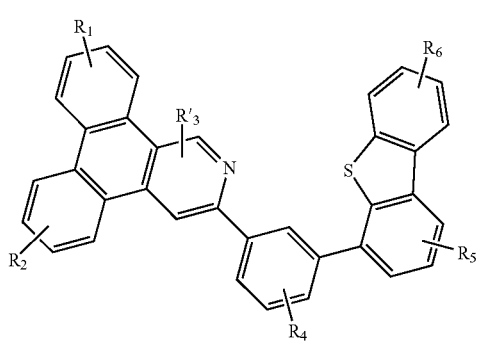

Compound 1G

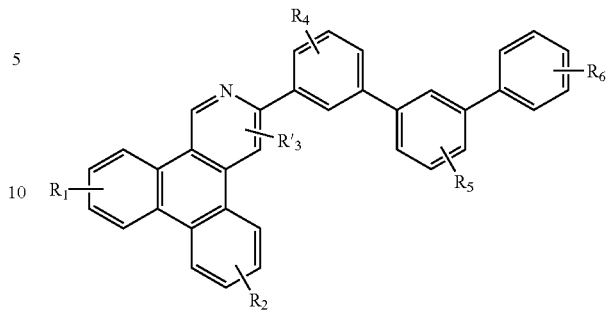

Compound 2G

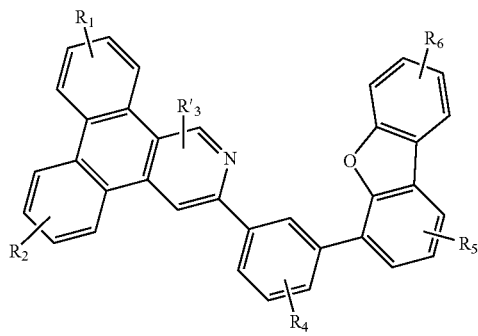

Compound 3G

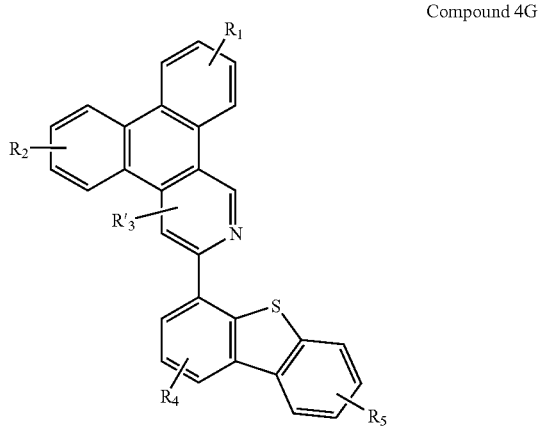

Compound 4G

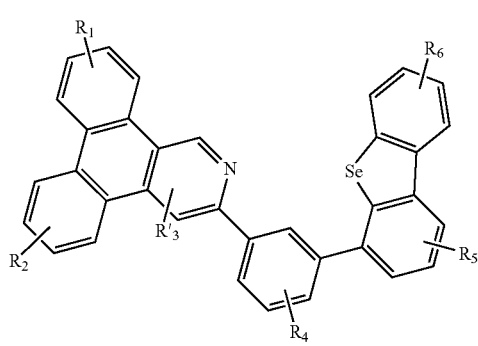

Compound 5G

Compound 6G
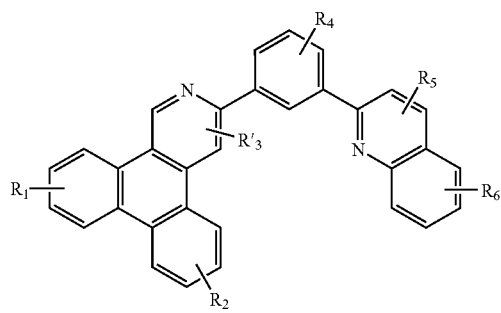
Compound 7G
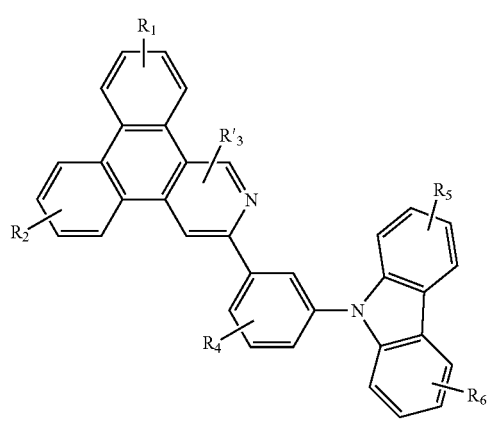
Compound 8G
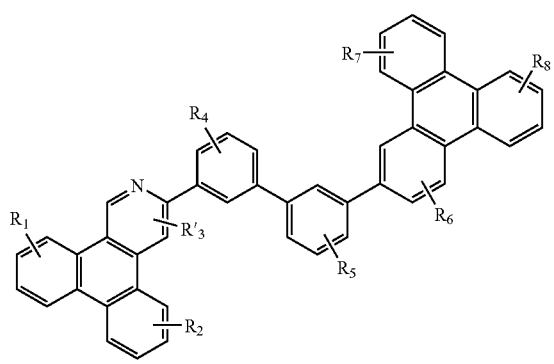
Compound 9G
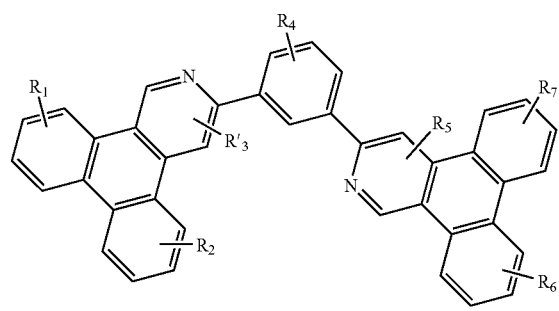
Compound 10G
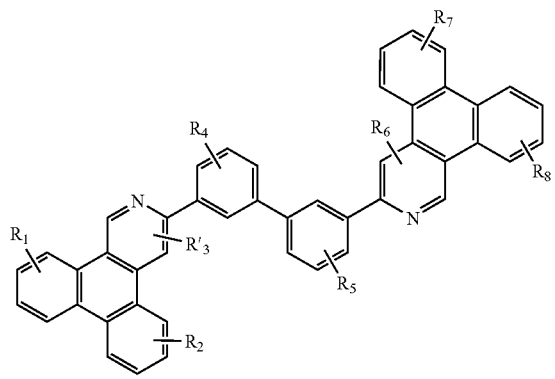
Compound 11G
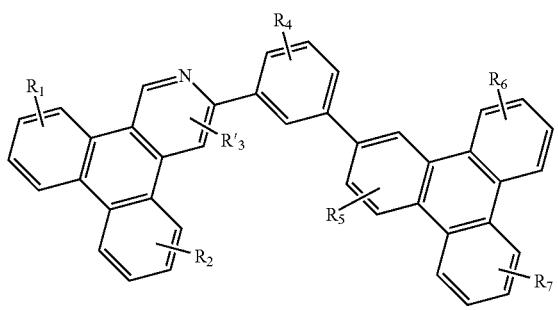
Compound 12G
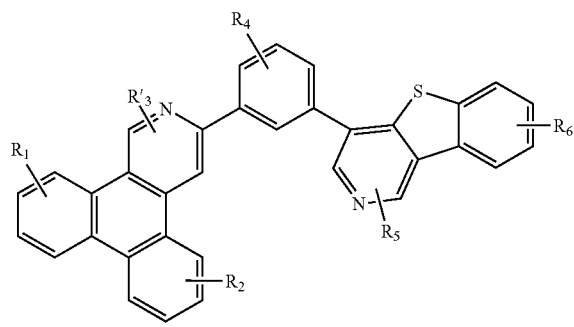
Compound 13G
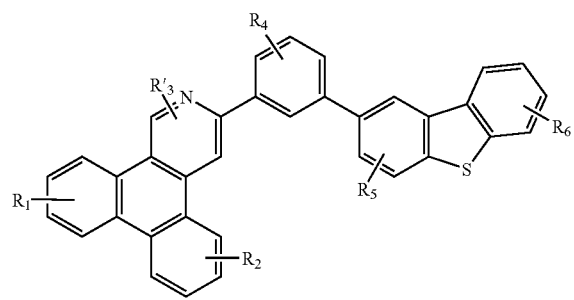

Compound 14G
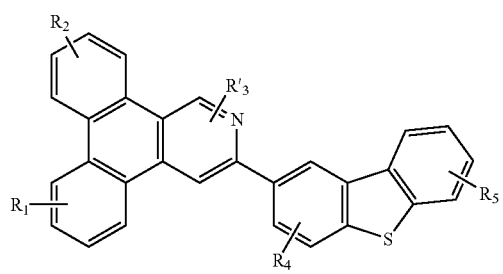
Compound 15G
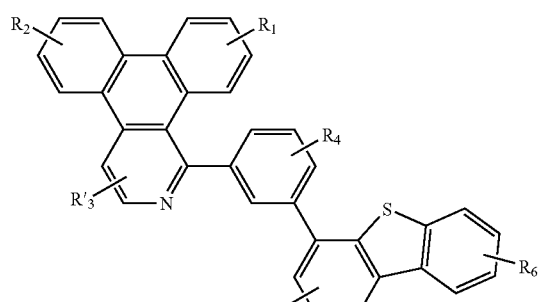
Compound 16G
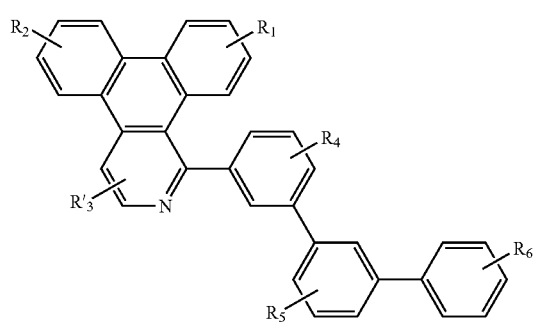
Compound 17G
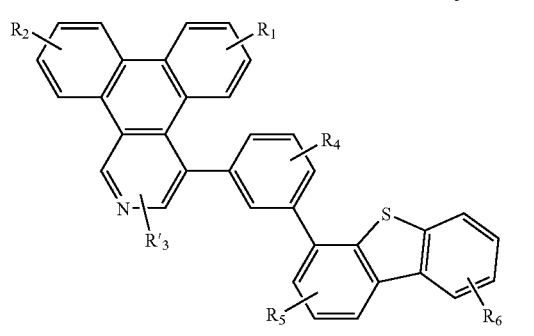
Compound 18G
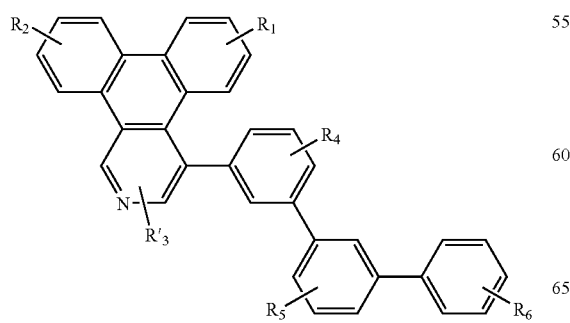
Compound 19G
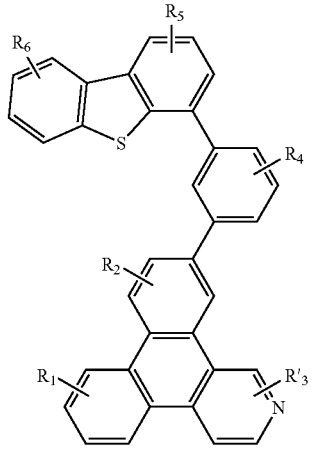
Compound 20G
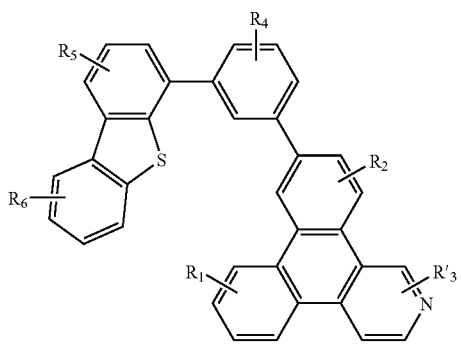
Compound 21G
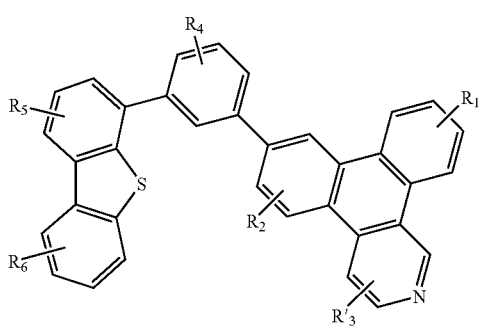
Compound 22G
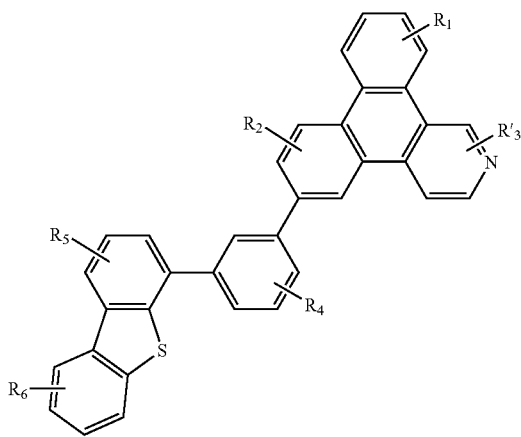

Compound 23G
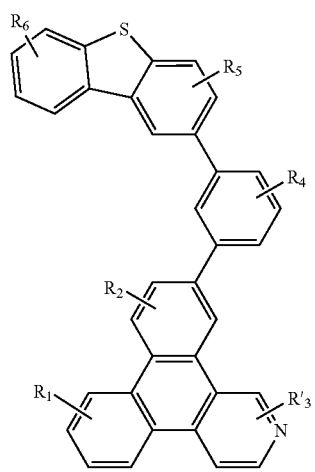
Compound 24G
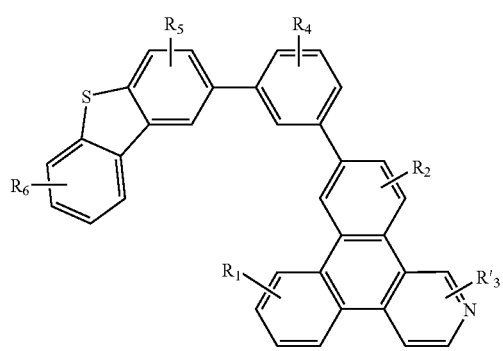
Compound 25G
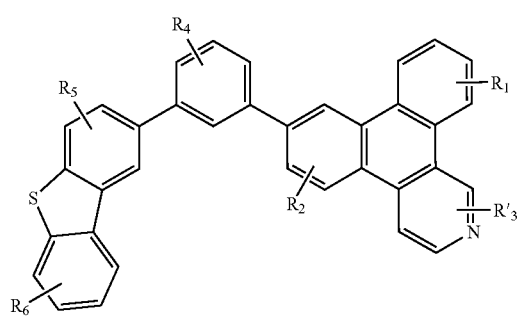
Compound 26G
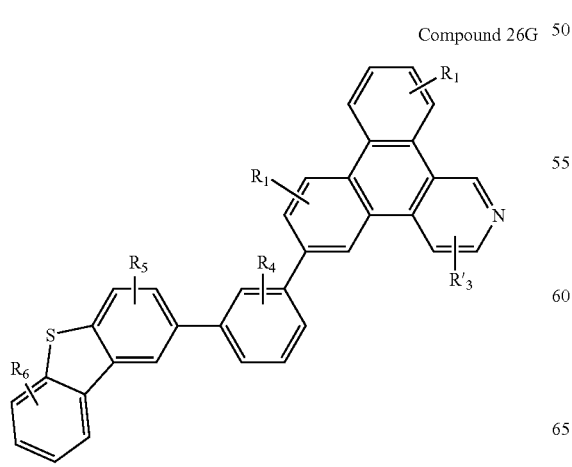
Compound 27G
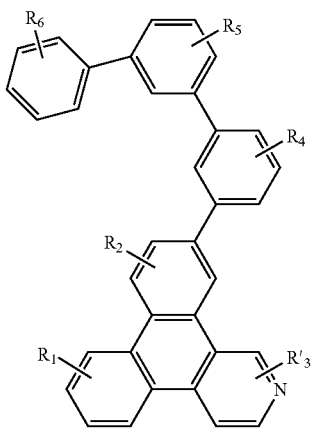
Compound 28G
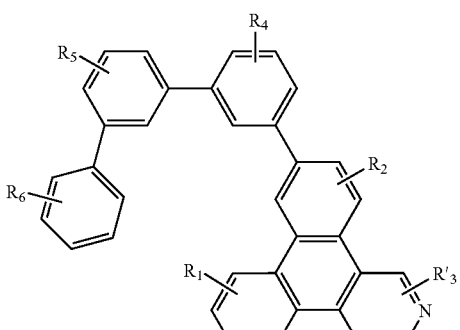
Compound 29G
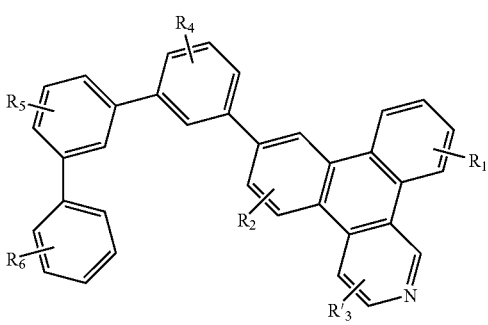
Compound 30G
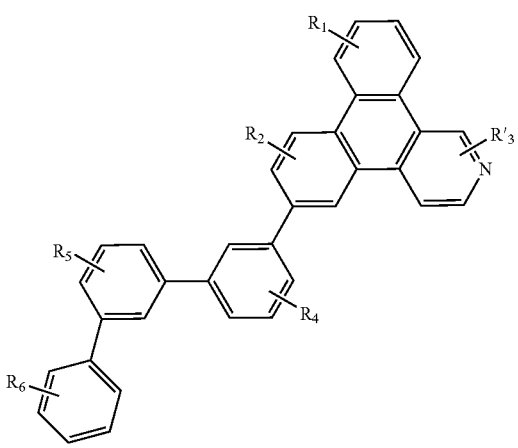

Compound 31G
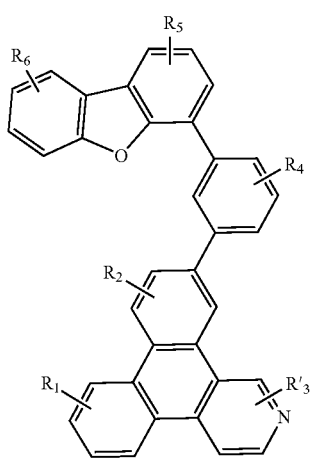
Compound 32G
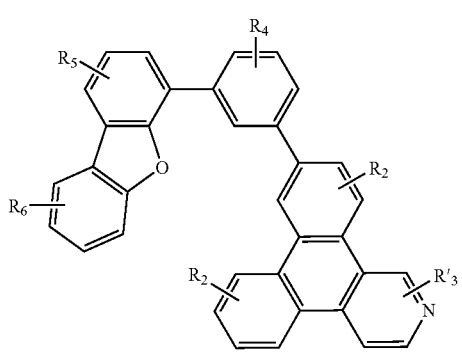
Compound 33G
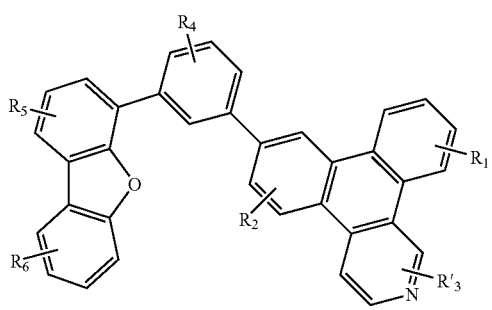
Compound 34G
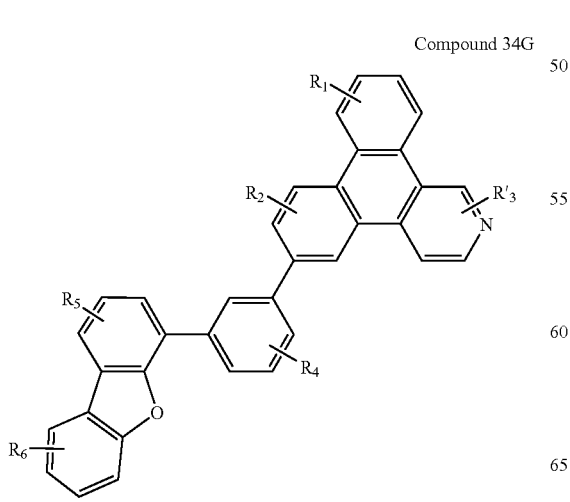
Compound 35G
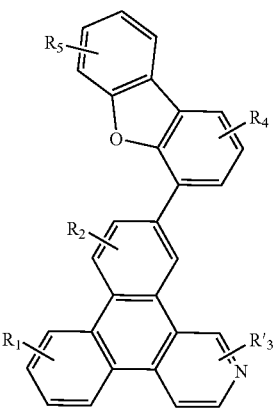
Compound 36G
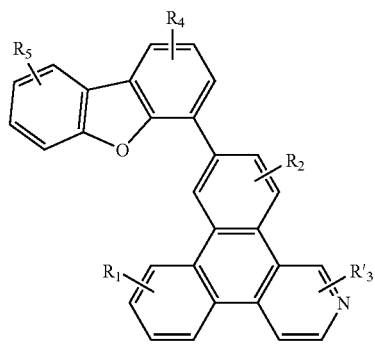
Compound 37G
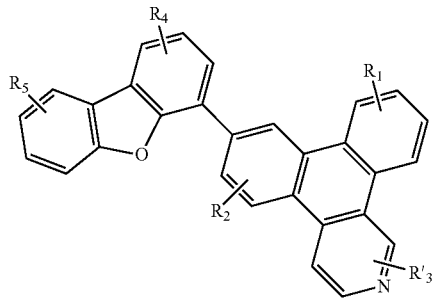
Compound 38G
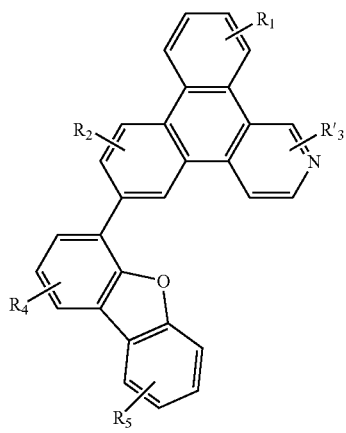

Compound 39G
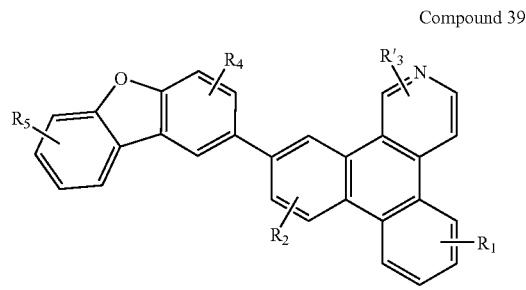
Compound 40G
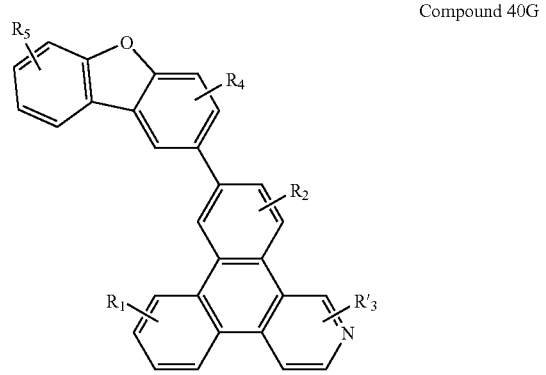
Compound 41G
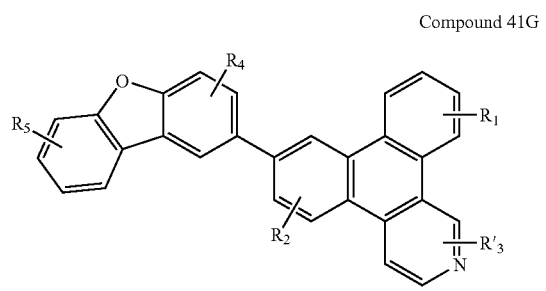
Compound 42G
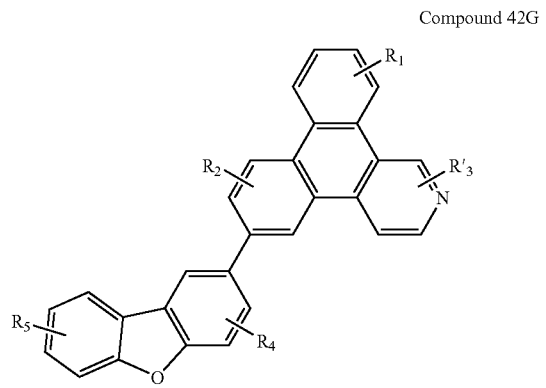
Compound 43G
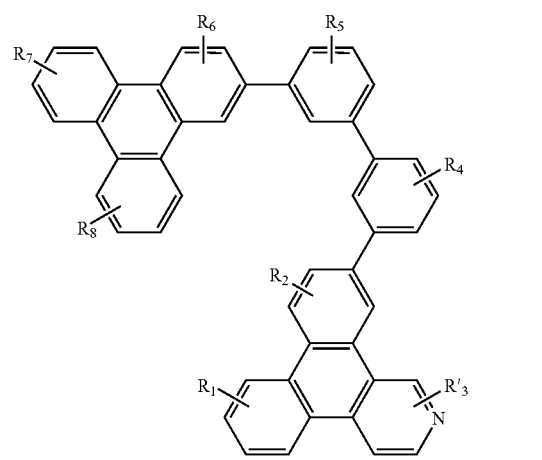
Compound 44G
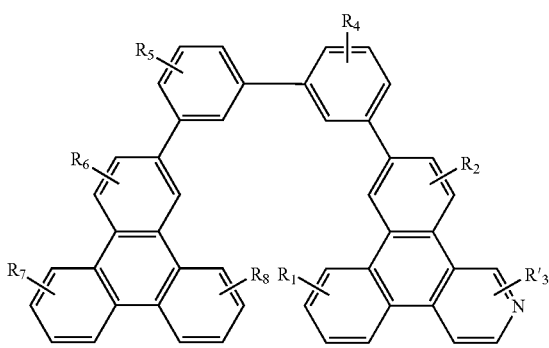
Compound 45G
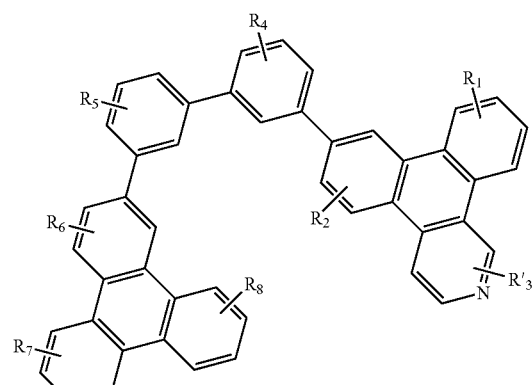

Compound 46G
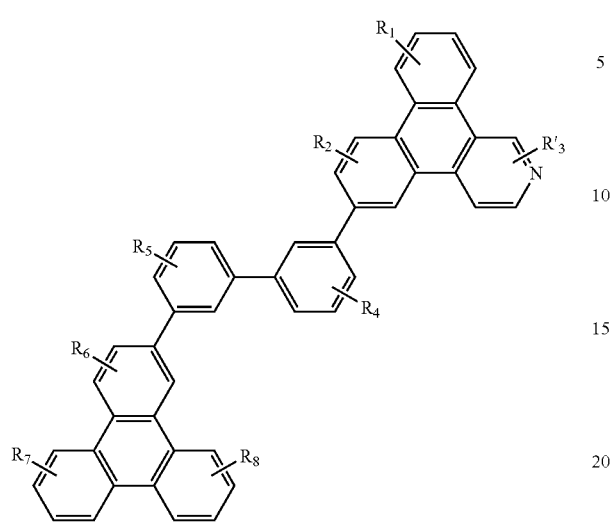
Compound 47G
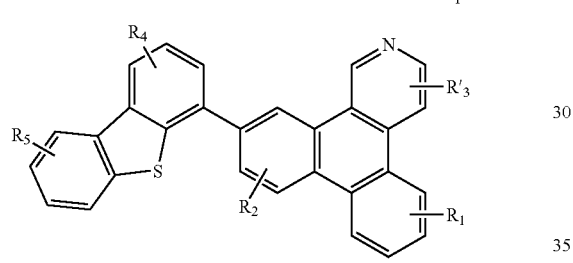
Compound 48G
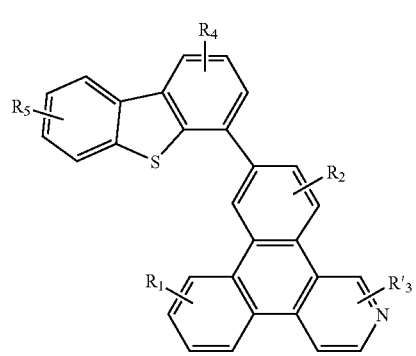
Compound 49G
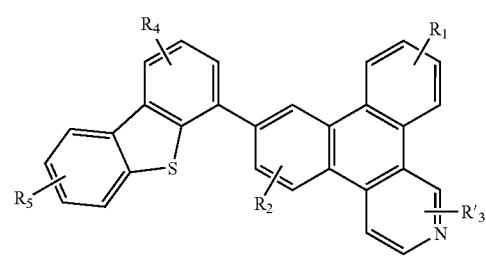
Compound 50G
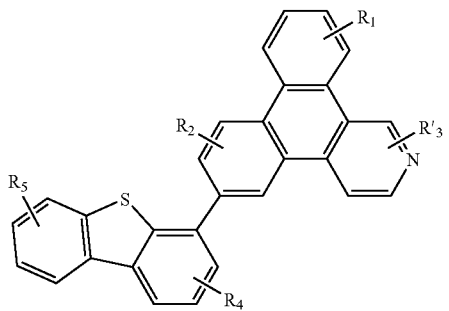
Compound 51G
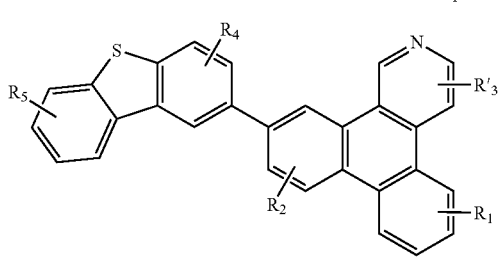
Compound 52G
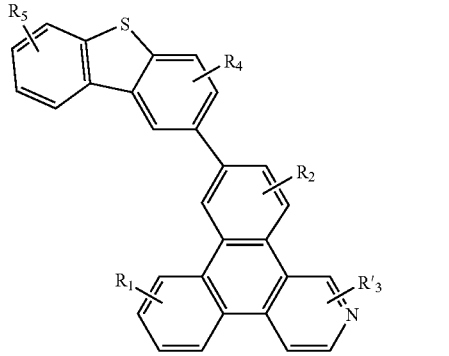
Compound 53G
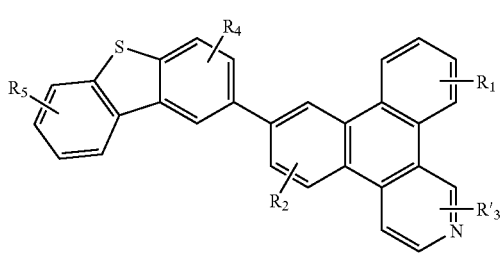
Compound 54G
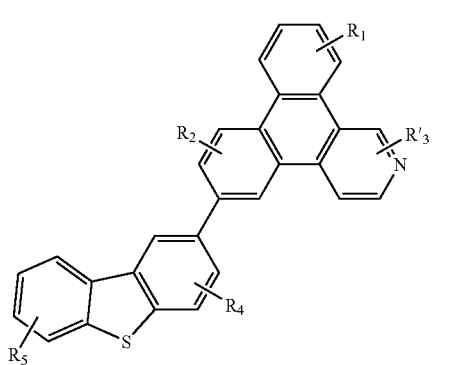

-continued
Compound 55G
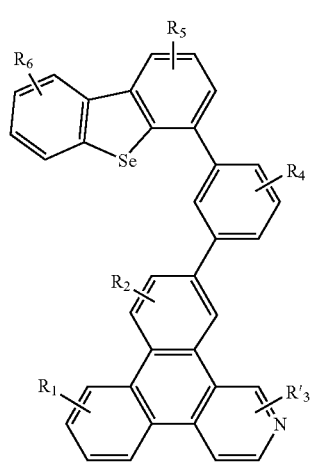
Compound 56G
Compound 57G
Compound 58G
-continued
Compound 59G
Compound 60G
Compound 61G
Compound 62G Compound 63G
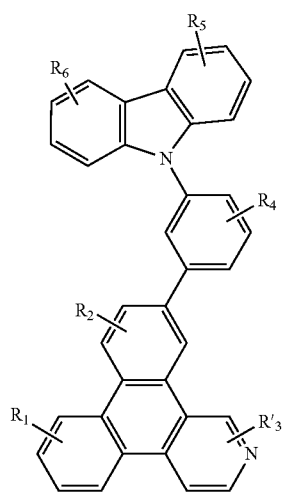

Compound 64G
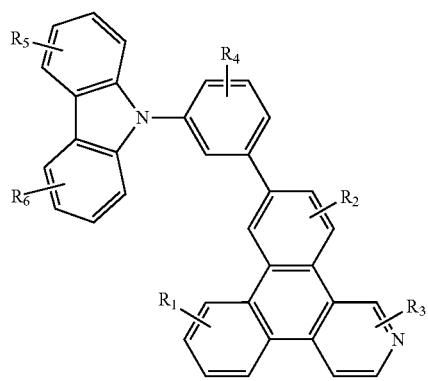

Compound 65G
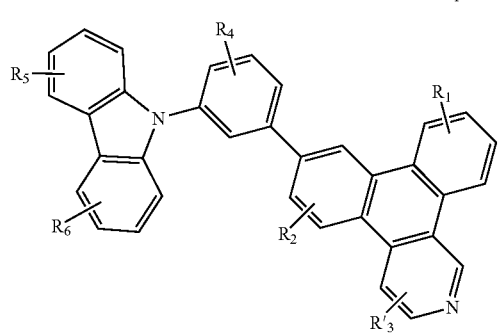

Compound 66G
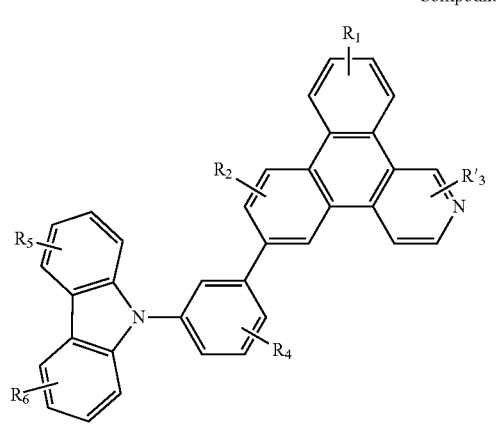

Compound 67G
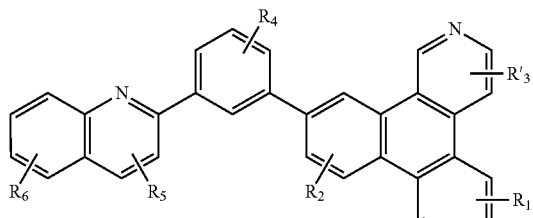

Compound 68G
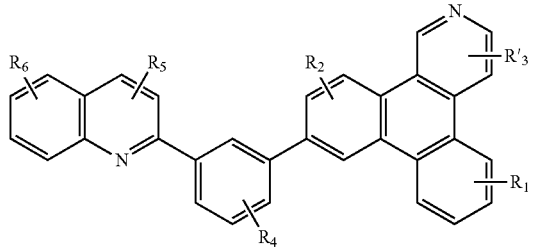

Compound 69G
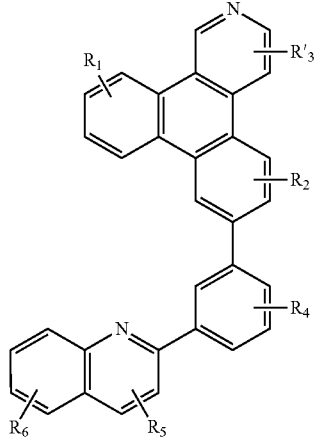

Compound 70G
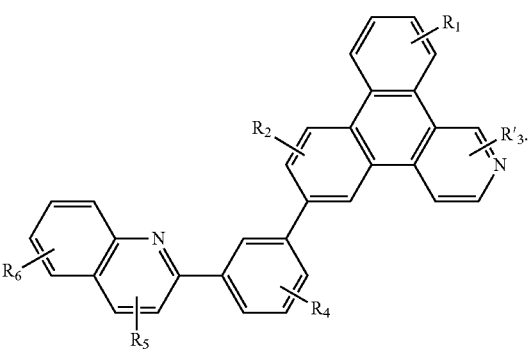
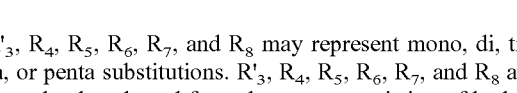

$R'_3$, $R_4$, $R_5$, $R_6$, $R_7$, and $R_8$ may represent mono, di, tri, tetra, or penta substitutions. $R'_3$, $R_4$, $R_5$, $R_6$, $R_7$, and $R_8$ are independently selected from the group consisting of hydrogen, alkyl, alkoxy, amino, alkenyl, alkynyl, arylkyl, aryl, and heteroaryl.

In addition, specific examples of compounds having the formula of FORMULA I also are provided. Each of the substituents $R_1$, $R_2$, $R_3$, $R'_3$, $R_4$, $R_5$, $R_6$, $R_7$, and $R_8$ is hydrogen. Specific compounds provided include compounds selected from the group consisting of:

Compound 1
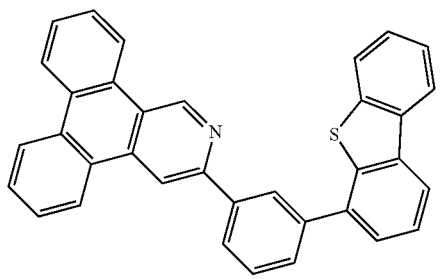
Compound 2
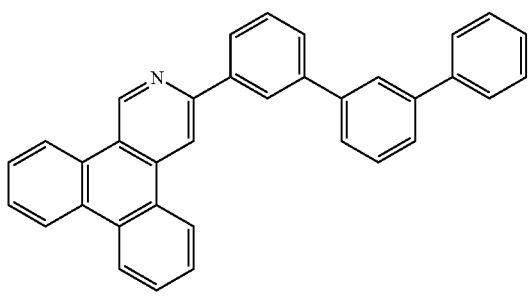
Compound 3
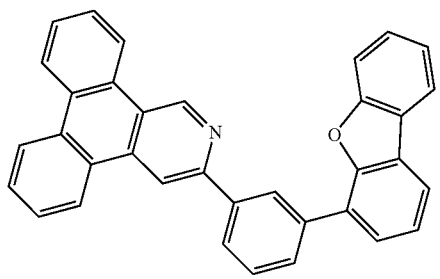
Coumpound 4
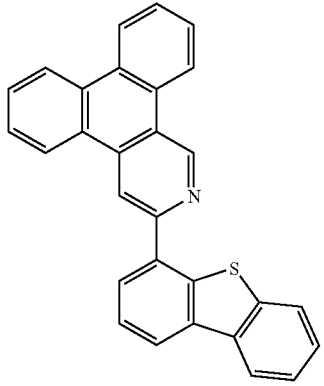
Compound 5
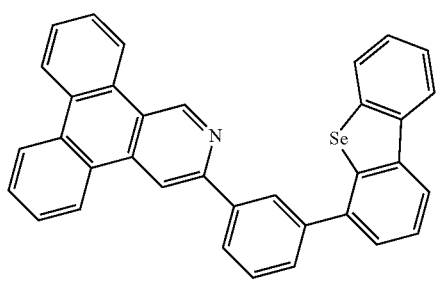
Compound 6
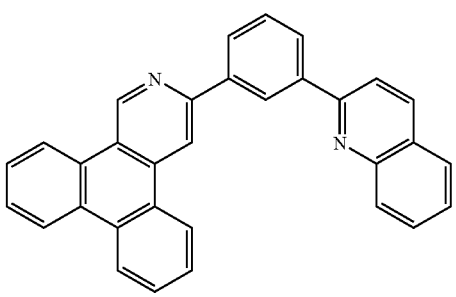
Compound 7
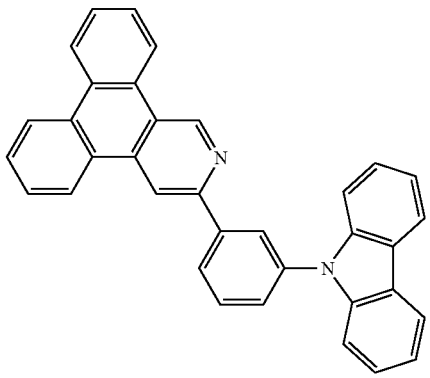
Compound 8
Compound 9
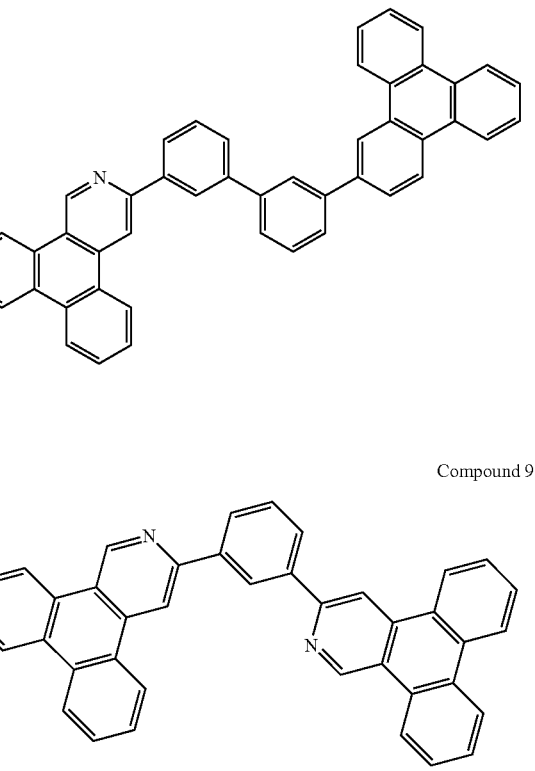

Compound 10
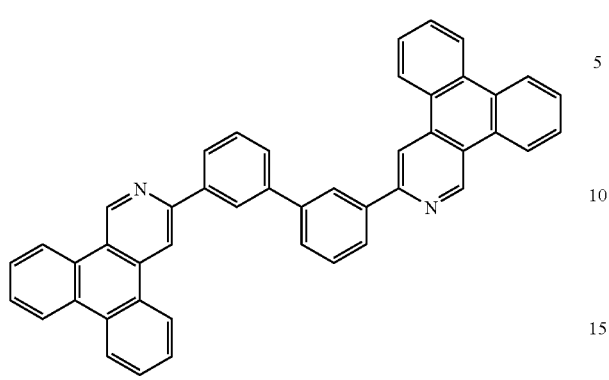
Compound 11
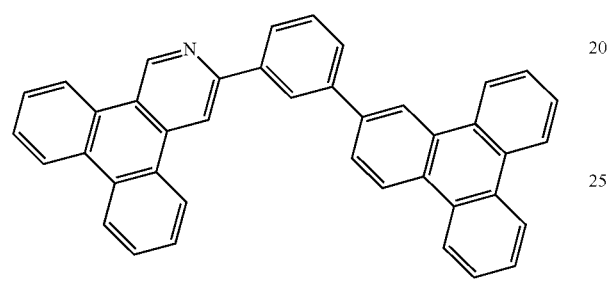
Compound 12
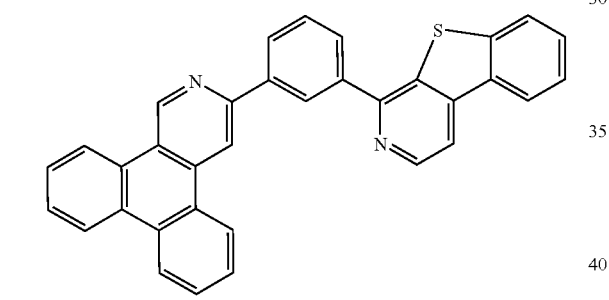
Compound 13
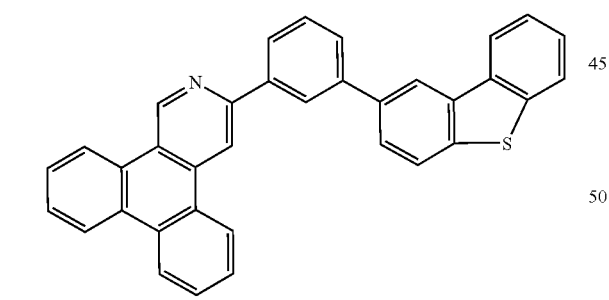
Compound 14
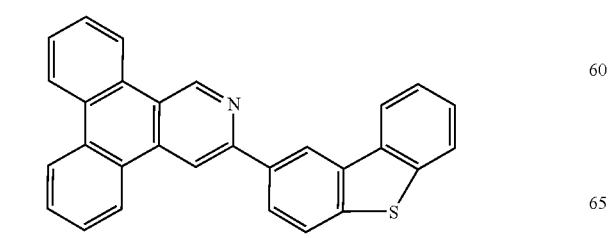
Compound 15
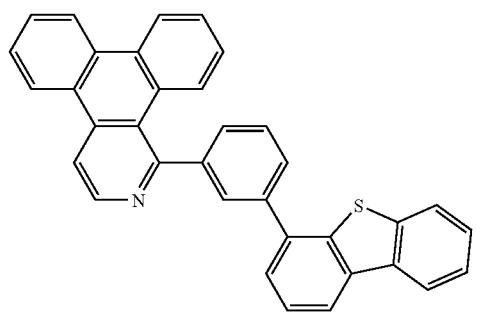
Compound 16
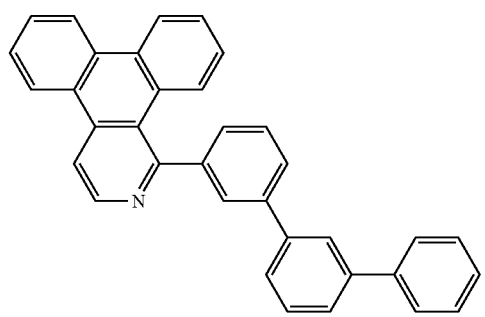
Compound 17
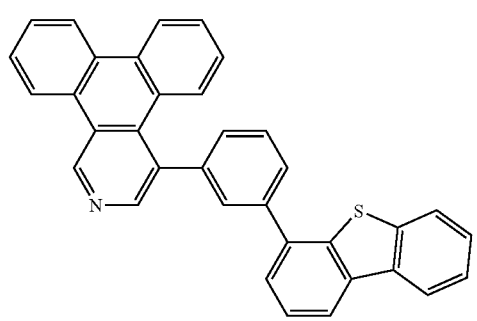
Compound 18
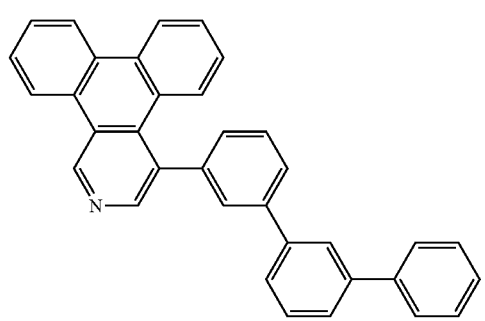

Compound 19
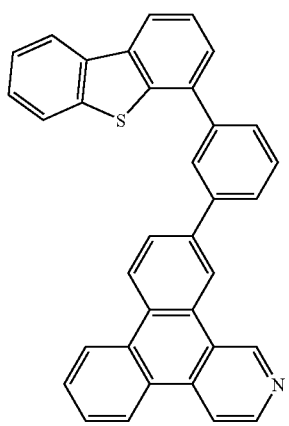
Compound 23
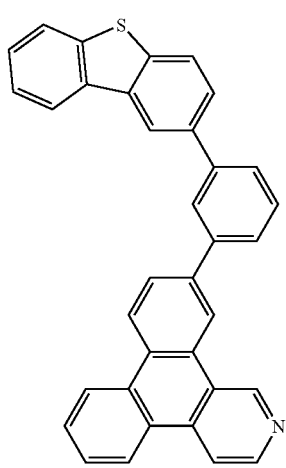
Compound 20
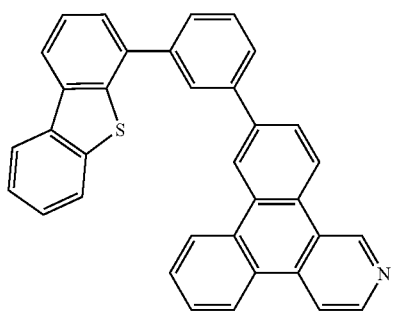
Compound 24
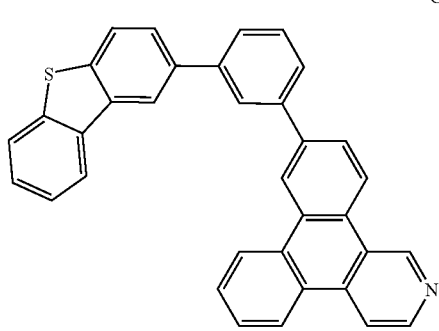
Compound 21
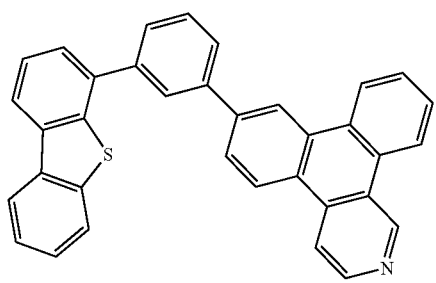
Compound 25
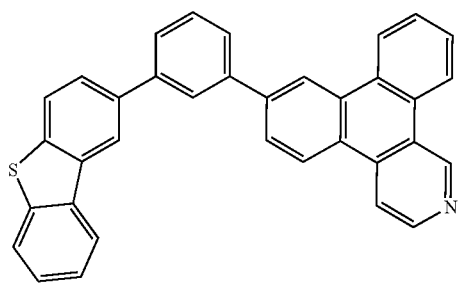
Compound 22
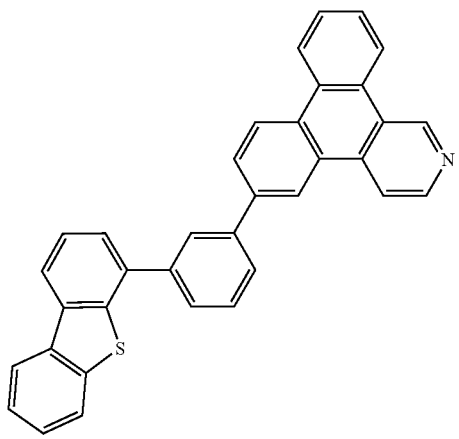
Compound 26
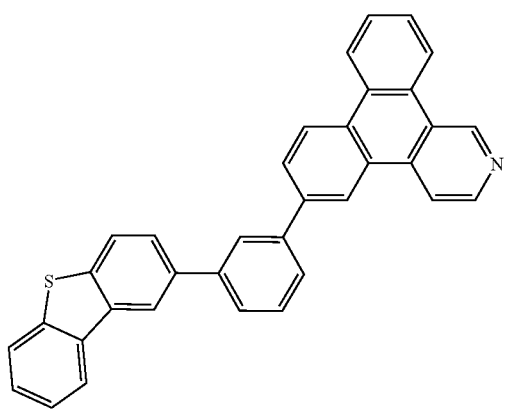

Compound 27
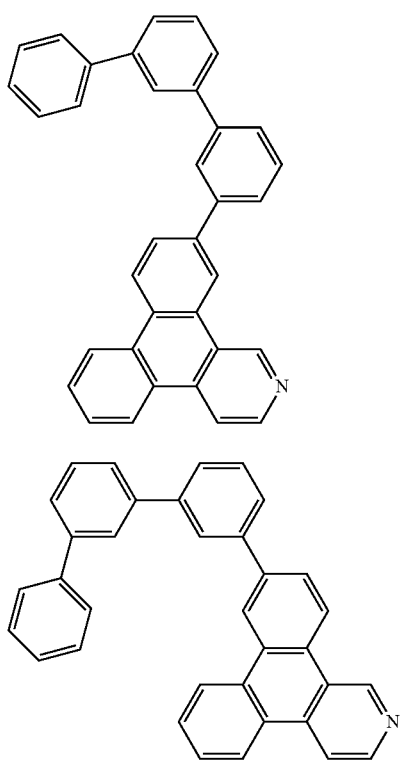
Compound 28
Compound 29
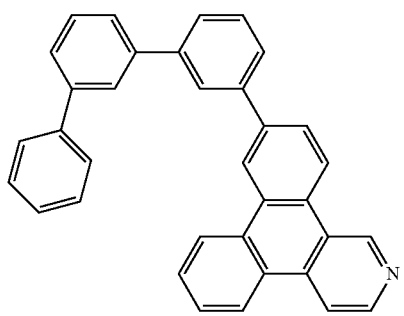
Compound 30
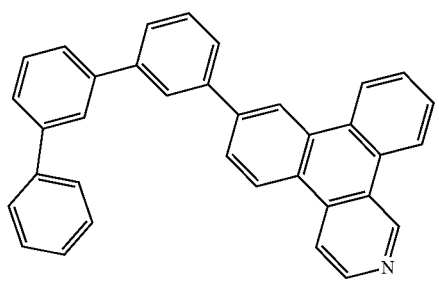
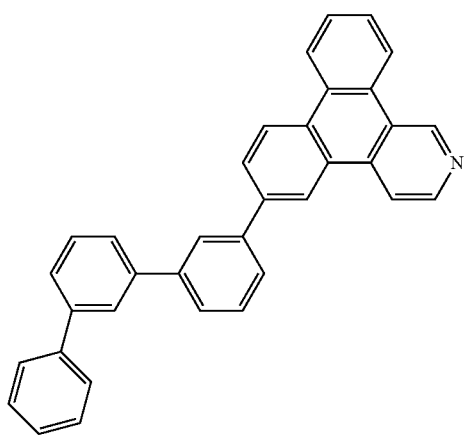
Compound 31
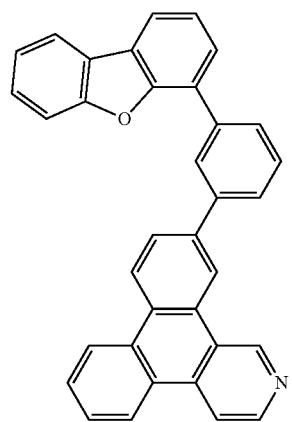
Compound 32
Compound 33
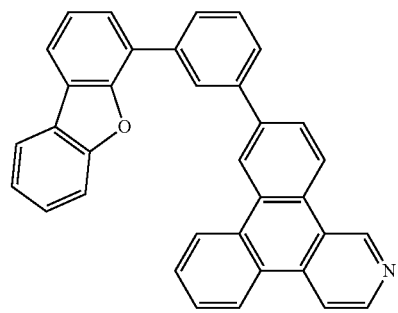
Compound 34
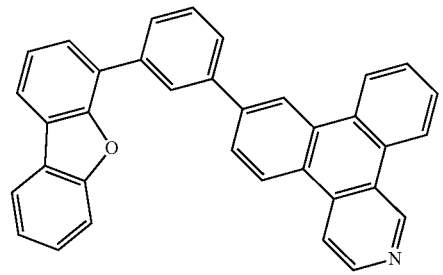
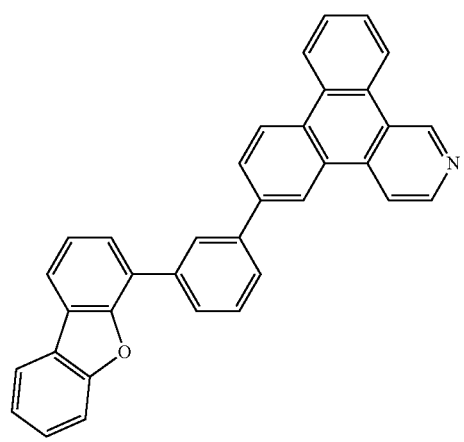

Compound 35
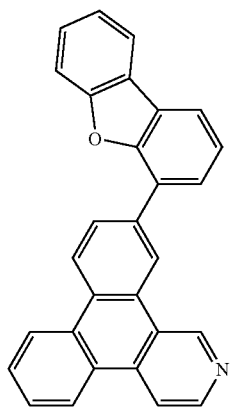
Compound 36
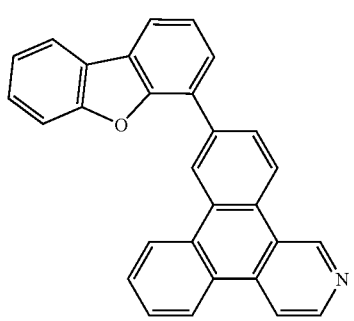
Compound 37
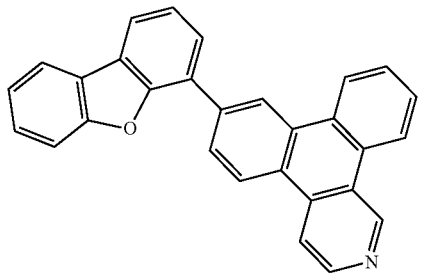
Compound 38
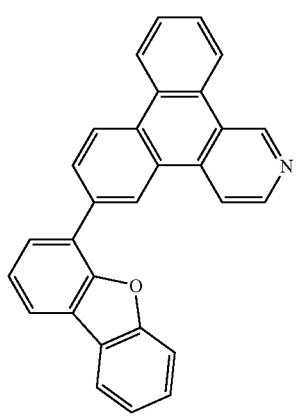
Compound 39
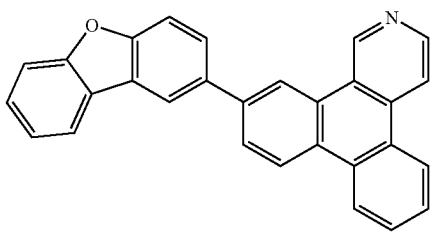
Compound 40
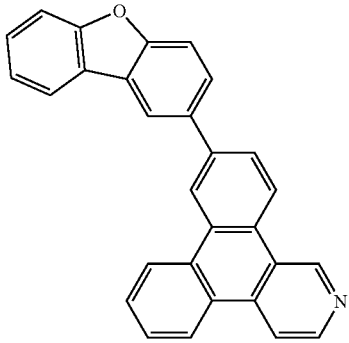
Compound 41
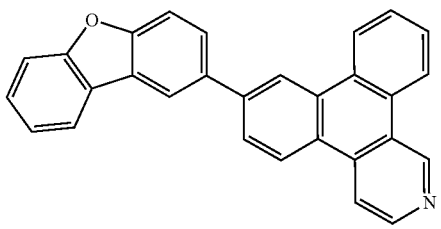
Compound 42
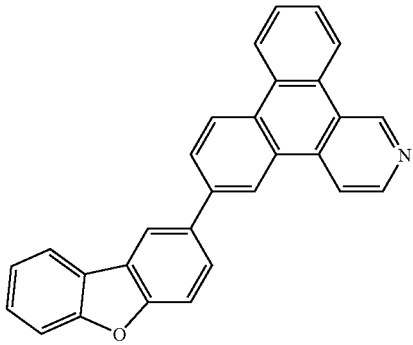
Compound 43
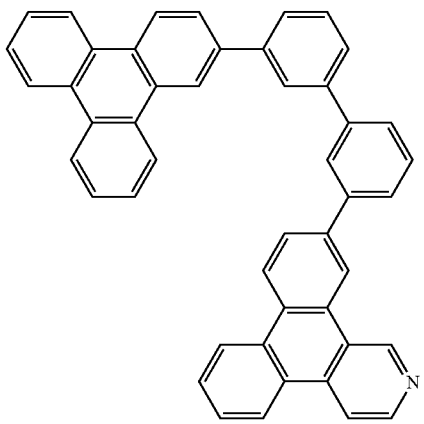

-continued
Compound 44
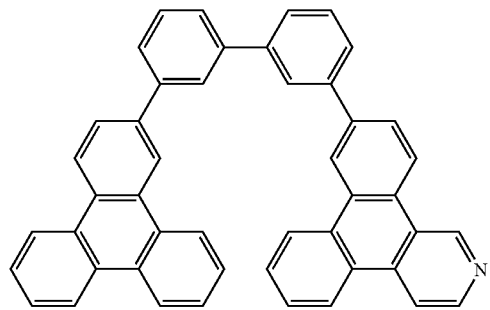
Compound 45
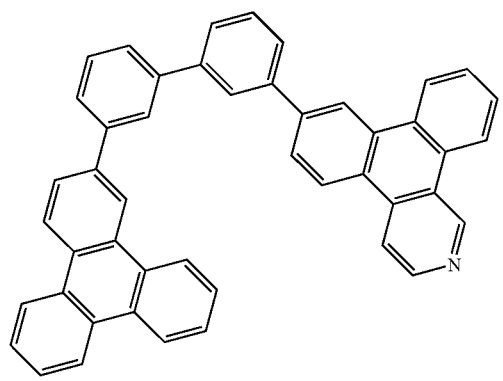
Compound 46
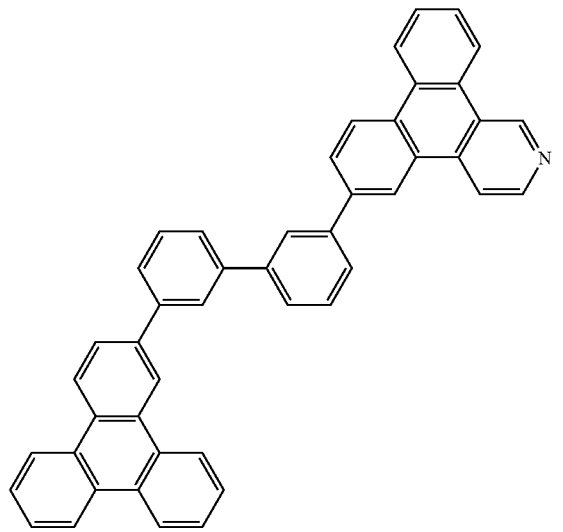
Compound 47
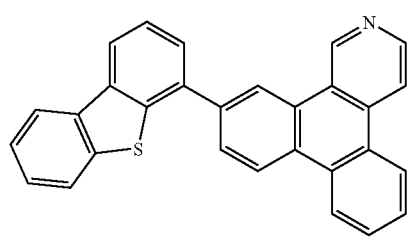
Compound 48
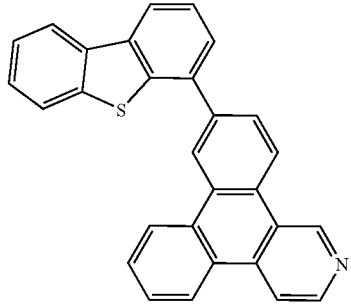
Compound 49
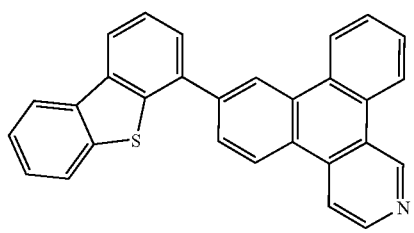
Compound 50
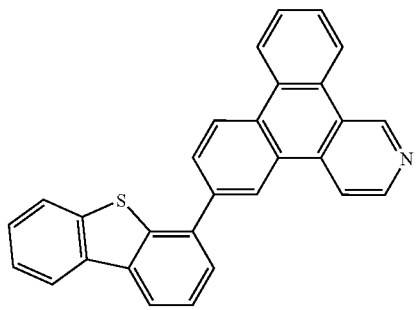
Compound 51
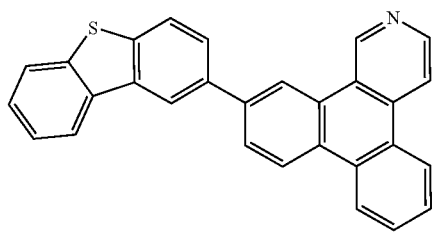
Compound 52
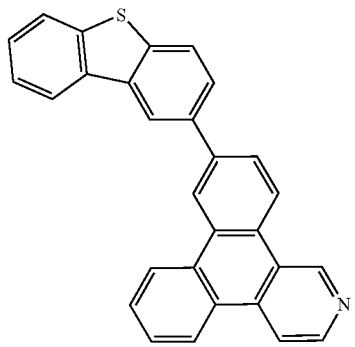

Compound 53
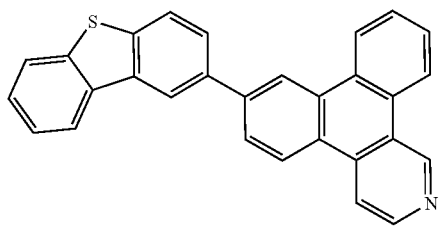
Compound 54
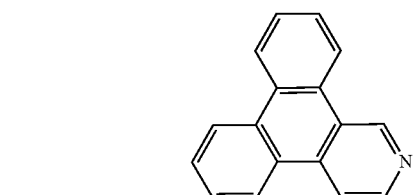
Compound 55
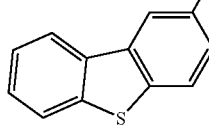
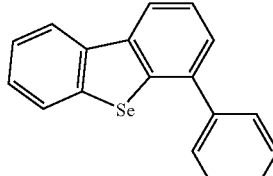
Compound 56
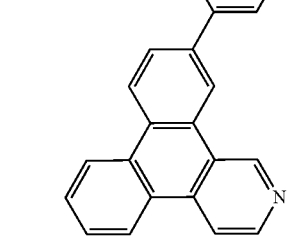
Compound 57
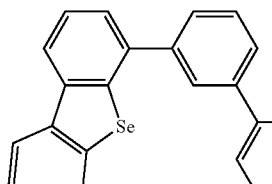
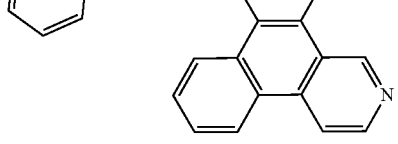
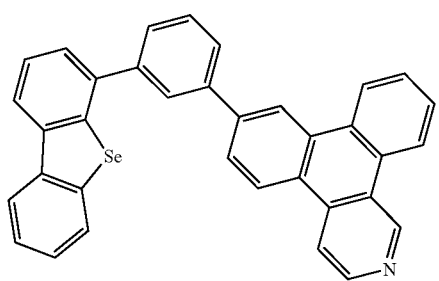
Compound 58
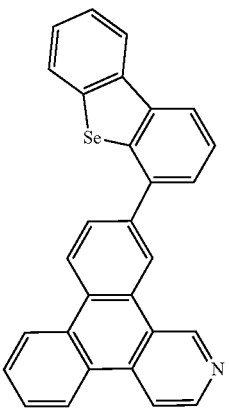
Compound 59
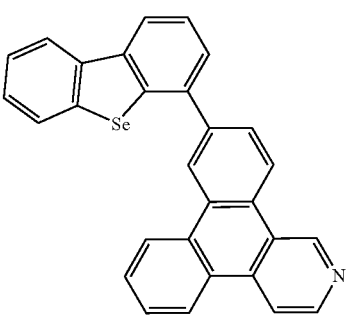
Compound 60
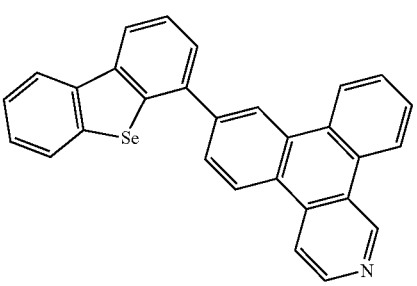
Compound 61

Compound 62
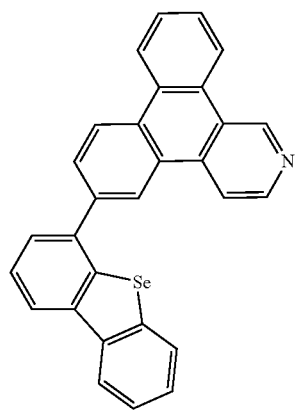
Compound 63
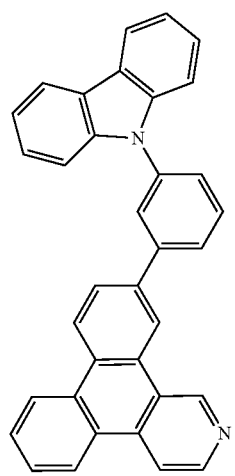
Compound 64
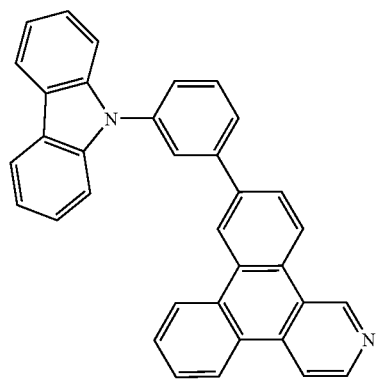
Compound 65
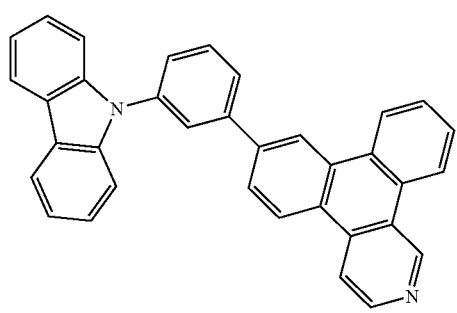
Compound 66
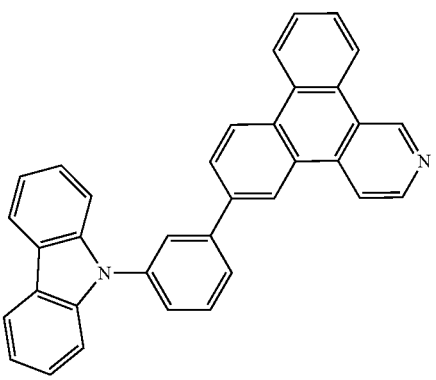
Compound 67
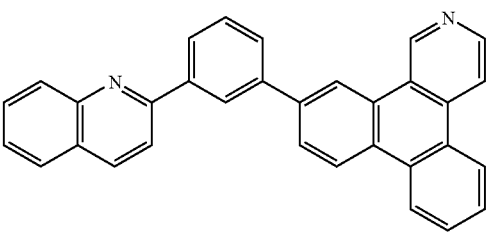
Compound 68
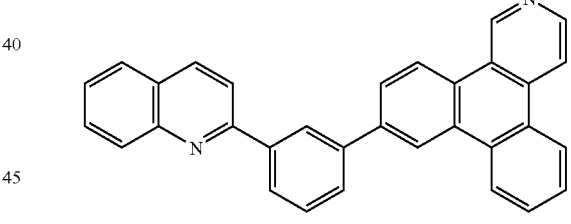
Compound 69
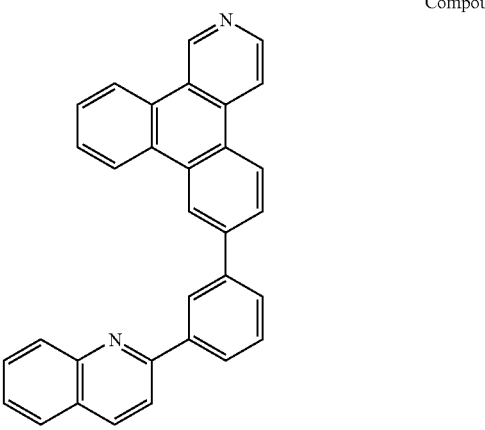

Compound 70

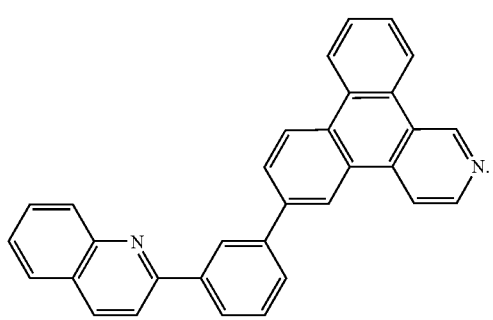

The compounds discussed above (i.e, having the formula of FORMULA I without a coordinated metal) are not phosphorescent at room temperature. These compounds may be used as non-emitting materials in a device. Preferably, these compounds may be used as a host in the emissive layer of an OLED. More preferably, these compounds may be used as a host in the emissive layer of a phosphorescent OLED. These compounds may also be used as materials in a variety of other non-emissive layers within the device structure, such as a hole blocking material within a hole blocking layer.

Another group of novel compounds provided herein are 2-azatriphenylene compounds which comprise a cyclometallated ligand. These compounds may be expected to have emissive properties as a result of the coordinated metal. Preferably, these compounds may be used as emitting materials within the emissive layer of OLEDs. These compounds may also be used an non-emitting materials in other layers of a device that do not require the emissive properties of the compounds. In particular, these compounds may be used as materials in a hole injection or transport layer.

The compounds comprise a ligand L having the formula:

FORMULA II

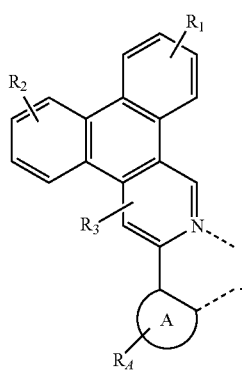

The ligand L contains the 2-azatriphenylene structure, described in FORMULA I, with an aromatic substituent A positioned ortho to the nitrogen atom in the aza ring of the compound.

A is a 5-membered or 6-membered aryl or heteroaryl ring. $R_A$ may represent a mono, di, tri, or tetra substitution. $R_A$ is selected from the group consisting of hydrogen, alkyl, alkoxy, amino, alkenyl, alkynyl, arylkyl, aryl, and heteroaryl. The ligand L is coordinated to a metal having an atomic number greater than 40. Preferably, the metal is Ir.

In one aspect, homoleptic Ir complexes comprising 2-azatriphenylene are provided. In particular, compounds are provided wherein the ligand L is included in a homoleptic compound. In another aspect, heteroleptic Ir complexes are provided. In particular, compounds are provided wherein the ligand L is included in a heteroleptic compound. In yet another aspect, compounds having the formula $(L)_n(L')_{3-n}Ir$ are provided. n is 1 or 2. In one aspect, preferably n is 1. In another aspect, preferably n is 2. L' is selected from the group consisting of:

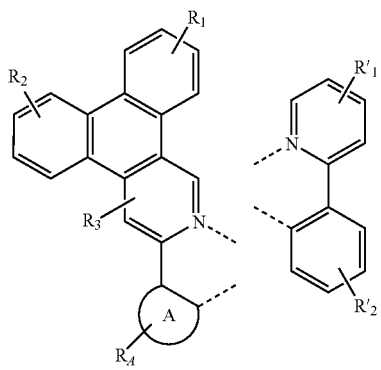

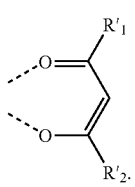

$R'_1$ and $R'_2$ may represent mono, di, tri, or tetra substitutions. $R'_1$ and $R'_2$ are selected from the group consisting of hydrogen, alkyl, alkoxy, amino, alkenyl, alkynyl, arylkyl, aryl, and heteroaryl.

L has a different structure than L'.

Compounds including particular 2-azatriphenylene ligands are provided. The compound containing a ligand L selected from the group consisting of:

Compound 71G

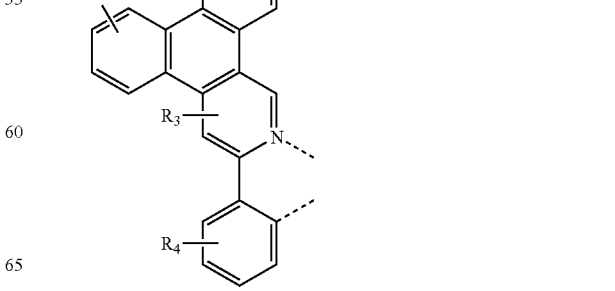

Compound 72G

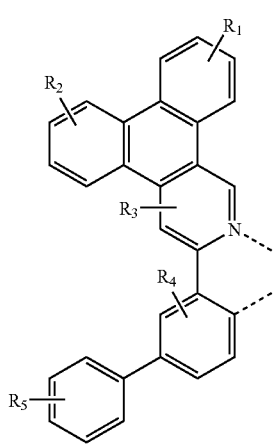

Compound 73G

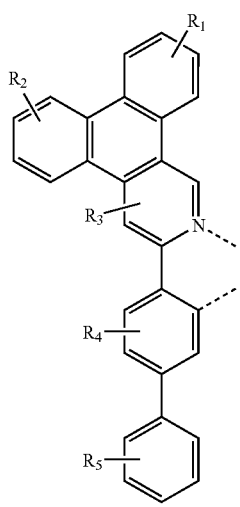

Compound 74G

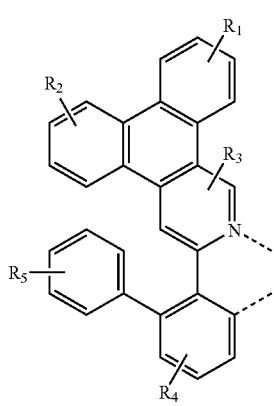

Compound 75G

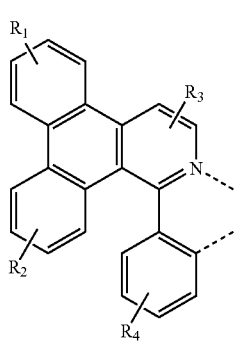

Compound 76G

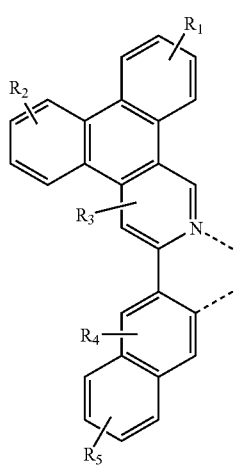

Compound 77G

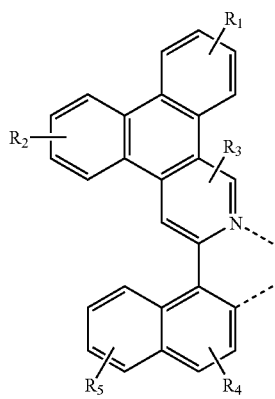

Compound 78G

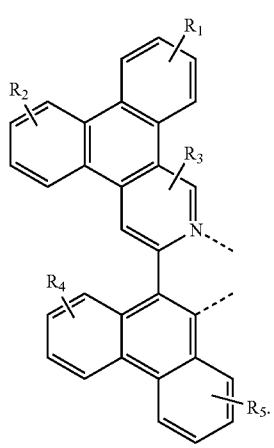

R$_4$ and R$_5$ may represent mono, di, tri, or tetra substitutions. R$_4$ and R$_5$ are selected from the group consisting of hydrogen, alkyl, alkoxy, amino, alkenyl, alkynyl, arylkyl, aryl, and heteroaryl.

In addition, compounds containing a specific 2-azatriphenylene ligand are provided. The ligand L is selected from the group consisting of:

Compound 71
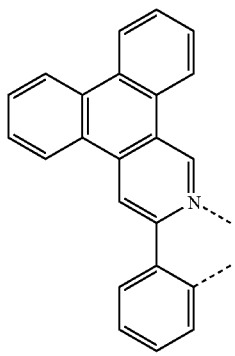
Compound 72
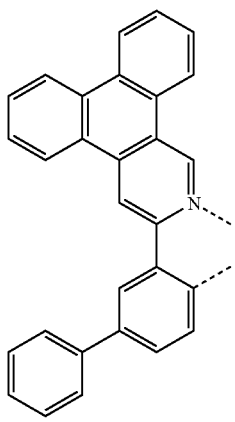
Compound 73
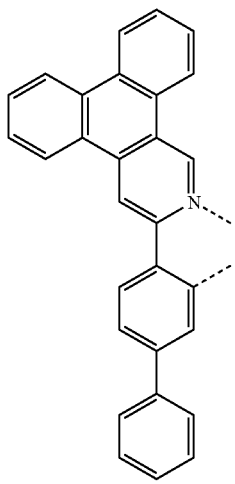
Compound 74
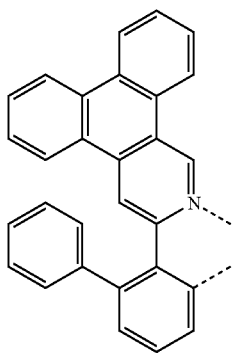
Compound 75
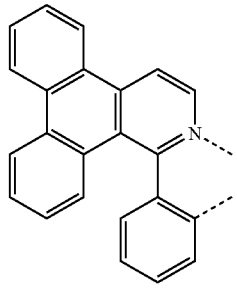
Compound 75'
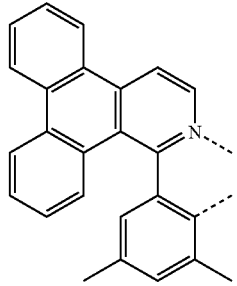
Compound 76
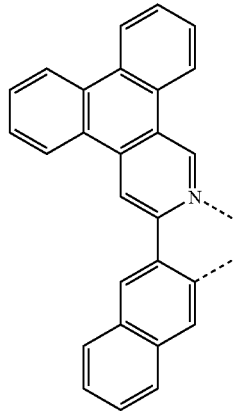
Compound 77
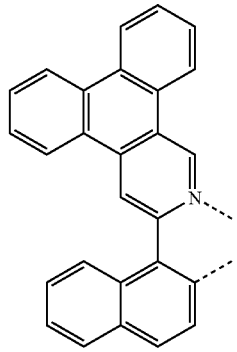

Compound 78
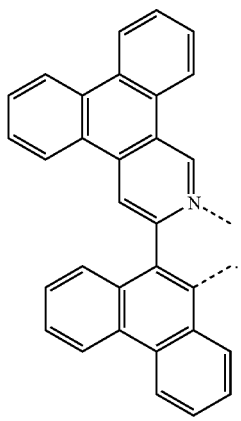
Particular compounds comprising an Ir complex containing a 2-azatriphenylene ligand are provided, including compounds selected from the group consisting of:
Compound 79
Compound 80
Compound 81
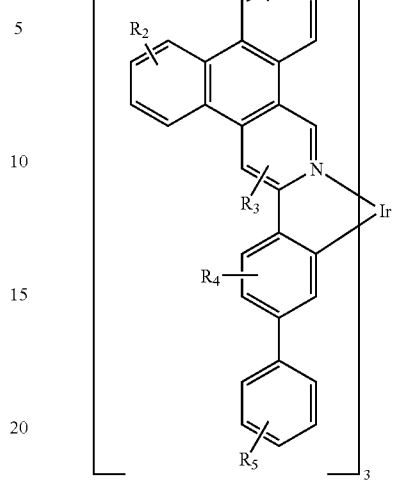
Compound 82
Compound 83
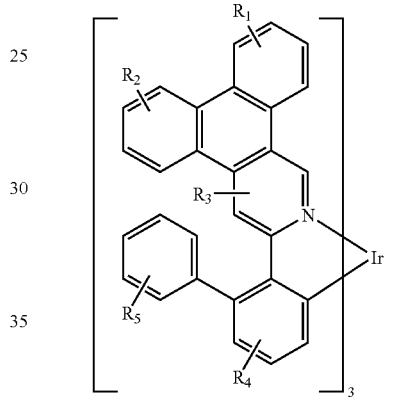
Compound 84
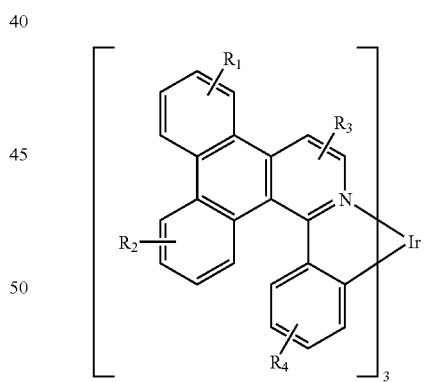
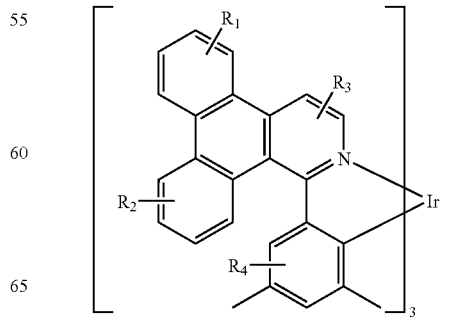

Compound 85
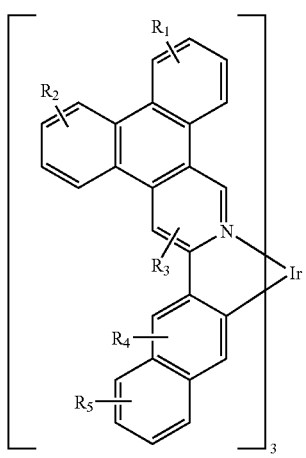
Compound 86
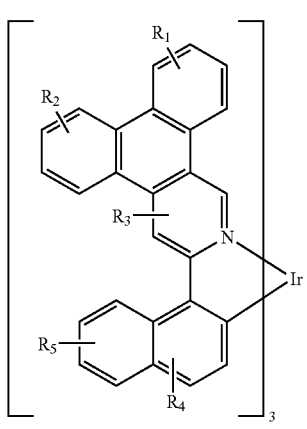
Compound 87
Compound 88
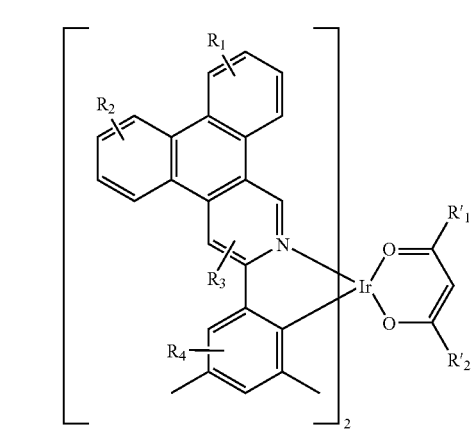
Compound 89
Compound 90
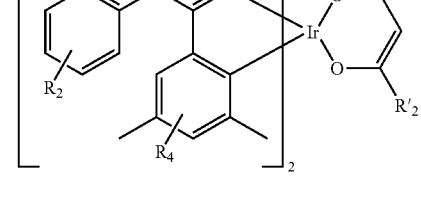
Compound 91
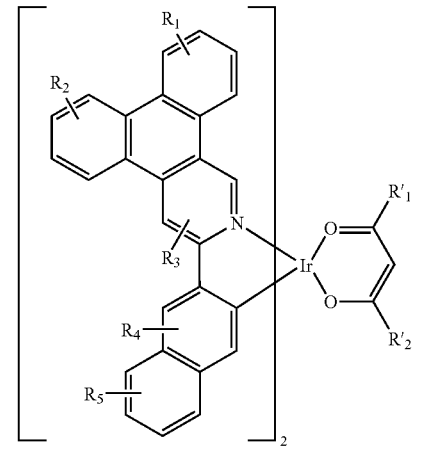

Compound 92

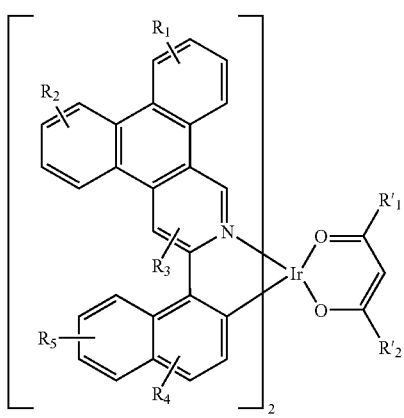

Compound 93

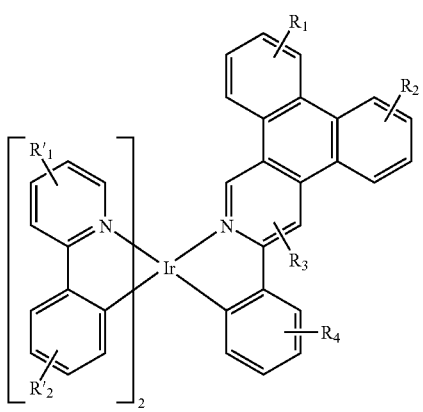

Compound 94

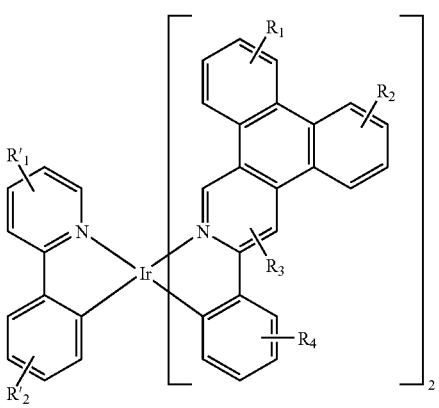

Compound 95

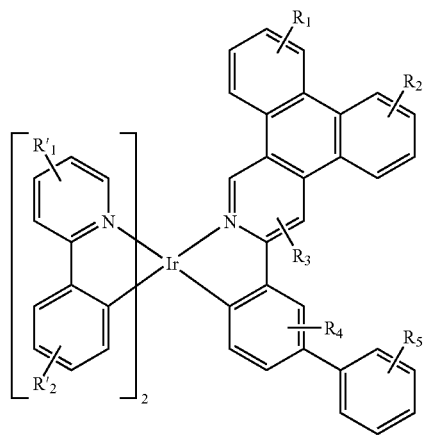

Compound 96

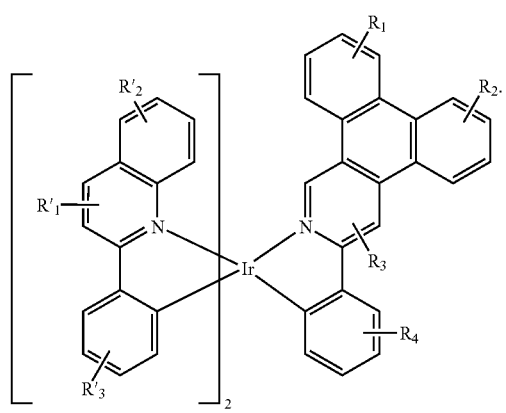

$R_4$, $R_5$, $R'_1$, and $R'_2$ may represent mono, di, tri, tetra, or penta substitutions. $R_4$, $R_5$, $R'_1$, and $R'_2$ are independently selected from the group consisting of hydrogen, alkyl, alkoxy, amino, alkenyl, alkynyl, arylkyl, aryl, and heteroaryl.

In addition, specific iridium complexes containing 2-azatriphenylene are also provided, including compounds selected from the group consisting of:

Compound 79

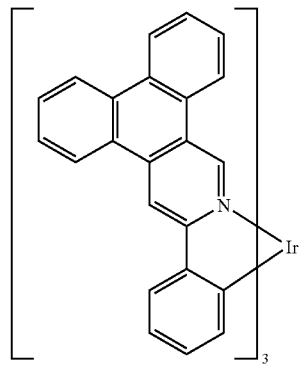

Compound 80
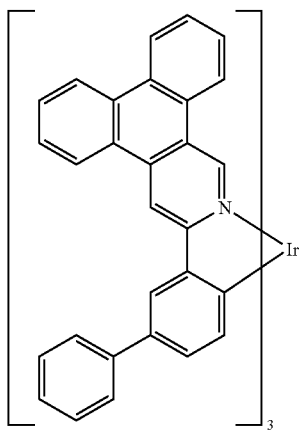
Compoung 81
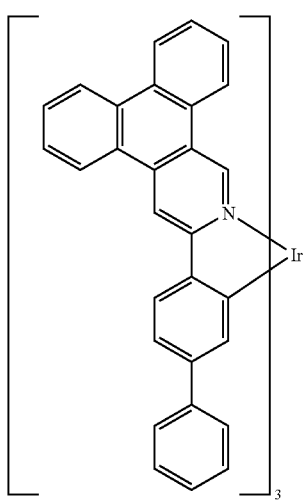
Compound 82
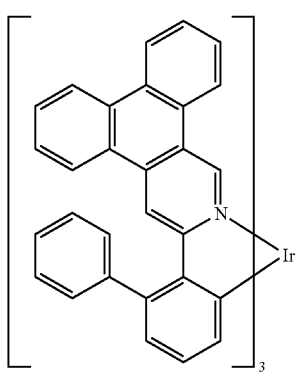
Compound 83
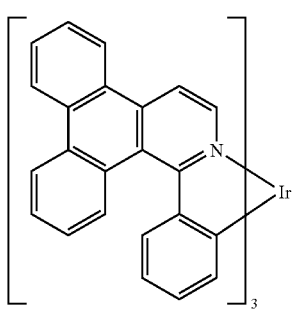
Compound 84
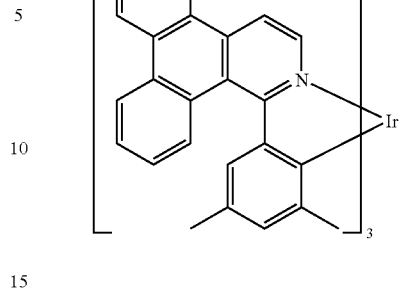
Compound 85
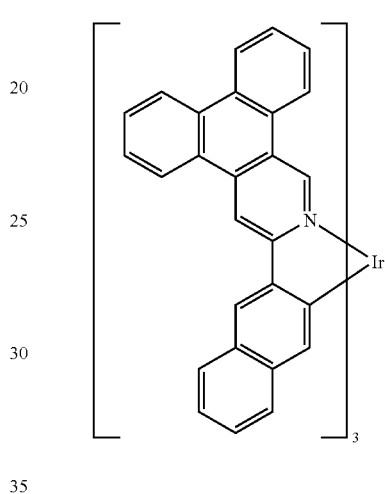
Compound 86
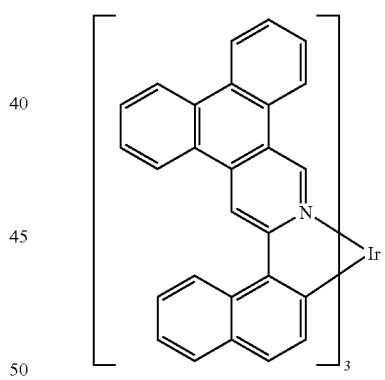
Compound 87
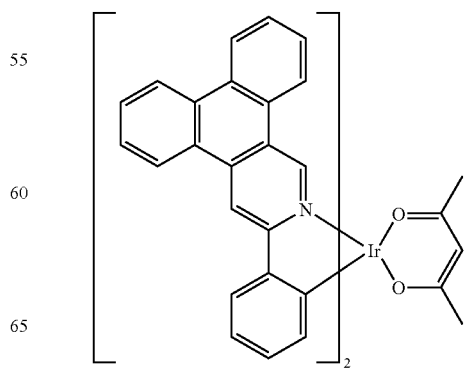

Compound 88
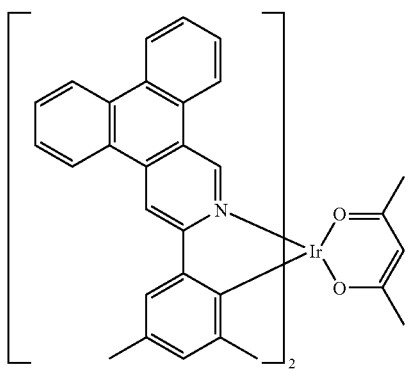
Compound 89
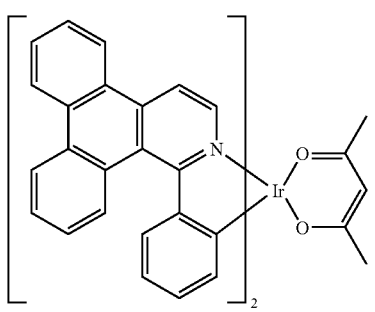
Compound 90
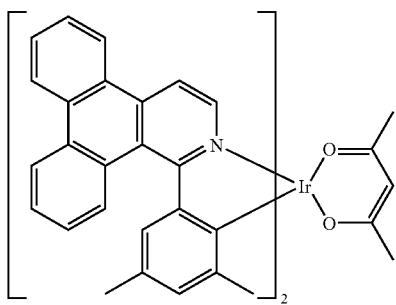
Compound 91
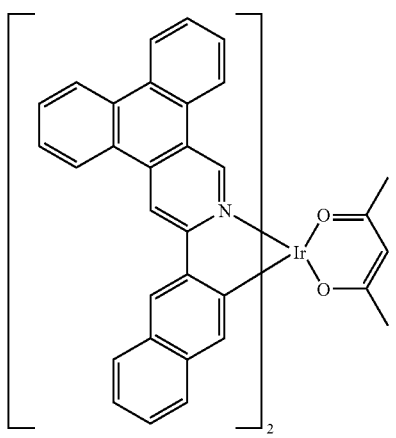
Compound 92
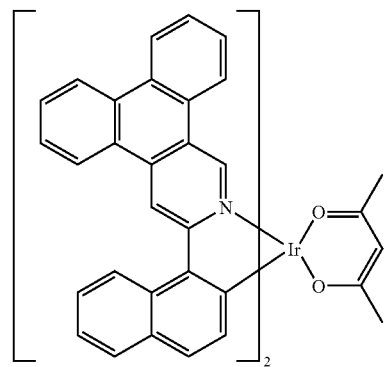
Compound 93
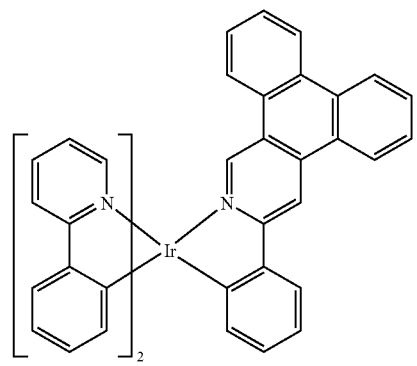
Compound 94
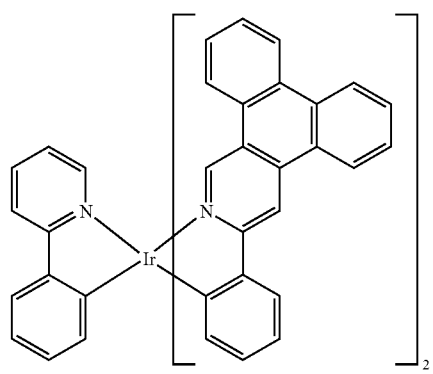
Compound 95
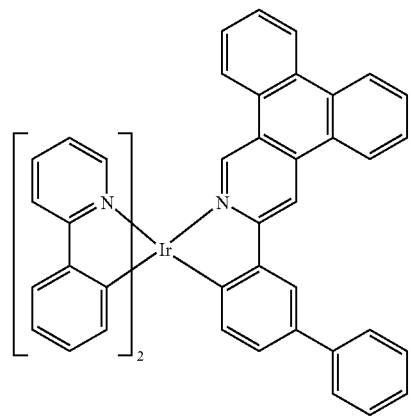

Compound 96

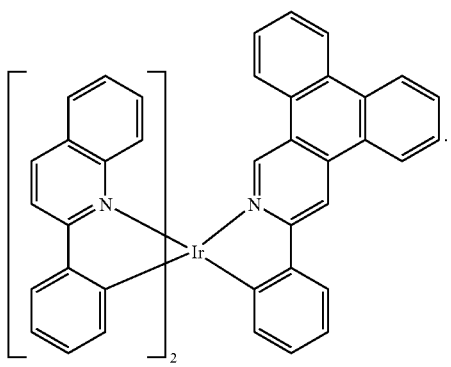

An organic light emitting device is also provided. The device comprises an anode, a cathode, and a first organic emissive layer disposed between the anode and the cathode. The first organic emissive layer comprises a compound including the structure FORMULA I, as discussed above. Selections for the substituents described as preferred for the compounds including the structure FORMULA I are also preferred for use in a device that comprises a compound including the structure FORMULA I. These selections include those described for $R_1$, $R_2$, $R_3$, and A.

$R_1$, $R_2$, and $R_3$ may represent mono, di, tri, or tetra substitution. $R_1$, $R_2$, and $R_3$ are independently selected from the group consisting of hydrogen, alkyl, alkoxy, amino, alkenyl, alkynyl, aryl, and heteroaryl. At least one of $R_1$, $R_2$, and $R_3$ is an aryl or heteroaryl.

In one aspect, devices are provided which contain a compound wherein $R_1$ is selected from the group consisting of alkyl, alkoxy, amino, alkenyl, alkynyl, aryl, and heteroaryl. Preferably, $R_1$ is an aryl or a heteroaryl. In another aspect, devices are provided which contain a compound wherein $R_2$ is selected from the group consisting of alkyl, alkoxy, amino, alkenyl, alkynyl, aryl, and heteroaryl. Preferably, $R_2$ is an aryl or a heteroaryl. In yet another aspect, devices are provided which contain a compound wherein $R_3$ is selected from the group consisting of alkyl, alkoxy, amino, alkenyl, alkynyl, aryl, and heteroaryl. Preferably, $R_3$ is an aryl or a heteroaryl. In a further aspect, devices are provided which contain a compound wherein $R_1$, $R_2$, and $R_3$ are an aryl or a heteroaryl.

Devices are provided wherein the device includes a compound having the formula:

FORMULA I

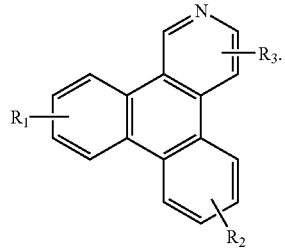

The compound is not coordinated to a metal.

Particular devices are provided, the device comprising a compound selected from the group consisting of Compound 1G-Compound 70G. $R'_3$, $R_4$, $R_5$, $R_6$, $R_7$, and $R_8$ may represent mono, di, tri, tetra, or penta substitutions. $R'_3$, $R_4$, $R_5$, $R_6$, $R_7$, and $R_8$ are independently selected from the group consisting of hydrogen, alkyl, alkoxy, amino, alkenyl, alkynyl, arylkyl, aryl and heteroaryl. Certain devices are provided which may contain a compound selected from the group consisting of Compound 1-Compound 70 (i.e., $R_1$, $R_2$, $R_3$, $R_4$, $R_5$, $R_6$, $R_7$, and $R_8$ are hydrogen).

Preferably, $R_3$ is a substitution ortho to the nitrogen.

Additionally, devices are provided wherein the first organic layer is an emissive layer and the compound including the structure FORMULA I is a host. Moreover, the first organic layer of such a device may further comprise an emitting dopant. In particular, the first organic layer may comprise an emitting dopant having the formula:

E1

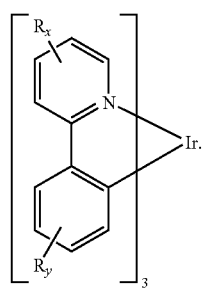

$R_x$ and $R_y$ may represent mono, di, tri, or tetra substitutions. $R_x$ and $R_y$ are independently selected from the group consisting of hydrogen, alkyl, and aryl.

Additionally, devices are also provided wherein the first organic layer is an emissive layer and the compound including the structure FORMULA II is an emitting dopant. Moreover, the first organic layer of such a device may further comprise a host material.

Moreover, devices are also provided wherein the device comprises a second organic layer that is a non-emissive layer and the compound including the structure FORMULA II is a non-emissive material in the second organic layer. Preferably, the second organic layer is a hole injection or transport layer and the compound including the structure FORMULA II is a hole injection or transport material.

In another aspect, devices are provided wherein the device includes a compound comprising a ligand L having the formula:

FORMULA II

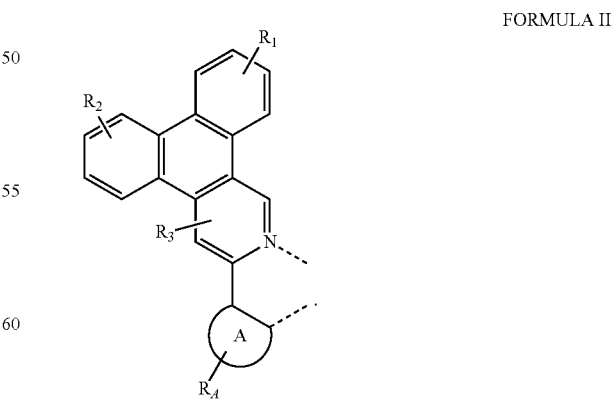

A is a 5-membered or 6-membered aryl or heteroaryl ring. $R_4$ may represent a mono, di, tri, or tetra substitution. $R_4$ is selected from the group consisting of hydrogen, alkyl, alkoxy, amino, alkenyl, alkynyl, arylkyl, aryl, and heteroaryl. The ligand L is coordinated to a metal having an atomic number greater than 40. Preferably, the metal is Ir.
Particular devices are provided wherein the ligand L is selected from the group consisting of:
Compound 71G
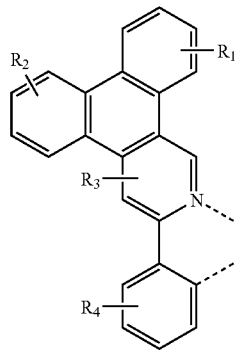
Compound 72G
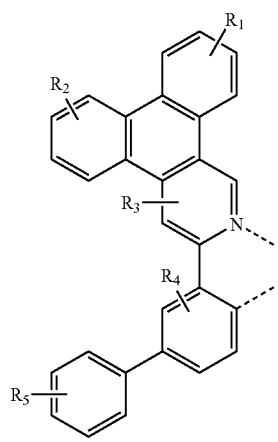
Compound 73G
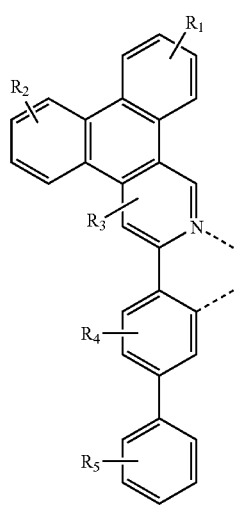
-continued
Compound 74G
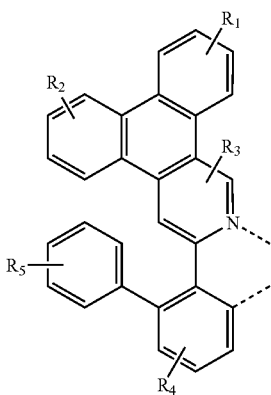
Compound 75G
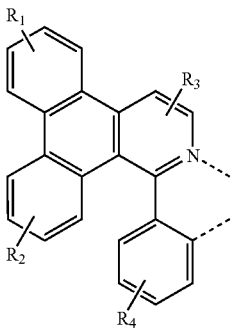
Compound 76G
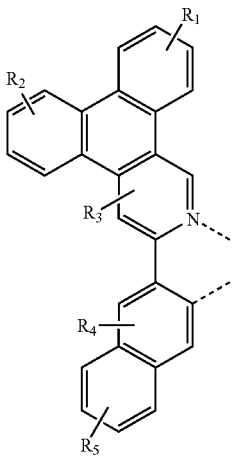
Compound 77G
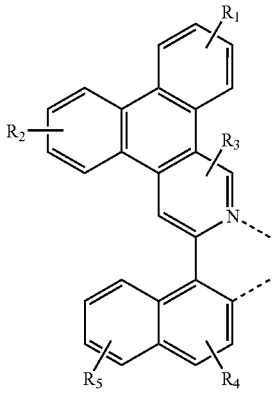

Compound 78G

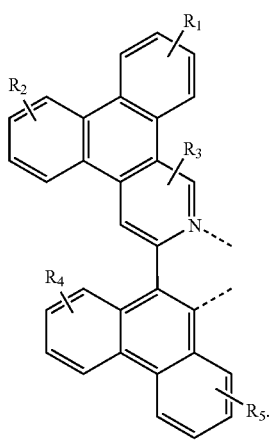

R₄ and R₅ may represent mono, di, tri, tetra, or penta substitutions. R₄ and R₅ are independently selected from hydrogen, alkyl, alkoxy, amino, alkenyl, alkynyl, aryl and heteroaryl.

Devices containing a compound comprising a ligand selected from the group consisting of Compound 71-Compound 78 are also provided.

Devices containing a compound comprising an Ir complex containing a 2-azatriphenylene ligand are also provided, including devices containing a compound selected from the group consisting of Compound 79G-Compound 96G. Devices containing a specific compound are also provided, including devices containing a compound selected from the group consisting of Compound 79-Compound 96.

Additionally, a consumer product comprising a device is also provided. The device further comprises an anode, a cathode, and a first organic layer disposed between the anode and the cathode. The first organic layer further comprises a compound that includes the structure FORMULA I, as described above. Selections for the substituents described as preferred for compounds having FORMULA I are also preferred for use in a device that includes a compound including the structure FORMULA I. These selections include those described for $R_1$, $R_2$, $R_3$, $R_4$, $R_5$, $R_6$, $R_7$, $R_8$, $R'_1$, $R'_2$, and A.

$R_1$, $R_2$, and $R_3$ may represent mono, di, tri, or tetra substitution. $R_1$, $R_2$, and $R_3$ are independently selected from the group consisting of hydrogen, alkyl, alkoxy, amino, alkenyl, alkynyl, aryl, and heteroaryl. At least one of $R_1$, $R_2$, and $R_3$ is an aryl or heteroaryl.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 2 below. Table 2 lists non-limiting classes of materials, non-limiting examples of compounds for each class, and references that disclose the materials.

TABLE 2

| MATERIAL | EXAMPLES OF MATERIAL | PUBLICATIONS |
|---|---|---|
| Hole injection materials | | |
| Phthalocyanine and porphryin compounds | | Appl. Phys. Lett. 69, 2160 (1996) |

TABLE 2-continued

| MATERIAL | EXAMPLES OF MATERIAL | PUBLICATIONS |
|---|---|---|
| Starburst triarylamines | 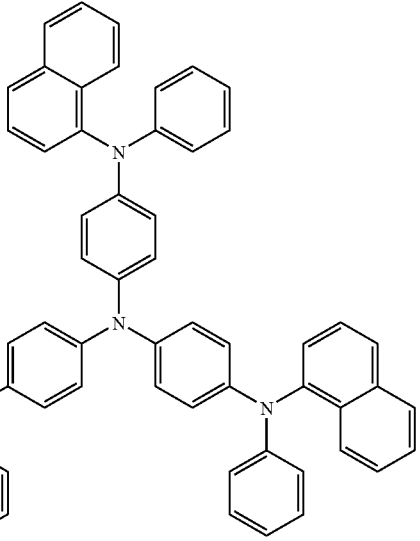 | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | 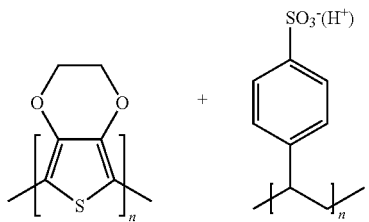 | Synth. Met. 87, 171 (1997) |
| Arylamines complexed with metal oxides such as molybdenum and tungsten oxides | 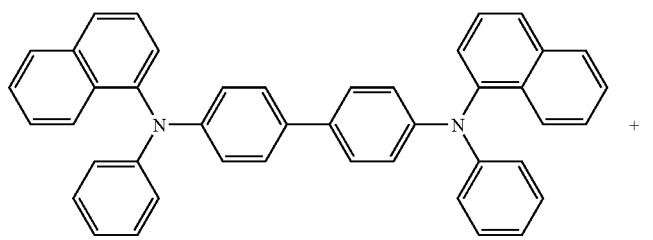 | SID Symposium Digest, 37, 923 (2006) |

Hole transporting materials

| | | |
|---|---|---|
| Triarylamines (e.g., TPD, α-NPD) | 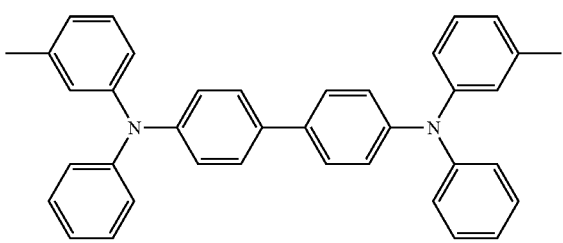 | Appl. Phys. Lett. 51, 913 (1987) |

TABLE 2-continued

| MATERIAL | EXAMPLES OF MATERIAL | PUBLICATIONS |
|---|---|---|
| | | US5061569 |
| | | EP650955 |
| | | J. Mater. Chem. 3, 319 (1993) |

TABLE 2-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |

TABLE 2-continued

| MATERIAL | EXAMPLES OF MATERIAL | PUBLICATIONS |
| --- | --- | --- |
| Arylamine carbazole compounds | | Adv. Mater. 6, 677 (1994) |
| Indolocarbazoles | | Synth. Met. 111, 421 (2000) |
| Isoindole compounds | | Chem. Mater. 15, 3148 (2003) |

TABLE 2-continued

| MATERIAL | EXAMPLES OF MATERIAL | PUBLICATIONS |
|---|---|---|
| Phosphorescent OLED host materials | | |
| Red hosts | | |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE 2-continued
| MATERIAL | EXAMPLES OF MATERIAL | PUBLICATIONS |
|---|---|---|
| Green hosts | | |
| Arylcarbazoles | 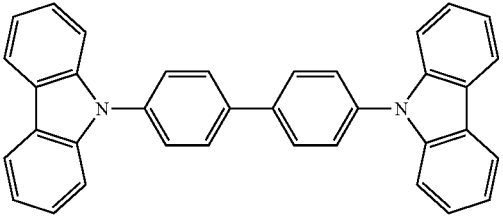 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 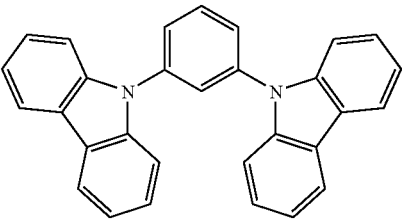 [SMILES: c1cc(-n2c3ccccc3c3ccccc32)cc(-n2c3ccccc3c3ccccc32)c1] | US2003175553 |
| | 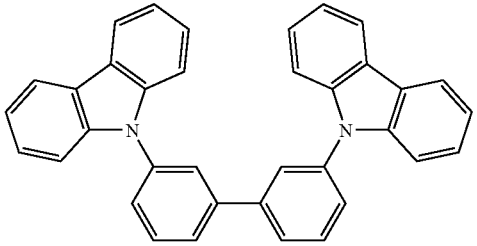 [SMILES: c1cc(-c2cccc(-n3c4ccccc4c4ccccc43)c2)cc(-n2c3ccccc3c3ccccc32)c1] | WO2001039234 |
| Aryltriphenylene compounds | 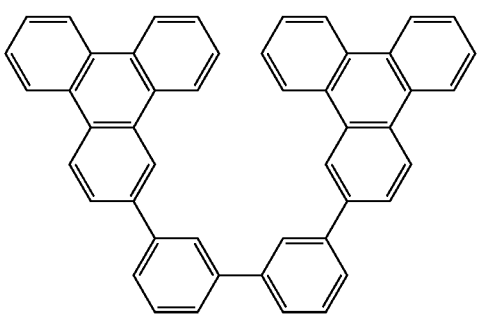 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 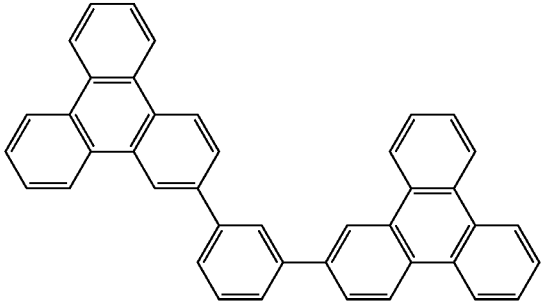 [SMILES: c1cc(-c2ccc3c4ccccc4c4ccccc4c3c2)cc(-c2ccc3c4ccccc4c4ccccc4c3c2)c1] | US20060280965 |
| Polymers (e.g., PVK) | 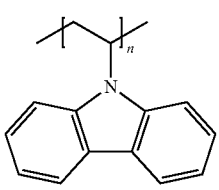 | Appl. Phys. Lett. 77, 2280 (2000) |

TABLE 2-continued

| MATERIAL | EXAMPLES OF MATERIAL | PUBLICATIONS |
|---|---|---|
| Spirofluorene compounds | | WO2004093207 |
| Metal phenoxybenzooxazole compounds | | WO05089025 |
| | | WO06132173 |
| | | JP200511610 |
| Spirofluorene-carbazole compounds | | JP2007254297 |

TABLE 2-continued
| MATERIAL | EXAMPLES OF MATERIAL | PUBLICATIONS |
|---|---|---|
| | 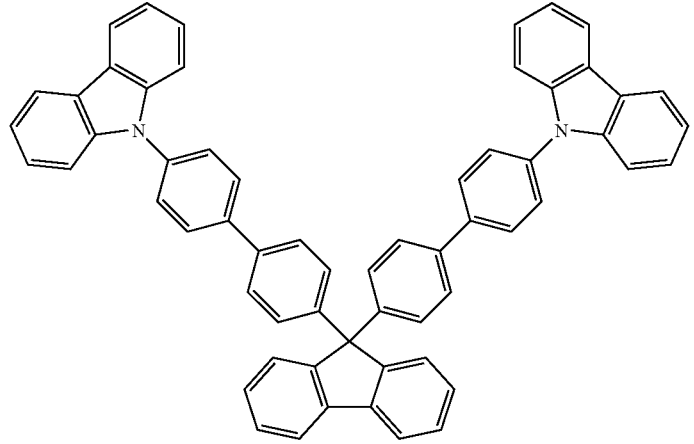 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 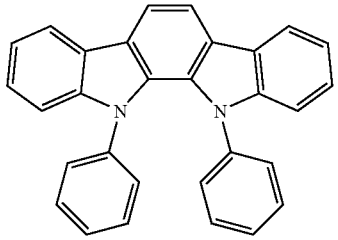 [SMILES: c1ccc(-n2c3ccccc3c3ccc4c5ccccc5n(-c5ccccc5)c4c32)cc1] | WO07063796 |
| | 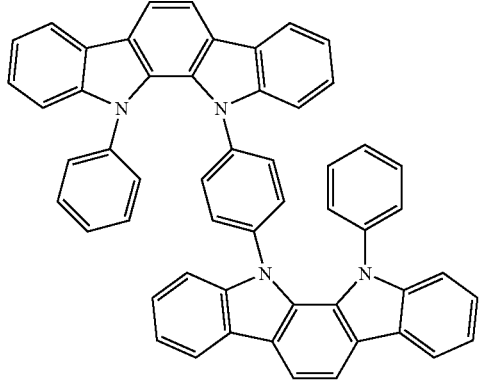 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO07063754 |
| 5-member ring electron deficient heterocycles (e.g., triazole, oxadiazole) | 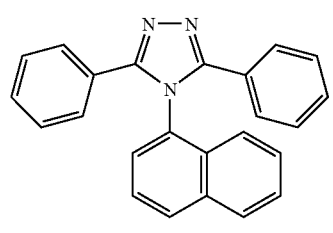 [SMILES: c1ccc(-c2nnc(-c3ccccc3)n2-c2cccc3ccccc23)cc1] | J. Appl. Phys. 90, 5048 (2001) |
| | 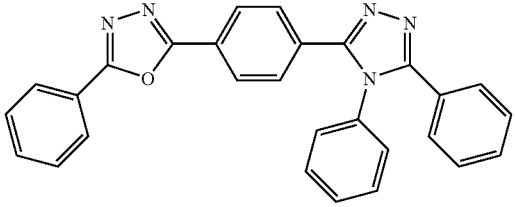 [SMILES: c1ccc(-c2nnc(-c3ccc(-c4nnc(-c5ccccc5)n4-c4ccccc4)cc3)o2)cc1] | WO04107822 |

TABLE 2-continued

| MATERIAL | EXAMPLES OF MATERIAL | PUBLICATIONS |
|---|---|---|
| Metal phenoxypyridine compounds | | WO05030900 |
| Blue hosts | | |
| Arylcarbazoles | | Appl. Phys. Lett, 82, 2422 (2003) |
| | | US20070190359 |
| Dibenzothiophene-carbazole compounds | | WO2006114966 |
| Phosphorescent dopants | | |
| Red dopants | | |
| Heavy metal porphyrins (e.g., PtOEP) | | Nature 395, 151 (1998) |

TABLE 2-continued

| MATERIAL | EXAMPLES OF MATERIAL | PUBLICATIONS |
|---|---|---|
| Iridium(III) organometallic complexes | | Appl. Phys. Lett. 78, 1622 (2001) |
| | | US06835469 |
| | | US06835469 |
| | | US20060202194 |
| | | US20060202194 |

TABLE 2-continued

| MATERIAL | EXAMPLES OF MATERIAL | PUBLI-CATIONS |
|---|---|---|
| | [Ir complex with methyl-substituted benzoquinoline ligand]₃ | US07087321 |
| | [Ir complex with phenyl-isoquinoline ligand]₃ | US07087321 |
| | [Ir complex with octyl-substituted phenyl-isoquinoline ligand, $H_{17}C_8$]₃ | Adv. Mater. 19, 739 (2007) |
| Platinum(II) organometallic complexes | Pt complex with phenyl-isoquinoline and acetylacetonate ligands | WO2003040257 |
| Osminum(III) complexes | [Os(PPhMe₂)₂ complex with $F_3C$-pyrazolyl-pyridine ligand]₂ | Chem. Mater. 17, 3532 (2005) |
| Ruthenium(II) complexes | [Ru(PPhMe₂)₂ complex with $^tBu$-pyrazolyl-isoquinoline ligand]₂ | Adv. Mater. 17, 1059 (2005) |

TABLE 2-continued
| MATERIAL | EXAMPLES OF MATERIAL | PUBLICATIONS |
|---|---|---|
| Green dopants | | |
| Iridium(III) organometallic complexes | 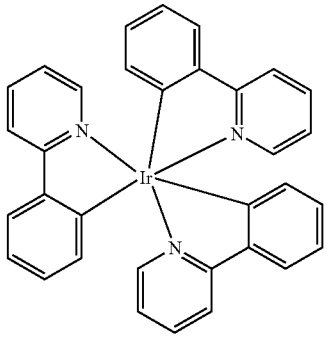<br>and its derivatives | Inorg. Chem. 40, 1704 (2001) |
| | 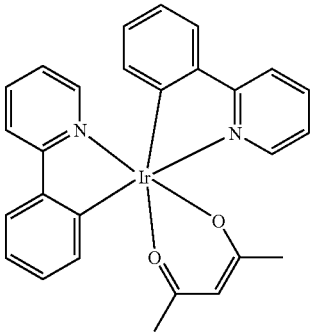 | US2002034656 |
| | 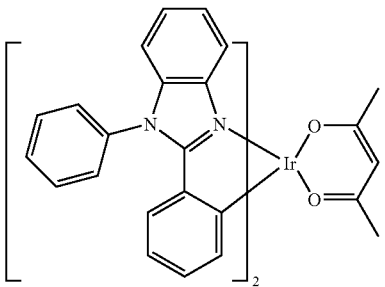 | US06687266 |
| | 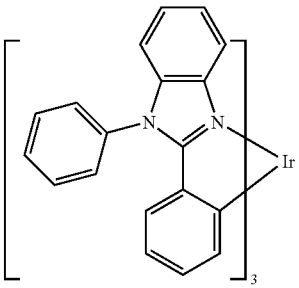 | Chem. Mater. 16, 2480 (2004) |

TABLE 2-continued

| MATERIAL | EXAMPLES OF MATERIAL | PUBLICATIONS |
|---|---|---|
| | | US2007190359 |
| | | US 2006008670 JP2007123392 |
| | | Adv. Mater. 16, 2003 (2004) |
| | | Angew. Chem. Int. Ed. 2006, 45, 7800 |
| Pt(II) organometallic complexes | | Appl. Phys. Lett. 86, 153505 (2005) |

TABLE 2-continued
| MATERIAL | EXAMPLES OF MATERIAL | PUBLICATIONS |
|---|---|---|
|  | 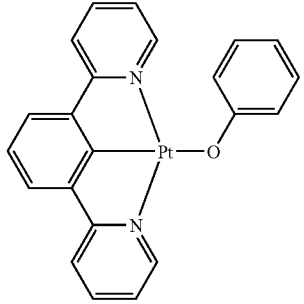 | Appl. Phys. Lett. 86, 153505 (2005) |
|  | 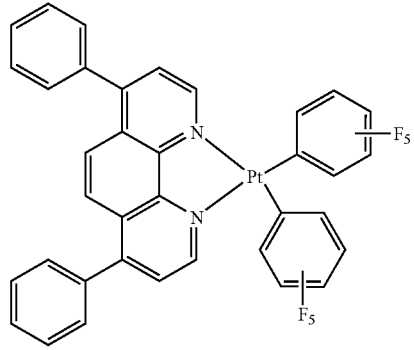 | Chem. Lett. 34, 592 (2005) |
| Gold complexes | 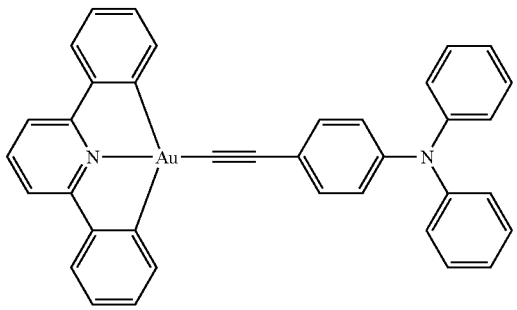 | Chem. Commun. 2906 (2005) |
| Rhenium(III) complexes | 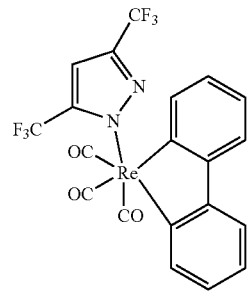 | Inorg. Chem. 42, 1248 (2003) |
| Blue dopants |  |  |
| Iridium(III) organometallic complexes | 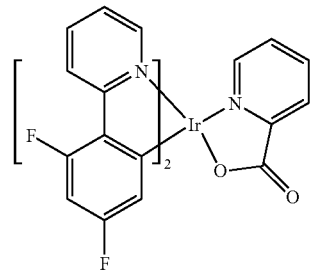 | WO2002002714 |

TABLE 2-continued

| MATERIAL | EXAMPLES OF MATERIAL | PUBLICATIONS |
|---|---|---|
| | | WO2006009024 |
| | | US2006251923 |
| | | WO2006056418, US2005260441 |
| | | US2007190359 |
| | | US2002134984 |
| | | Angew. Chem. Int. Ed. 47, 1 (2008) |

TABLE 2-continued

| MATERIAL | EXAMPLES OF MATERIAL | PUBLICATIONS |
|---|---|---|
| | | Chem. Mater. 18, 5119 (2006) |
| | | Inorg. Chem. 46, 4308 (2007) |
| | | WO05123873 |
| | | WO05123873 |
| | | WO07004380 |

TABLE 2-continued

| MATERIAL | EXAMPLES OF MATERIAL | PUBLICATIONS |
|---|---|---|
| | (Ir complex structure) | WO06082742 |
| Osmium(II) complexes | (Os complex structure) | US2005260449 |
| | (Os(PPh$_3$) complex structure) | Organometallics 23, 3745 (2004) |
| Gold complexes | Ph$_2$P–PPh$_2$ / Au–Au / Cl Cl | Appl. Phys. Lett. 74, 1361 (1999) |
| Platinum(II) complexes | (Pt complex structure) | WO06098120, WO06103874 |

TABLE 2-continued
| MATERIAL | EXAMPLES OF MATERIAL | PUBLICATIONS |
|---|---|---|
| Exciton/hole blocking layer materials | | |
| Bathocuprine compounds (e.g., BCP, BPhen) | 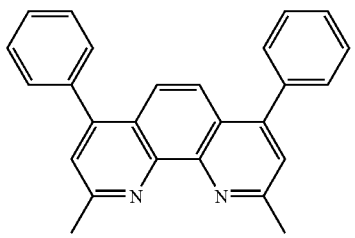 [SMILES: Cc1cc(-c2ccccc2)c2ccc3c(-c4ccccc4)cc(C)nc3c2n1] | Appl. Phys. Lett. 75, 4 (1999) |
| | 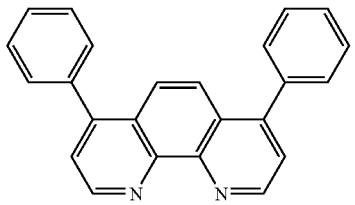 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 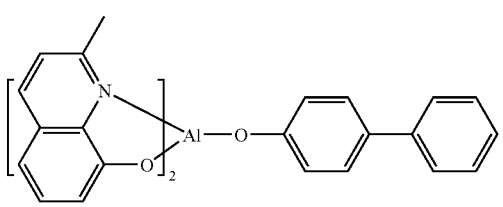 | Appl. Phys. Lett. 81, 162 (2002) |
| 5-member ring electron deficient heterocycles such as triazole, oxadiazole, imidazole, benzoimidazole | 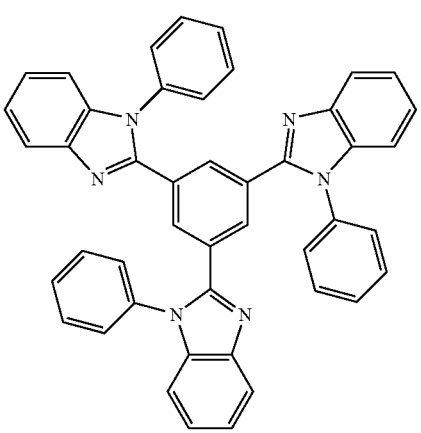 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 2-continued
| MATERIAL | EXAMPLES OF MATERIAL | PUBLICATIONS |
|---|---|---|
| Triphenylene compounds | 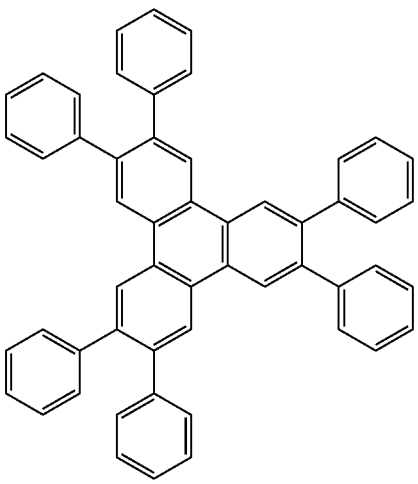 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 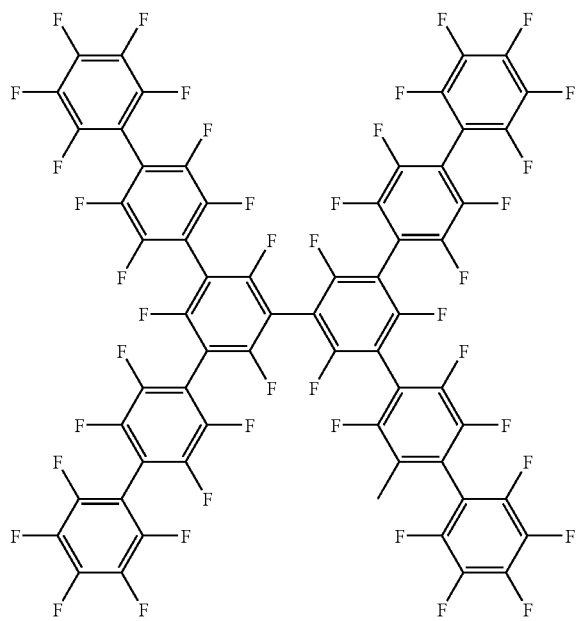 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |

TABLE 2-continued

| MATERIAL | EXAMPLES OF MATERIAL | PUBLICATIONS |
|---|---|---|
| Electron transporting materials | | |
| Anthracene-benzoimidazole compounds | | WO03060956 |
| Anthracene-benzothiazole compounds | | Appl. Phys. Lett. 89, 063504 (2006) |
| Metal 8-hydroxyquinolates (e.g., Alq$_3$) | | Appl. Phys. Lett. 51, 913 (1987) |
| Metal hydroxybenoquinolates | | Chem. Lett. 5, 905 (1993) |
| Bathocuprine compounds such as BCP, BPhen, etc | | Appl. Phys. Lett. 91, 263503 (2007) |

TABLE 2-continued

| MATERIAL | EXAMPLES OF MATERIAL | PUBLICATIONS |
|---|---|---|
| | *(4,7-diphenyl-1,10-phenanthroline structure)* | Appl. Phys. Lett. 79, 449 (2001) |
| 5-member ring electron deficient heterocycles (e.g., triazole, oxadiazole, imidazole, benzoimidazole) | *(1,3,5-tris(N-phenylbenzimidazol-2-yl)benzene structure)* | Appl. Phys. Lett. 74, 865 (1999) |
| | *(2-(4-biphenylyl)-5-(4-tert-butylphenyl)-1,3,4-oxadiazole structure)* | Appl. Phys. Lett. 55, 1489 (1989) |
| | *(3-(4-biphenylyl)-5-(4-tert-butylphenyl)-4-phenyl-1,2,4-triazole structure)* | Jpn. J. Apply. Phys. 32, L917 (1993) |
| Silole compounds | *(silole compound structure)* | Org. Electron. 4, 113 (2003) |
| Arylborane compounds | *(arylborane compound structure)* | J. Am. Chem. Soc. 120, 9714 (1998) |

TABLE 2-continued

| MATERIAL | EXAMPLES OF MATERIAL | PUBLICATIONS |
|---|---|---|
| Fluorinated aromatic compounds | 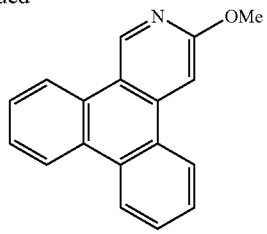 | J. Am. Chem. Soc. 122, 1832 (2000) |

EXPERIMENTAL

Compound Examples

Example 1

Synthesis of Compound 1

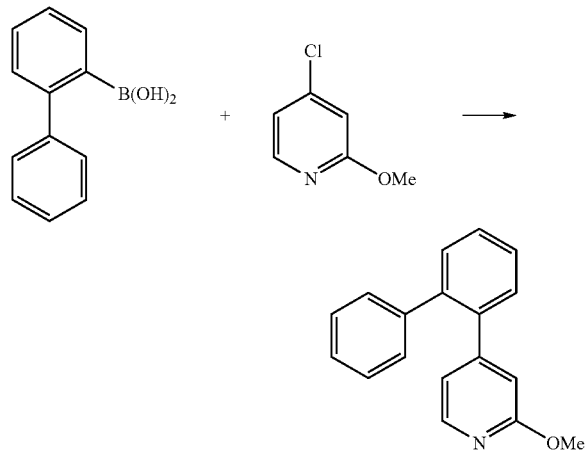

Step 1. Synthesis of 4-(biphenyl-2-yl)-2-methoxypyridine

A nitrogen flushed mixture of 4-chloro-2-methoxypyridine (3.0 g, 21.03 mmol), 2-biphenylboronic acid 5.0 g, 25.23 mmol), Pd$_2$(dba)$_3$ (381 mg, 0.414 mmol), 2-dicyclohexylphosphino-2',6'-dimethoxybiphenyl (681 mg, 1.66 mmol), toluene (250 mL) and a slurry of K$_3$PO$_4$.H$_2$O (14.57 g, 63.09 mmol) in water (25 mL) were refluxed for 18 h. After the mixture cooled to room temperature the organic layer was dried over anhydrous Na$_2$SO$_4$, filtered, and concentrated in vacuum. The residue was purified by flash chromatography on silica (hexane:ethyl acetate) and recrystallized from ethyl acetate to give 4-(biphenyl-2-yl)-2-methoxypyridine (4.2 g, 76.5%).

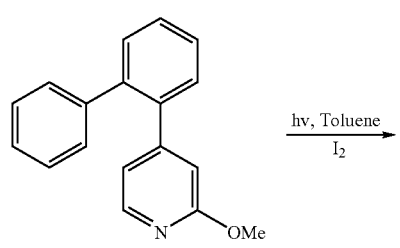

Step 2. Synthesis of 3-methoxydibenzo[f,h]isoquinoline 4-(biphenyl-2-yl)-2-methoxypyridine (2.9 g, 10.9 mmol), iodine (281 mg, 1.1 mmol) and toluene were charged into a double-walled quartz photochemical reactor equipped with magnetic stirring, an air bubbler and an ultraviolet lamp. Gentle air was bubbled through the solvent while it was irradiated for 15 h. The reaction mixture was purified by flash chromatography on silica (hexane:ethyl acetate) and sonicated in MeOH to give 3-methoxydibenzo[f,h]isoquinoline (0.5 g, 17%).

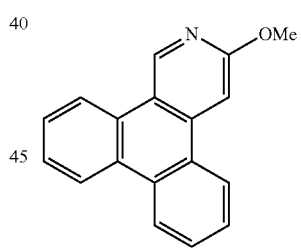

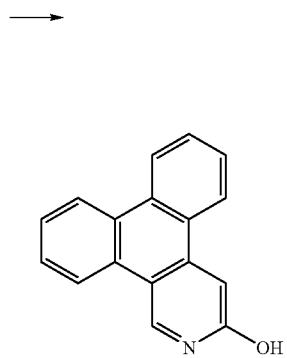

Step 3. Synthesis of dibenzo[f,h]isoquinolin-3-ol 3-methoxydibenzo[f,h]isoquinoline (1.0 g, 3.9 mmol) and pyridine hydrochloride (4.5 g, 39 mmol) were heated at ca. 220° C. for 1.5 h. The reaction was cooled and water was added. The resulting solids were filtered, wash with water and dried in vacuum to give dibenzo[f,h]isoquinolin-3-ol (0.91 g, 95%).

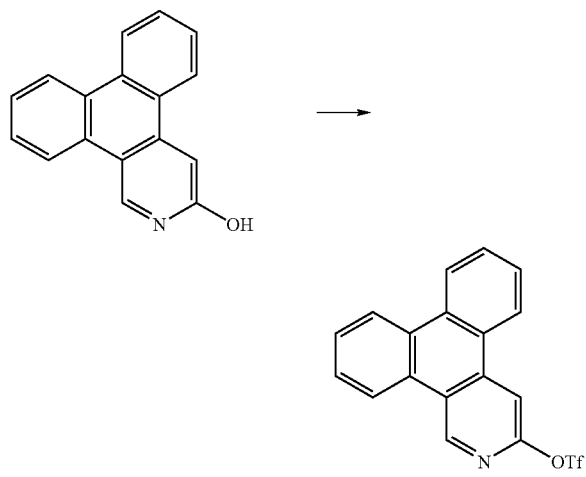

Step 4. Synthesis of dibenzo[f,h]isoquinolin-3-yl trifluoromethanesulfonate

Trifluoromethanesulfonic anhydride (5.2 g, 19 mmol) was added to a mixture of dibenzo[f,h]isoquinolin-3-ol (0.91 g, 3.7 mmol), pyridine (1.2 g, 15 mmol) and dichloromethane 100 mL under nitrogen at 0° C. and stirred overnight at room temperature. The reaction was quenched with saturated NaHCO$_3$. The organic layer was washed with water and dried on Na$_2$SO$_4$. The residue was purified by flash chromatography on silica (hexane:ethyl acetate) to give (1.1 g, 79%).

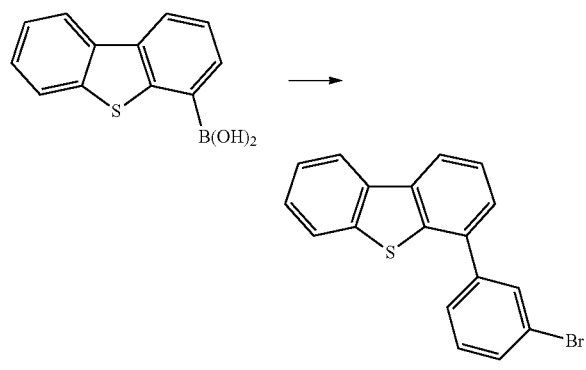

Step 5. Synthesis of 4-(3-bromophenyl)dibenzo[b,d]thiophene

A nitrogen flushed mixture of 1,3-dibromobenzene (18.63 g, 78.92 mmol), dibenzo{b,d}thiophen-4-ylboronic acid (6.0 g, 26.3 mmol), Pd(PPh$_3$)$_4$ (304 mg, 0.414 mmol), toluene (200 mL) and a slurry of K$_2$CO$_3$ (10.9 g, 78.92 mmol) in water (20 mL) were refluxed for 23 h. After the mixture cooled to room temperature the organic layer was washed with water, dried over anhydrous Na$_2$SO$_4$, filtered, and concentrated in vacuo. The residue was purified by vacuum distillation (Kugelrohr) followed by flash chromatography on silica (hexane:dichloromethane) to give 4-(3-bromophenyl)dibenzo[b,d]thiophene (3.5 g 39.2%).

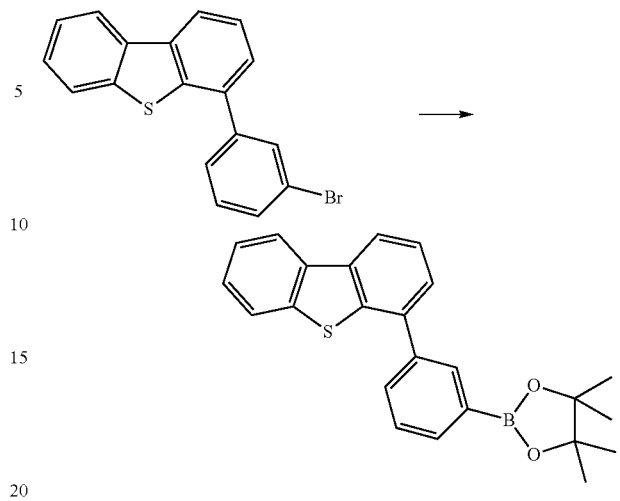

Step 6. Synthesis of 2-(3-(Dibenzo[b,d]thiophen-4-yl)phenyl)-4,4,5,5-tetramethyl-1,3,2-dioxaborolane A nitrogen flushed mixture of 4-(3-bromophenyl)dibenzo[b,d]thiophene (2.4 g 7.07 mmol), 4,4,4',4',5,5,5',5'-octamethyl-2,2'-bi(1,3,2-dioxaborolane (3.58 g, 14 mmol), Pd(dppf)Cl$_2$ (114 mg, 0.14 mmol) and KOAc (2.08 g, 21.2 mmol) was heated in dioxane (100 mL) at 90° C. for 18 h. After the mixture cooled to room temperature, ethyl acetate was added and the organic layer was washed with water, washed with brine, dried over anhydrous Na$_2$SO$_4$ and filtered. Celite was added to the filtrate and then concentrated by vacuum. The residue was purified by flash chromatography on silica (hexane:dichloromethane) followed by vacuum distillation (Kugelrohr) to remove the excess 4,4,4',4',5,5,5',5'-octamethyl-2,2'-bi(1,3,2-dioxaborolane and then crystallized from hexanes:ethyl acetate to give 2-(3-(dibenzo[b,d]thiophen-4-yl)phenyl)-4,4,5,5-tetramethyl-1,3,2-dioxaborolane (1.62 g, 59%).

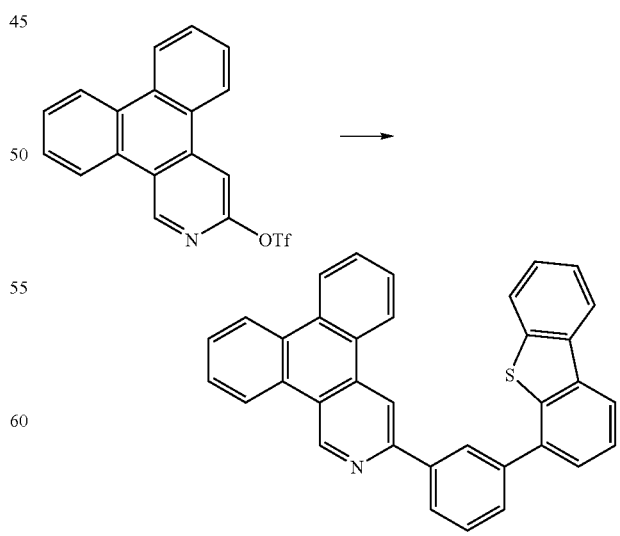

Compound 1

Step 7. Synthesis of 3-(3-(dibenzo[b,d]thiophen-4-yl)phenyl)dibenzo[f,h]isoquinoline The mixture of Step 4 product dibenzo[f,h]isoquinolin-3-yl trifluoromethanesulfonate (1.1 g, 2.9 mmol), Step 6 product 2-(3-(dibenzo[b,d]thiophen-4-yl)phenyl)-4,4,5,5-tetramethyl-1,3,2-dioxaborolane (1.5 g, 3.8 mmol), potassium phosphate tribasic monohydrate (2.0 g, 8.8 mmol), 150 mL toluene and 15 mL water was prepared and bubbled with nitrogen for 20 minutes. Then tris(dibenzylideneacetone)dipalladium(0) (27 mg, 0.029 mmol) and 2-dicyclohexylphosphino-2',6'-dimethoxybiphenyl (48 mg, 0.12 mmol) were added to the mixture. The reaction mixture was bubbled with nitrogen for another 20 minutes and then refluxed overnight. After cooled to room temperature, 2-(3-(dibenzo[b,d]thiophen-4-yl)phenyl)-4,4,5,5-tetramethyl-1,3,2-dioxaborolane (1.3 g, 3.4 mmol), tris(dibenzylideneacetone)dipalladium(0) (60 mg, 0.066 mmol) and 2-dicyclohexylphosphino-2',6'-dimethoxybiphenyl (100 mg, 0.24 mmol) were added to the mixture. The reaction mixture was bubbled with nitrogen for 30 minutes and then refluxed overnight. The mixture then was cooled to room temperature. The organic layer was collected and dried by $MgSO_4$. The crude product was purified by silica gel column to give white solid Compound 1 (1.0 g, 71% yield).

Example 2

Synthesis of Compound 79

Synthesis of ligand 3-phenyldibenzo[f,h]isoquinoline

Dibenzo[f,h]isoquinolin-3-yl trifluoromethanesulfonate compound as synthesized in above Step 4 of Compound 1 synthesis reacts with phenylboronic acid under Suzuki reaction condition as described in Step 7 of Compound 1 synthesis to give the ligand 3-phenyldibenzo[f,h]isoquinoline.

Synthesis of Iridium Complex Compound 79

3-Phenyldibenzo[f,h]isoquinoline ligand mixed with $Ir(acac)_3$ in ethylene glycol are heated up to reflux under nitrogen overnight to give Compound 79. The molar ratio of ligand and $Ir(acac)_3$ is about 3.5 to 1.

Device Examples

All example devices were fabricated by high vacuum (<$10^{-7}$ Torr) thermal evaporation. The anode electrode is approximately 800 Å or 1200 Å of indium tin oxide (ITO). The cathode consisted of 10 Å of LiF followed by 1000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

Particular devices are provided wherein an invention compound, Compound 1, is the host material and the blocking layer material and E1 is the emitting dopant. The organic stack of Device Examples 1-4 consisted of sequentially, from the ITO surface, 100 Å of E1 as the hole injecting layer (HIL), 300 Å of 4,4'-bis-[N-(1-napthyl)-N-phenylamino]biphenyl (α-NPD) as the hole transport layer (HTL), 300 Å of Compound 1 doped with 10-15% of E1, an Ir phosphorescent compound, as the emissive layer (EML), no blocking layer (0 Å) or 50 Å of Compound 1 as the blocking layer (BL) and 450 Å or 500 Å of $Alq_3$ (tris-8-hydroxyquinoline aluminum) as the electron transport layer (ETL).

Comparative Examples 1 and 2 were fabricated similarly to the Device Examples except that the CBP is used as the host and HPT was used as the BL material or there was no blocking layer.

As used herein, the following compounds have the following structures:

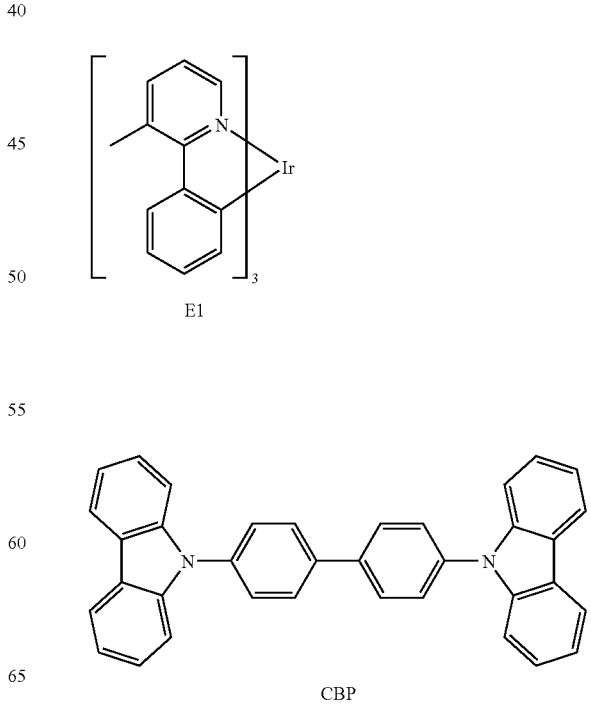

-continued

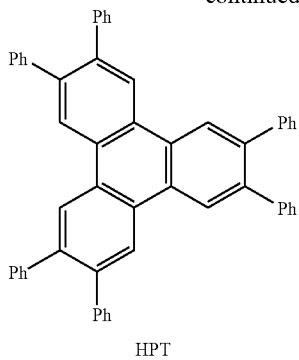

HPT

The device structures and device data are summarized below in Table 3 and Table 4. Table 3 shows the device structures and Table 4 shows the corresponding measured results for those devices.

The following terms are used in Tables 3 and 4, and are defined herein:
Comp. Ex. is an abbreviation for Comparative example. Ex. is an abbreviation for example. Cmpd. is an abbreviation for Compound. LE is luminous efficiency, which is defined as the luminance divided by the driving current density of the OLED. EQE is external quantum efficiency, which is defined as the ratio of measured number of photons to the electrons passed across the junction. PE is power efficiency, which is defined as the total luminous flux emitted divided by the total power input. $L_0$ is the initial luminance, which is defined as the initial brightness at a certain current density. $RT_{80\%}$ is a measure of lifetime, which is defined as the time required for the initial luminance, $L_0$, to decay to 80% of its value, at a constant current density of 40 mA/cm$^2$ at room temperature.

TABLE 3

| Device Example | Host | Dopant % | BL (Å) | ETL (Å) | ITO thickness (nm) |
|---|---|---|---|---|---|
| Comp. Ex. 1 | CBP | E1 10% | HPT (50) | Alq$_3$ (450) | 120 |
| Comp. Ex. 2 | CBP | E1 10% | None (0) | Alq$_3$ (500) | 120 |
| Ex. 1 | Cmpd. 1 | E1 10% | Cmpd. 1 (50) | Alq$_3$ (450) | 120 |
| Ex. 2 | Cmpd. 1 | E1 10% | None (0) | Alq$_3$ (500) | 120 |
| Ex. 3 | Cmpd. 1 | E1 15% | Cmpd. 1 (50) | Alq$_3$ (450) | 120 |
| Ex. 4 | Cmpd. 1 | E1 15% | None (0) | Alq$_3$ (500) | 120 |

TABLE 4

| | At L = 1000 cd/m$^2$ | | | | | At J = 40 mA/cm$^2$ | |
|---|---|---|---|---|---|---|---|
| | CIE | | | | | | |
| Example | X | Y | V (V) | LE (cd/A) | EQE (%) | PE (lm/W) | $L_0$ (cd/m$^2$) | $LT_{80\%}$ (hr) |
| Comp. Ex. 1 | 0.346 | 0.613 | 6.2 | 57.0 | 16.0 | 28.9 | 13,304 | 105 |
| Comp. Ex. 2 | 0.340 | 0.619 | 7.3 | 11.1 | 3.0 | 4.8 | 7,916 | 100 |
| Ex. 1 | 0.357 | 0.606 | 5.9 | 56 | 15.4 | 29.6 | 15,423 | 92 |
| Ex. 2 | 0.358 | 0.605 | 5.7 | 46.4 | 12.8 | 25.5 | 14,467 | 83 |
| Ex. 3 | 0.367 | 0.599 | 5.7 | 58.1 | 16.1 | 31.9 | 16,393 | 136 |
| Ex. 4 | 0.370 | 0.597 | 6.1 | 32.5 | 9.0 | 16.7 | 13,101 | 120 |

The devices of Comparative Example 1 and Comparative Example 2 use thicknesses and dopant concentrations that were optimized for combinations of materials used in previous device studies. Device Example 1 and Device Example 2 have the same device structure and concentration of materials as used in Comparative Example 1 and Comparative Example 2, but the novel 2-azatriphenylene compounds provided herein have been substituted in place of CBP as the host material and HPT as the blocking layer material. It can be seen from these device examples that Compound 1 as a host in green phosphorescent OLEDs gives high device efficiency (LE>40 cd/A at 1000 cd/m$^2$), indicating the azatriphenylenes linked with dibenzothiophenes, have triplet energy high enough for efficient green electrophosphorescence. This is consistent with the experimental results that the triplet energy of Compound 1 (T1: 476 nm), which is high enough to accommodate a green phosphorescent dopant.

Device Example 2 and Comparative Example 2 results suggest that, as predicted, the Compound 1 host can significantly increase efficiency without a hole blocking layer because it is more electron transporting material as indicated by the relatively low LUMO of the 2-azatriphenylene moiety.

While demonstrating generally favorable properties of the novel 2-azatriphenylene compounds provided herein, Device Examples 1 and 2 were not optimized for lifetime analysis. In Device Example 3 and Device Example 4 the dopant concentration was adjusted as appropriate for these materials to measure device lifetime. In Device Examples 3 and 4, it can be seen that the 2-azatriphenylene compounds significantly improve lifetime, as compared to Comparative Example 1 and Comparative Example 2 respectively. In addition, the Device Examples 3 and 4 improve lifetime while maintaining good efficiency.

The high stability of devices incorporating Compound 1 as the host is notable in Device Example 3 and 4. The lifetime, $T_{80\%}$ (defined as the time required for the initial luminance, $L_0$, to decay to 80% of its value, at a constant current density of 40 mA/cm$^2$ at room temperature) for Device Example 3 and Comparative 1 are 136 hours and 105 hours respectively, with Device Example 1 having a slightly higher $L_0$.

The data suggest that hosts containing azatriphenylenes are good host and enhancement layer materials for phosphorescent OLEDs, providing as least the similar efficiency and improvement in stability compared to the commonly used CBP as the host. More conjugated versions of triphenylene containing benzoselenophenes, for example triphenylene and dibenzoselenophene units linked via p-phenylene (such as 4,4'-biphenyl) may be very suitable for lower energy (yellow to red) phosphorescent OLEDs.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound including the structure;

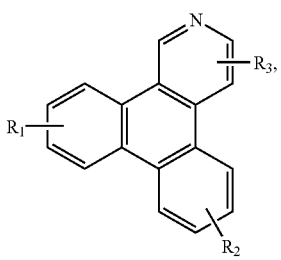

FORMULA I wherein R₁, R₂, and R₃ may represent up to tetra substitutions;
wherein R₁, R₂, and R₃ are independently selected from the group consisting of hydrogen, alkyl, alkoxy, amino, alkenyl, alkynyl, arylkyl, aryl, and heteroaryl; and
wherein at least one of R₁, R₂, and R₃ comprises a heteroaryl.

2. The compound of claim 1, herein the compound has the formula:

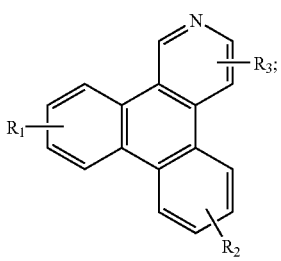

FORMULA I and
wherein the compound is not coordinated to a metal.

3. The compound of claim 1, wherein R₃ is a substitution ortho to the nitrogen.

4. The compound of claim 1, wherein R₁ comprises a heteroaryl.

5. The compound of claim 1, wherein R₂ comprises a heteroaryl.

6. The compound of claim 1, wherein R₃ comprises a heteroaryl.

7. The compound of claim 1, wherein each of R₁, R₂, and R₃ comprises a heteroaryl.

8. A compound comprising a ligand L having a formula selected from the group consisting of:

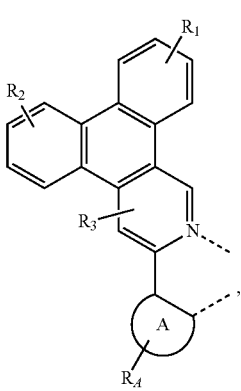

FORMULA II

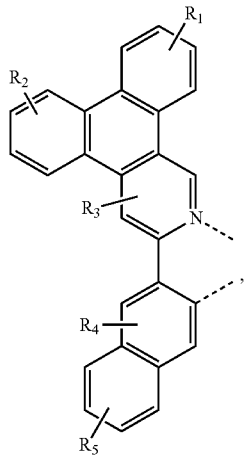

Compound 76G

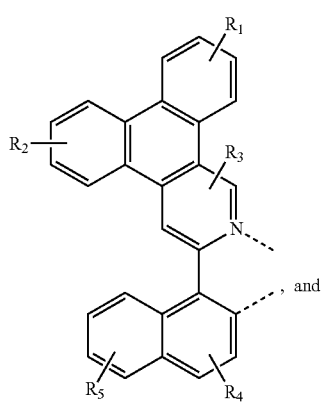

Compound 77G

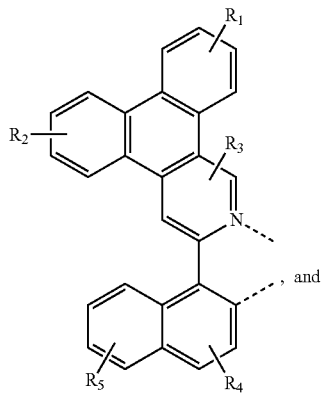

, and

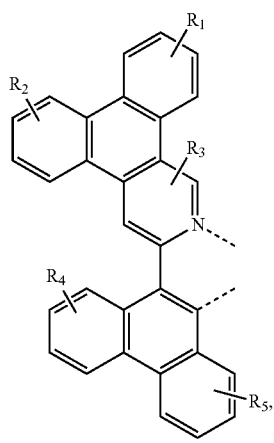

Compound 78G wherein A is a 5-membered or 6-membered aryl or heteroaryl ring;
wherein R₄ may represent up to tetra substitutions;
wherein R₄ is selected from the group consisting of hydrogen, alkyl, alkoxy, amino, alkenyl, alkynyl, arylkyl, aryl, and heteroaryl;
wherein R₁, R₂, R₃, R₄, and R₅ may represent up to tetra substitutions;
wherein R₁, R₂, R₃, R₄ and R₅ are independently selected from the group consisting of hydrogen, alkyl, alkoxy, amino, alkenyl, alkynyl, arylkyl, aryl, and heteroaryl; and
wherein the ligand L is coordinated to a metal having an atomic number greater than 40.

9. The compound of claim 8, wherein the metal is Ir.

10. The compound of claim 9, wherein the ligand L is included in a homoleptic compound.

11. The compound of claim 9, wherein the ligand L is included in a heteroleptic compound.

12. The compound of claim 11, wherein the compound has the formula $(L)_n(L')_{3-n}Ir$:

wherein n is 1 or 2;

wherein L' is selected from the group consisting of:

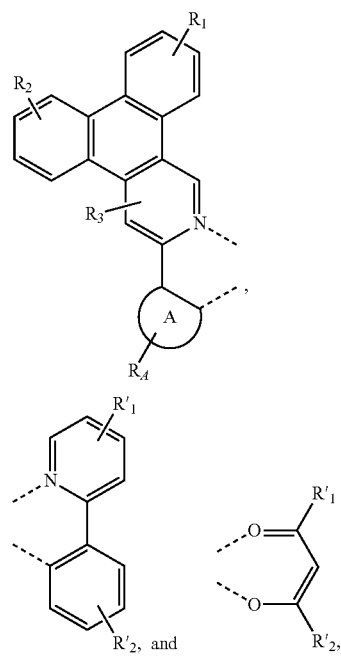

wherein $R_1$, $R_2$, $R_3$, $R_A$, and Ring A independently have meanings as set forth for Formula II;

wherein $R'_1$ and $R'_2$ may represent up to tetra substitutions;

wherein $R'_1$ and $R'_2$ are independently selected from the group consisting of hydrogen, alkyl, alkoxy, amino, alkenyl, alkynyl, arylkyl, aryl, and heteroaryl; and wherein L has a different structure than L'.

13. The compound of claim 8, wherein the ligand L is selected from the group consisting of:

Compound 71G

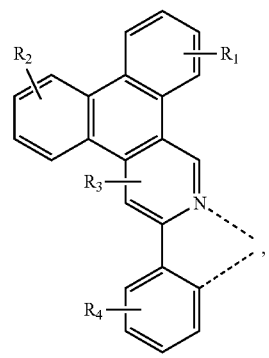

Compound 72G

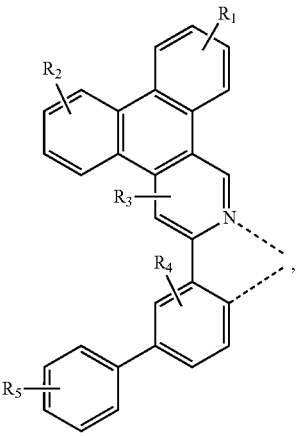

Compound 73G

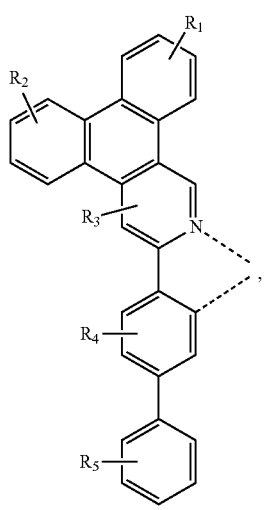

Compound 74G

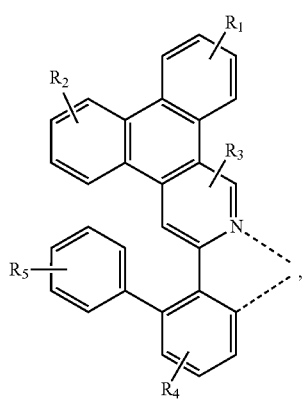

-continued

Compound 76G

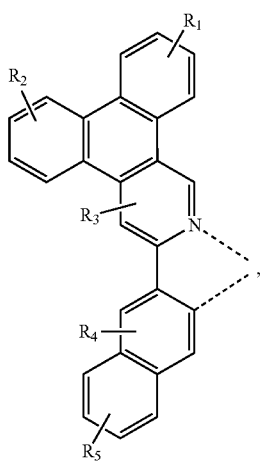

Compound 77G

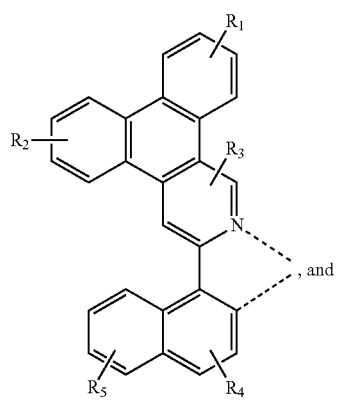
, and

Compound 78G

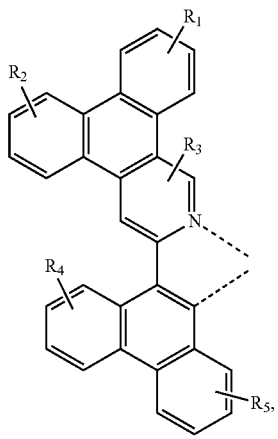

wherein $R_4$ and $R_5$ may represent up to tetra substitutions;
wherein $R_6$ may represent up to penta substitutions; and
wherein each $R_4$, $R_5$, and $R_6$ is independently selected from the group consisting of hydrogen, alkyl, alkoxy, amino, alkenyl, alkynyl, arylkyl, aryl, and heteroaryl.

14. The compound of claim 8, wherein the ligand L is selected from the group consisting of:

Compound 71

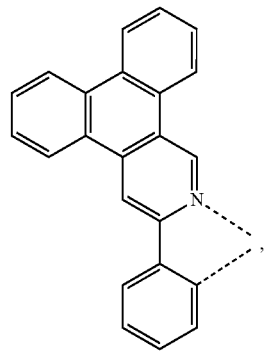

Compound 72

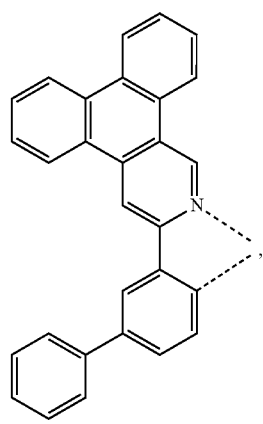

Compound 73

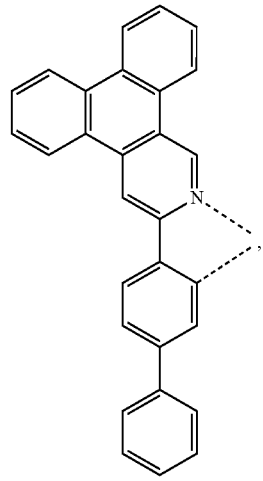

Compound 74

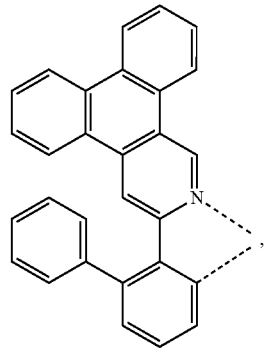

Compouund 76
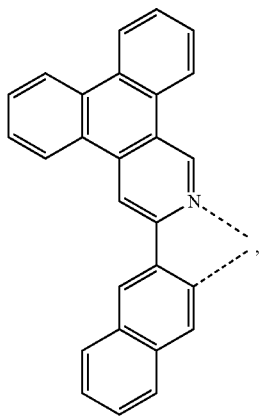
Compound 77
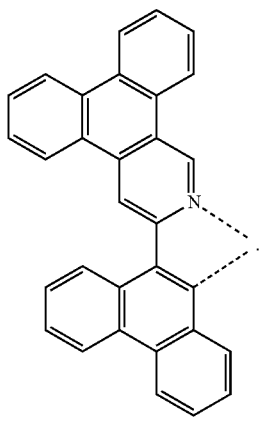
, and
Compound 78
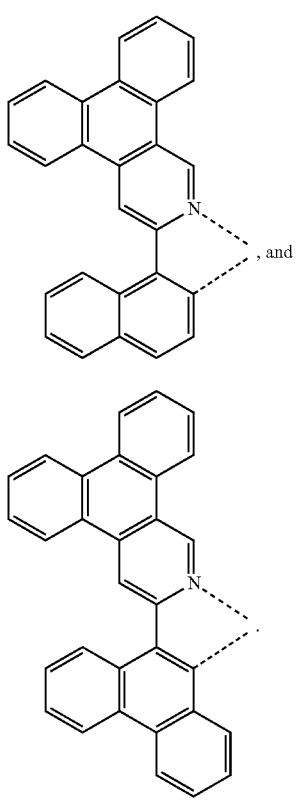
15. The compound of claim 8, wherein the compound is selected from the group consisting of:
Compound 79
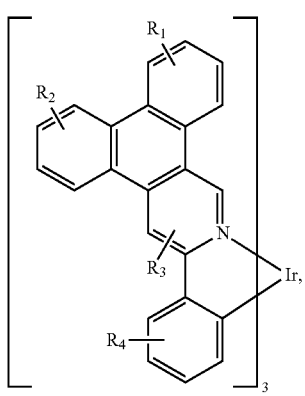
Compound 80
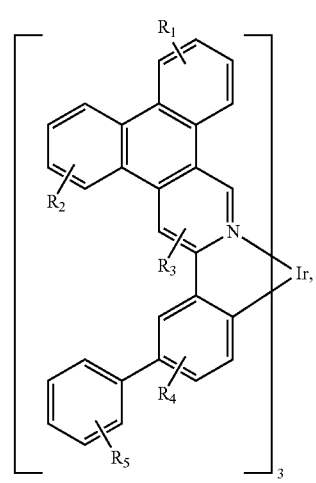
Compound 81
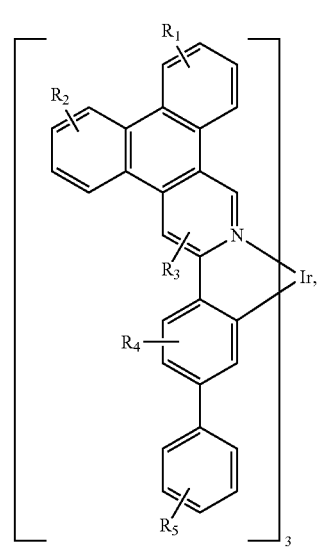
Compound 82
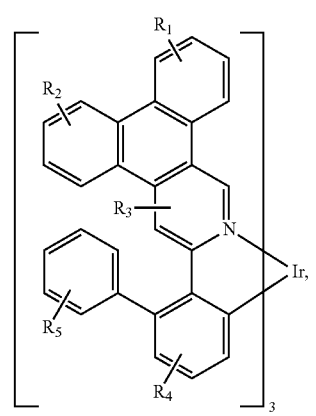

Compound 85
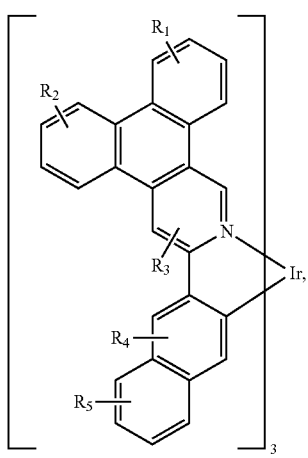
Compound 88
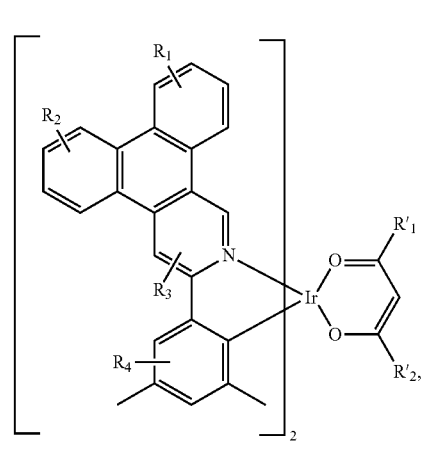
Compound 86
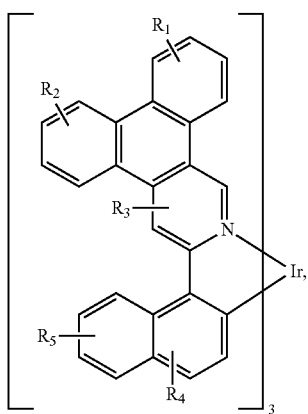
Compound 91
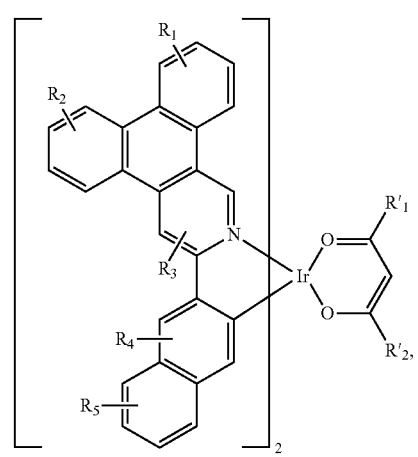
Compound 87
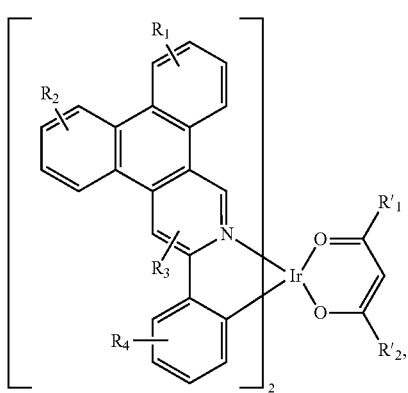
Compound 92
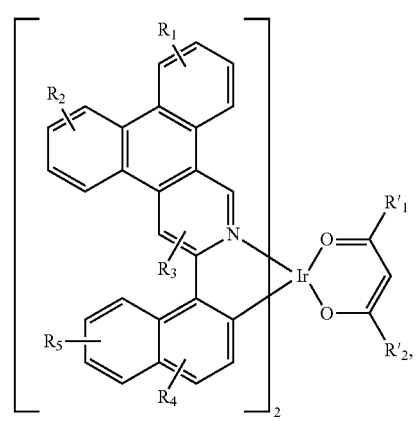

Compound 93

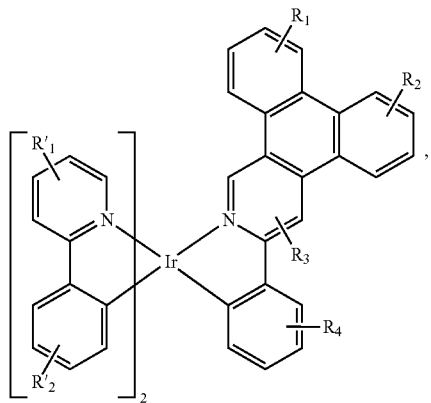

Compound 94

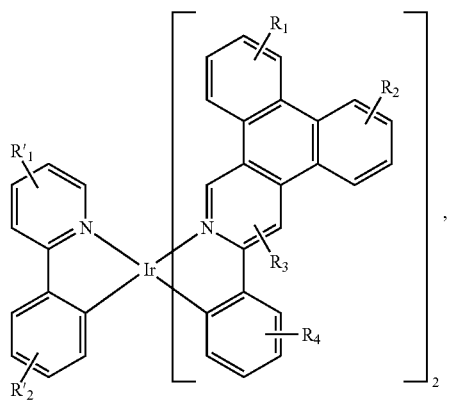

Compound 95

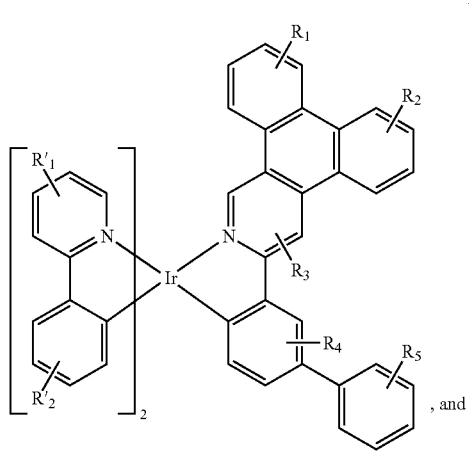
, and

Compound 96

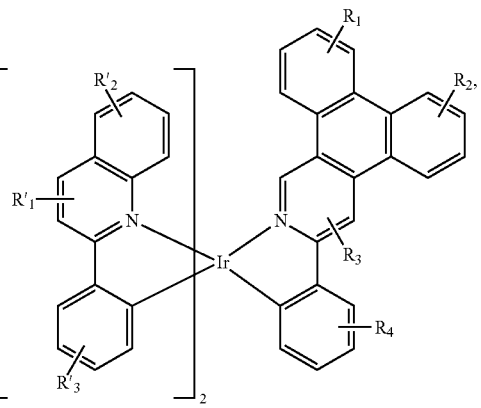

wherein R'₁, R'₂, R₃', and R₆ are independently up to penta substituted, and wherein R'₁, R'₂, R₃', and R₆ are independently selected from the group consisting of hydrogen, alkyl, alkoxy, amino, alkenyl, alkynyl, arylkyl, aryl, and heteroaryl.

16. The compound of claim 8, wherein the compound is selected from the group consisting of:

Compound 79

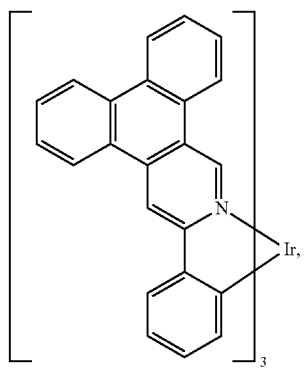

Compound 80

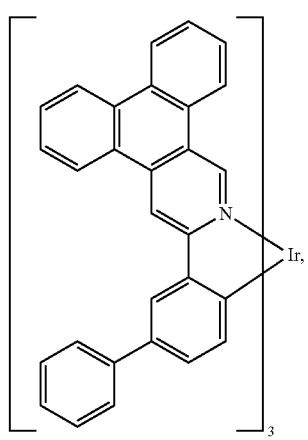

-continued
Compoung 81
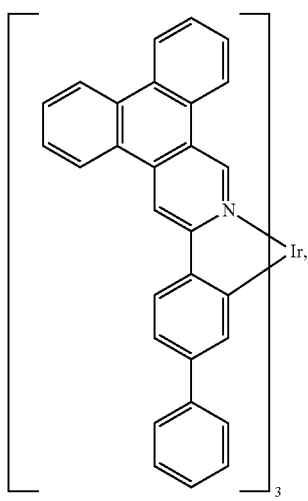
Compound 82
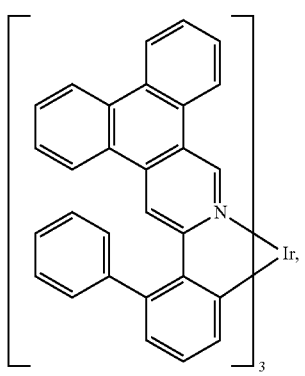
Compound 85
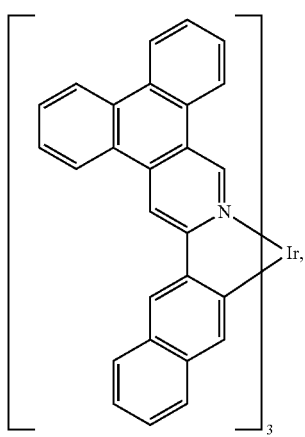
Compound 86
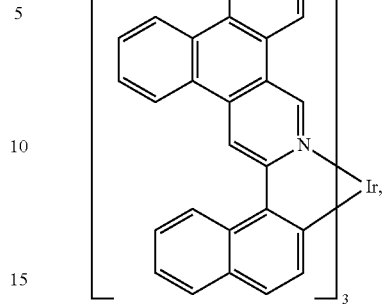
Compound 87
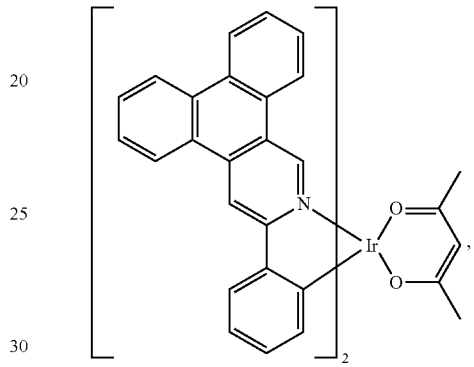
Compound 88
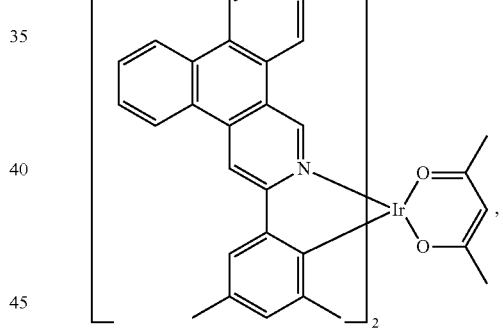
Compound 91
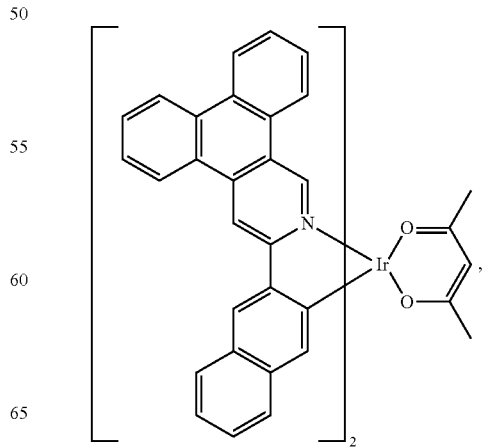

Compound 92

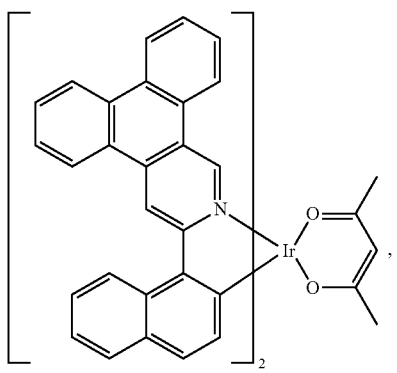

Compound 93

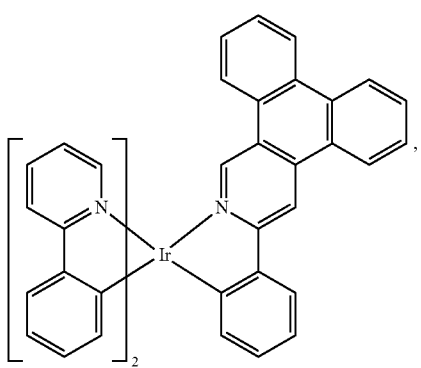

Compound 94

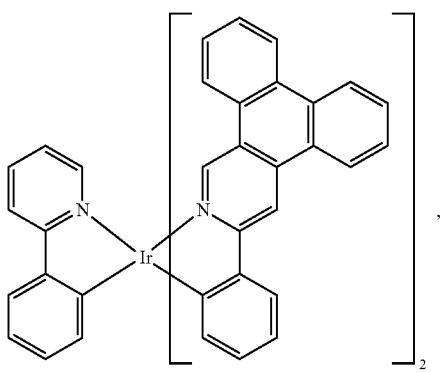

Compound 95

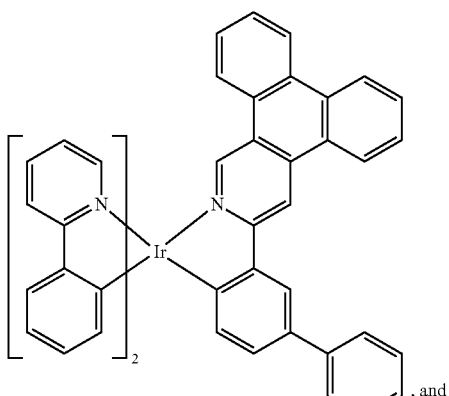, and

Compound 96

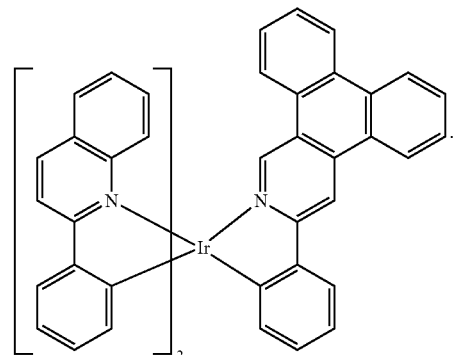

17. A first device comprising an organic light emitting device, comprising:
an anode;
a cathode; and
a first organic layer, disposed between the anode and the cathode, the first organic layer further comprising a compound that includes the structure:

FORMULA I

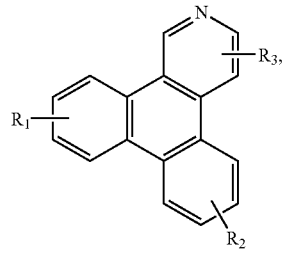

wherein $R_1$, $R_2$, and $R_3$ may represent up to tetra substitutions;
wherein $R_1$, $R_2$, and $R_3$ are independently selected from the group consisting of hydrogen, alkyl, alkoxy, amino, alkenyl, alkynyl, arylkyl, aryl, and heteroaryl; and
wherein at least one of $R_1$, $R_2$, and $R_3$ comprises a heteroaryl.

18. The first device of claim 17, wherein the compound has the formula:

FORMULA I

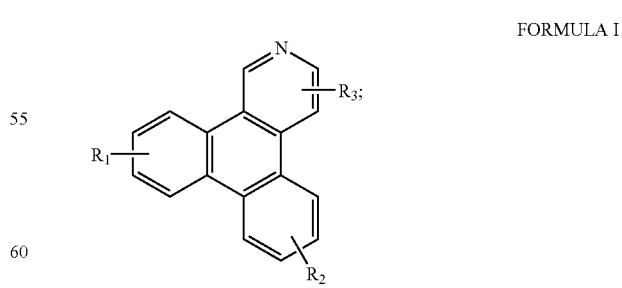

and
wherein the compound is not coordinated to a metal.

19. The first device of claim 17, wherein the first device is a consumer product.

20. A first device comprising an organic light emitting device, comprising:
an anode;
a cathode; and
a first organic layer, disposed between the anode and the cathode, the first organic layer further comprising a compound comprising
a ligand L having a formula selected from the group consisting of:

FORMULA II

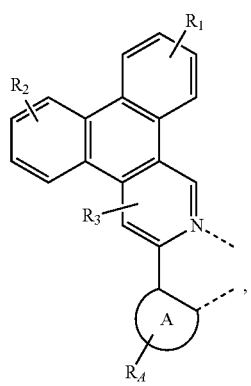

Compound 76G

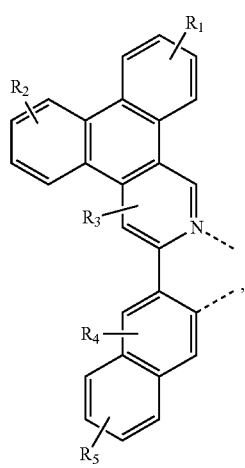

Compound 77G

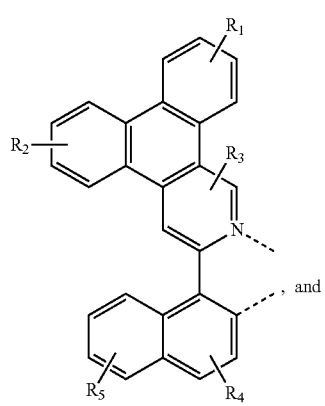, and

Compound 78G

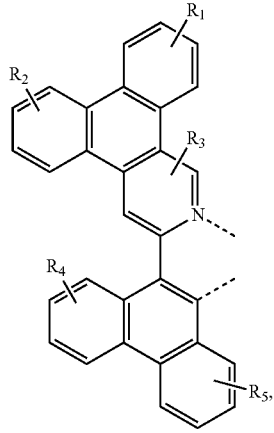

wherein A is a 5-membered or 6-membered aryl or heteroaryl ring;
wherein $R_A$ may represent up to tetra substitutions;
wherein $R_A$ is selected from the group consisting of hydrogen, alkyl, alkoxy, amino, alkenyl, alkynyl, arylkyl, aryl, and heteroaryl;
wherein $R_1$, $R_2$, $R_3$, $R_4$, and $R_5$ may represent up to tetra substitutions;
wherein $R_1$, $R_2$, $R_3$, $R_4$ and $R_5$ are independently selected from the group consisting of hydrogen, alkyl, alkoxy, amino, alkenyl, alkynyl, arylkyl, aryl, and heteroaryl; and
wherein the ligand L is coordinated to a metal having an atomic number greater than 40.

21. The compound of claim 1, wherein the compound is selected from the group consisting of:

Compound 1G

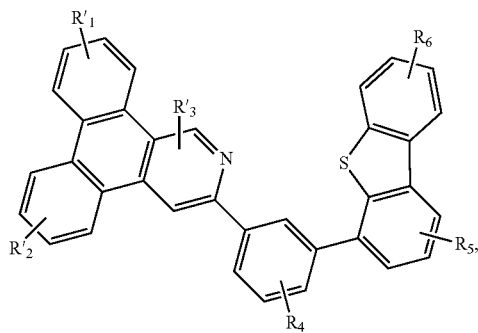

Compound 3G

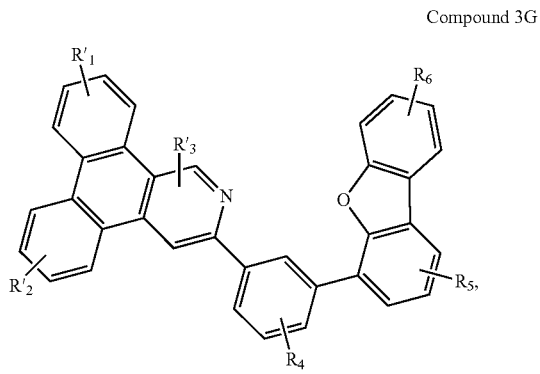

-continued
Compound 4G
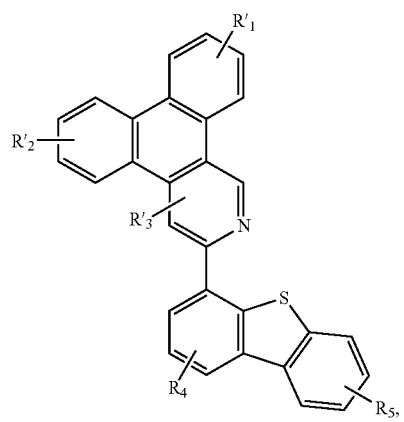
Compound 5G
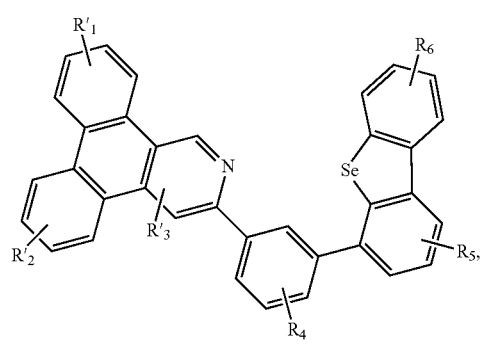
Compound 6G
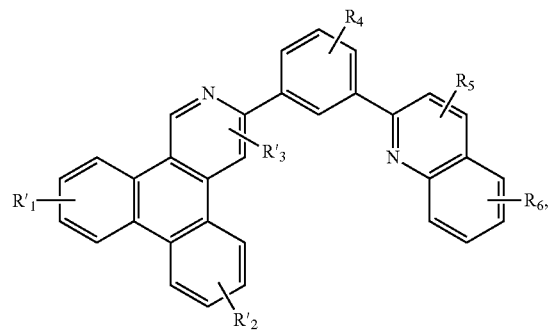
Compound 7G
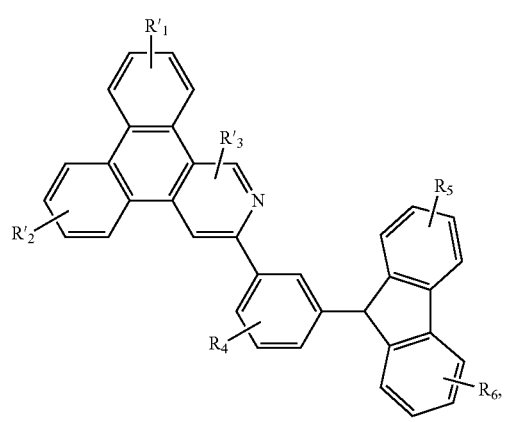
Compound 9G
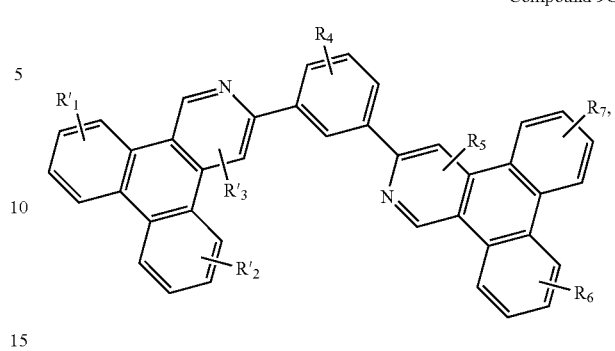
Compound 10G
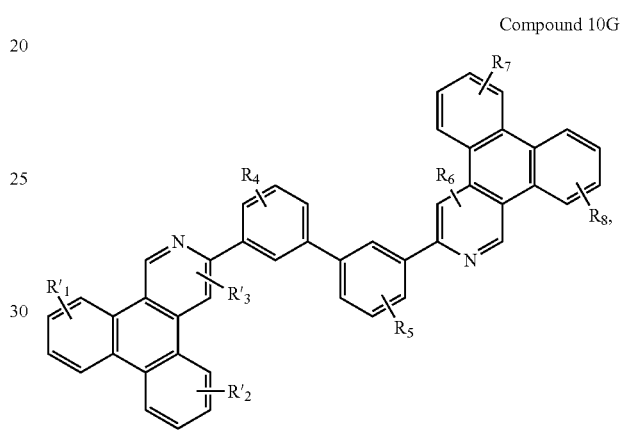
Compound 12G
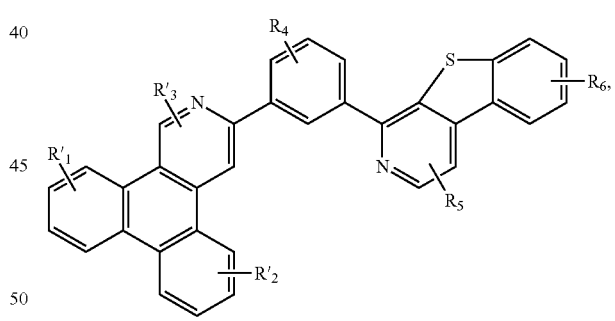
Compound 13G
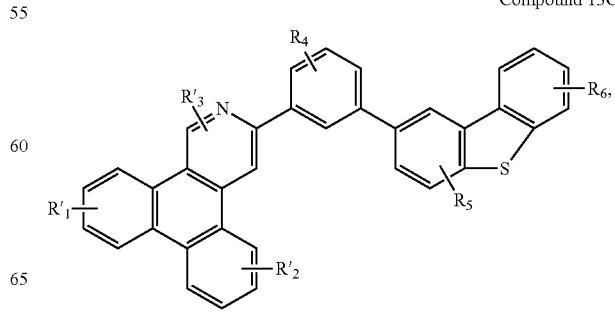

Compound 14G
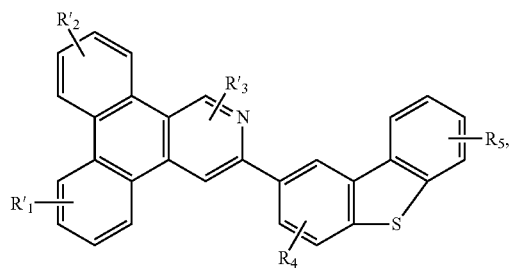
Compound 15G
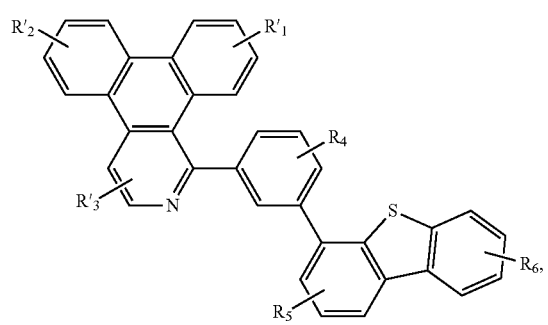
Compound 17G
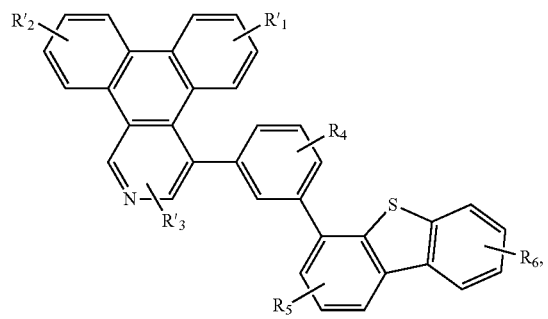
Compound 19G
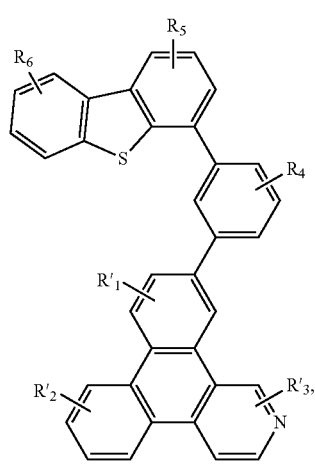
Compound 20G
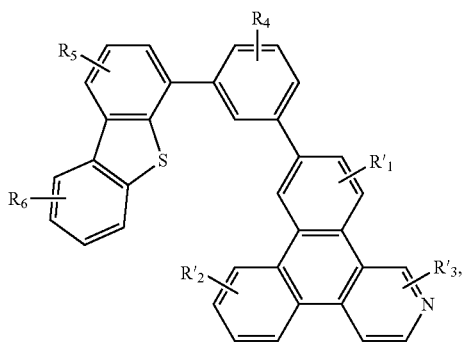
Compound 21G
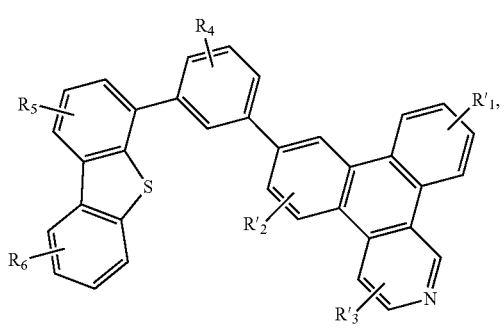
Compound 22G
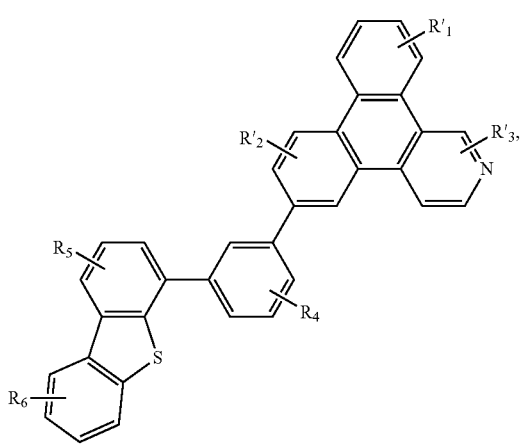
Compound 23G
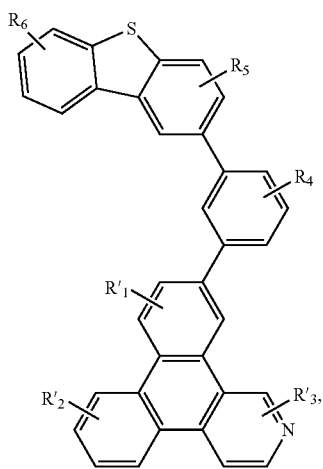

-continued
Compound 24G
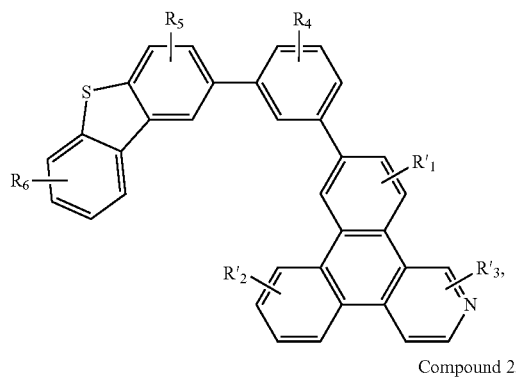
Compound 25G
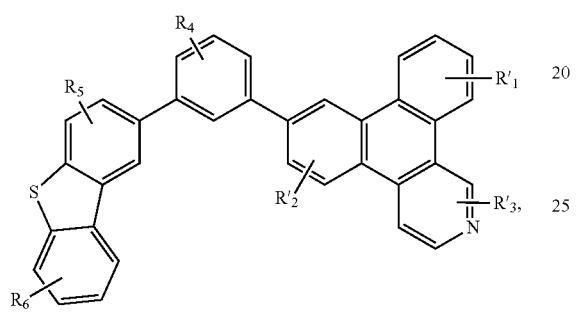
Compound 26G
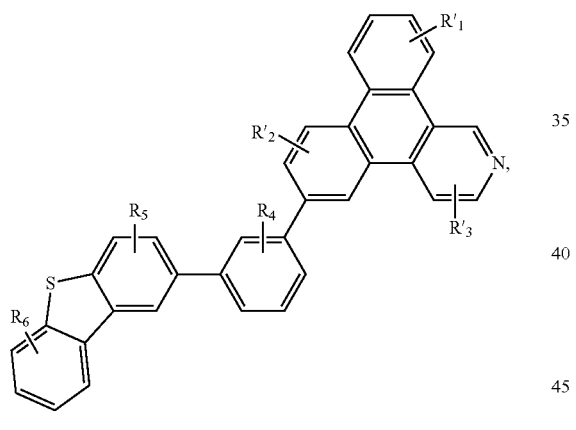
Compound 31G
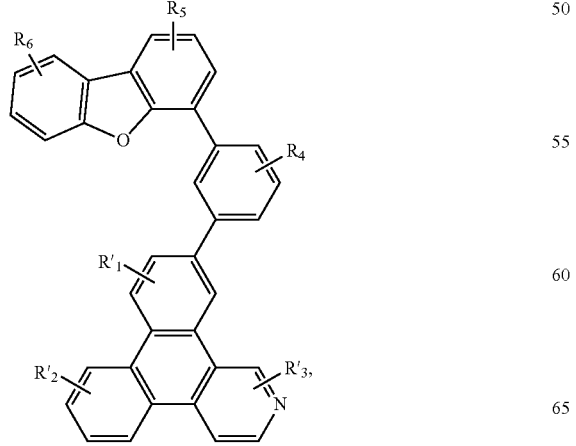
Compound 32G
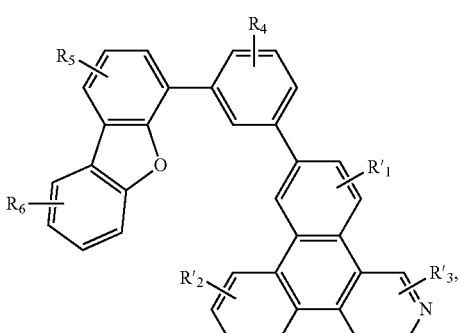
Compound 33G
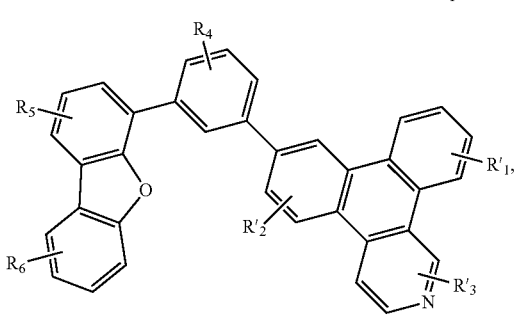
Compound 34G
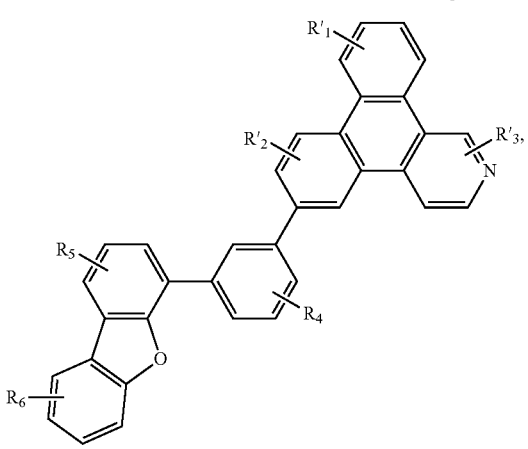
Compound 35G
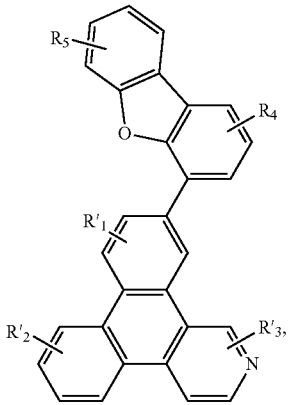

-continued

Compound 36G

Compound 37G

Compound 38G

Compound 39G

Compound 40G

Compound 41G

Compound 42G

Compound 47G

Compound 45G
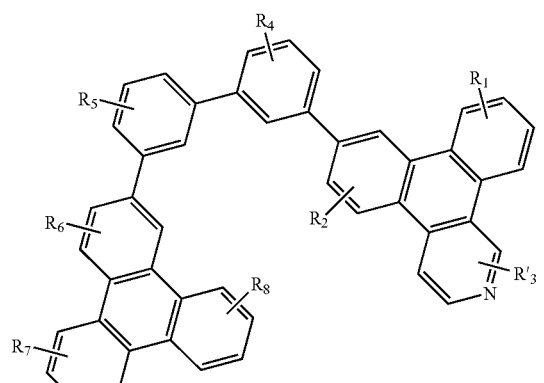
Compound 48G
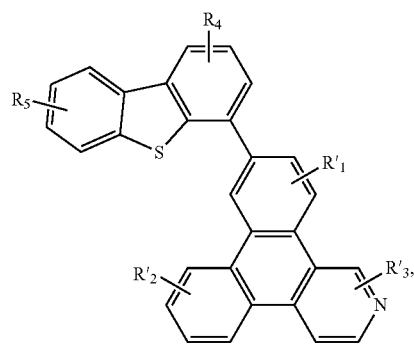
Compound 49G
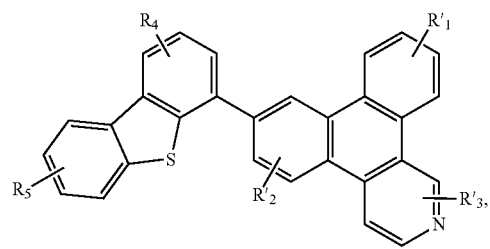
Compound 50G
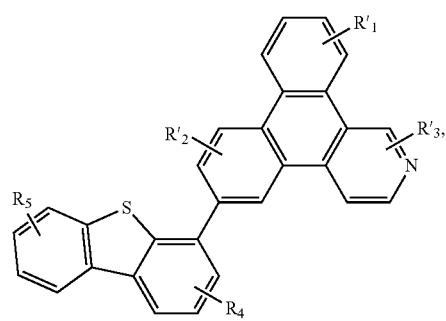
Compound 51G
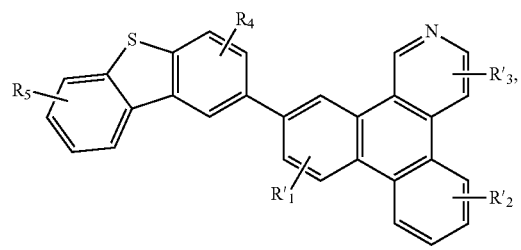
Compound 52G
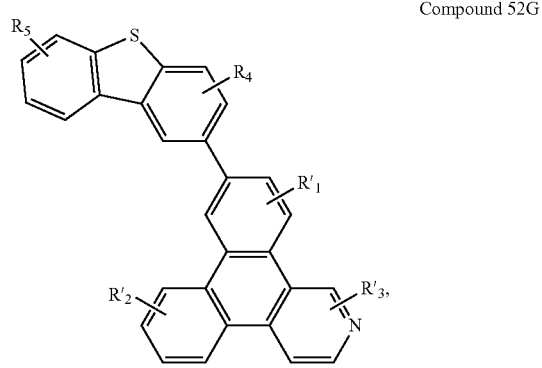
Compound 53G
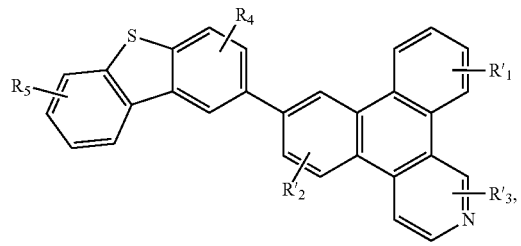
Compound 54G
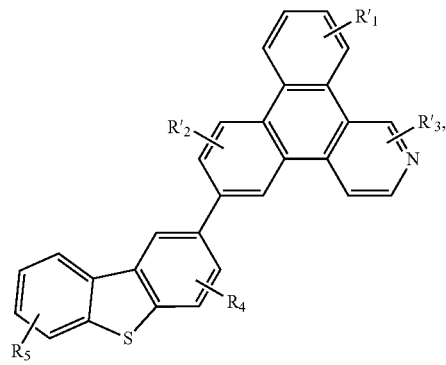

Compound 55G
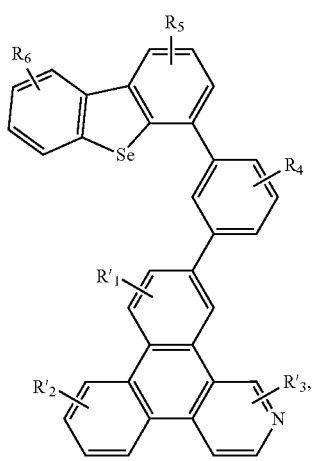
Compound 56G
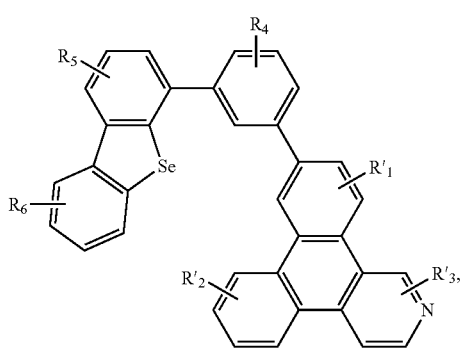
Compound 57G
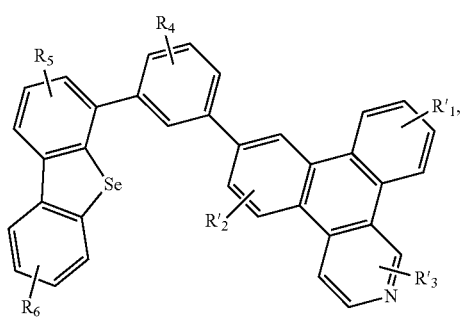
Compound 58G
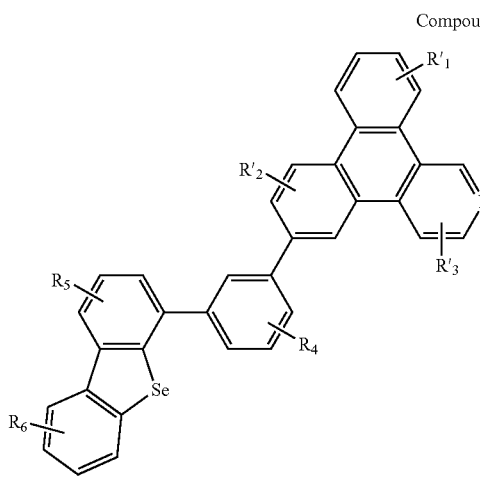
Compound 59G
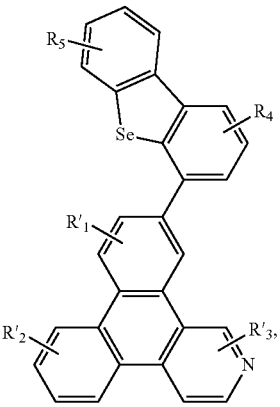
Compound 60G
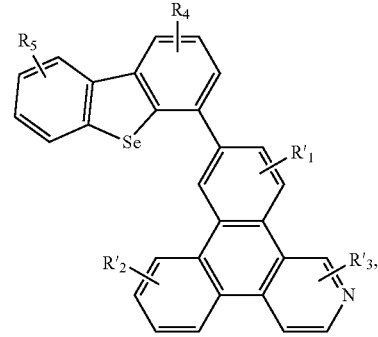
Compound 61G
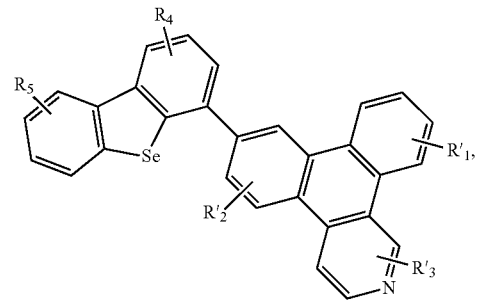
Compound 62G
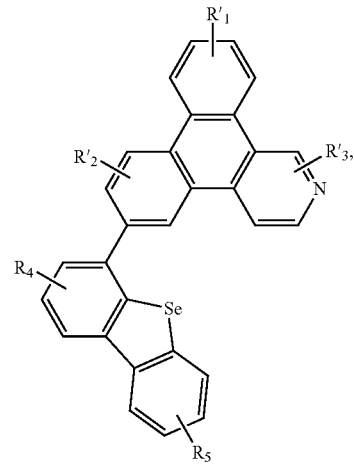

Compound 63G
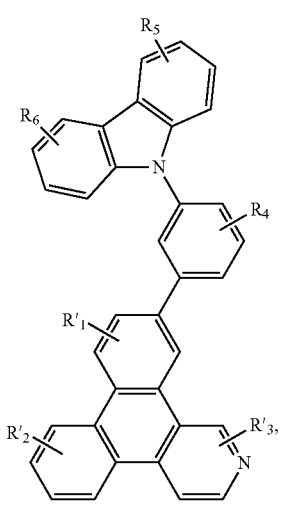
Compound 64G
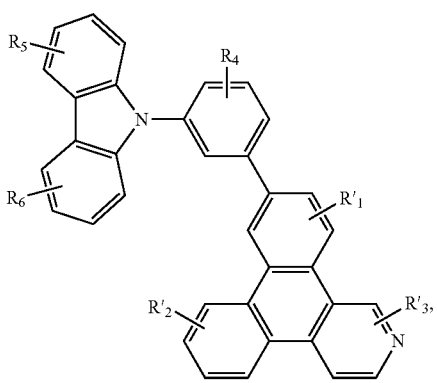
Compound 65G
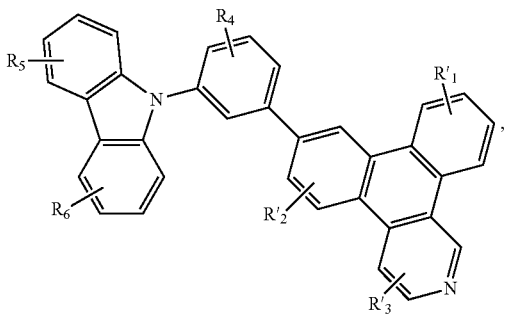
Compound 66G
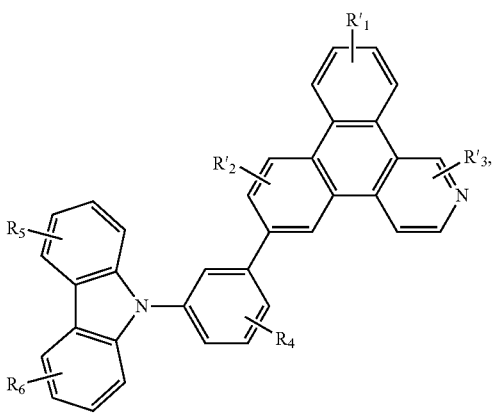
Compound 67G
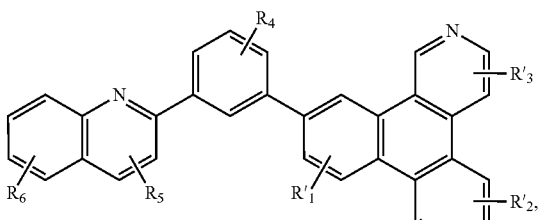
Compound 68G
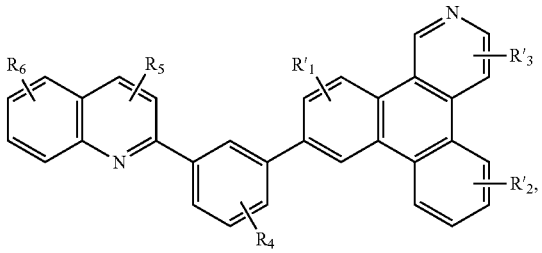
Compound 69G
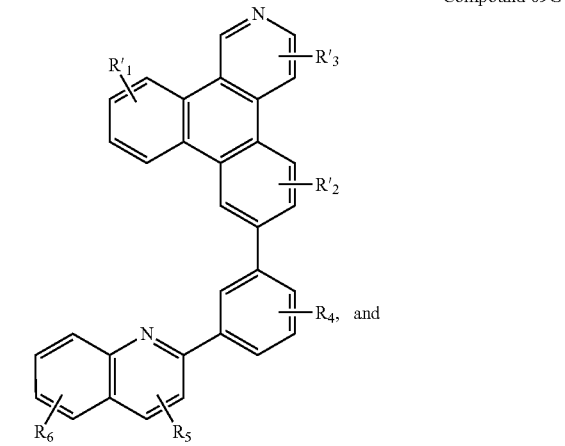
Compound 70G
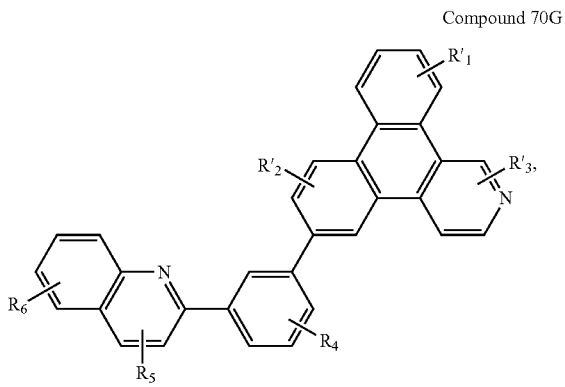
wherein $R'_1$, $R'_2$, $R'_3$, $R_4$, $R_5$, $R_6$, $R_7$, and $R_8$ may represent up to tetra substitutions; and
wherein $R'_1$, $R'_2$, $R'_3$, $R_4$, $R_5$, $R_6$, $R_7$, and $R_8$ are independently selected from the group consisting of hydrogen, alkyl, alkoxy, amino, alkenyl, alkynyl, arylkyl, aryl, and heteroaryl.
* * * * *